(12) United States Patent
Rong et al.

(10) Patent No.: US 11,224,859 B2
(45) Date of Patent: Jan. 18, 2022

(54) CARBON-COATED TRANSITION METAL NANOCOMPOSITE MATERIAL, PREPARATION AND APPLICATION THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Junfeng Rong, Beijing (CN); Genghuang Wu, Beijing (CN); Jingxin Xie, Beijing (CN); Mingsheng Zong, Beijing (CN); Weiguo Lin, Beijing (CN); Peng Yu, Beijing (CN); Hongbo Ji, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 102 days.

(21) Appl. No.: 16/630,906

(22) PCT Filed: Jul. 27, 2018

(86) PCT No.: PCT/CN2018/097303
§ 371 (c)(1),
(2) Date: Jan. 14, 2020

(87) PCT Pub. No.: WO2019/020086
PCT Pub. Date: Jan. 31, 2019

(65) Prior Publication Data
US 2020/0269215 A1 Aug. 27, 2020

(30) Foreign Application Priority Data

Jul. 28, 2017 (CN) .......................... 201710627278.5

(51) Int. Cl.
| | | |
|---|---|---|
| B01J 21/18 | (2006.01) | |
| B01D 53/86 | (2006.01) | |
| B01J 23/75 | (2006.01) | |
| B01J 23/755 | (2006.01) | |
| B01J 35/00 | (2006.01) | |
| B01J 35/10 | (2006.01) | |
| B01J 37/04 | (2006.01) | |
| B01J 37/08 | (2006.01) | |
| C07B 43/04 | (2006.01) | |

(52) U.S. Cl.
CPC .......... *B01J 21/18* (2013.01); *B01D 53/8668* (2013.01); *B01J 23/75* (2013.01); *B01J 23/755* (2013.01); *B01J 35/0013* (2013.01); *B01J 35/109* (2013.01); *B01J 35/1038* (2013.01); *B01J 35/1042* (2013.01); *B01J 35/1047* (2013.01); *B01J 35/1061* (2013.01); *B01J 37/04* (2013.01); *B01J 37/084* (2013.01); *B01J 37/088* (2013.01); *C07B 43/04* (2013.01); *B01D 2255/20746* (2013.01); *B01D 2255/20753* (2013.01); *B01D 2255/702* (2013.01); *B01D 2255/9205* (2013.01); *B01D 2257/708* (2013.01)

(58) Field of Classification Search
CPC ......... B01J 21/18; B01J 23/75; B01J 23/755; B01J 35/0013; B01J 35/1038; B01J 35/1042; B01J 35/1047; B01J 35/35; B01J 35/1061; B01J 35/109; B01J 37/04; B01J 37/084; B01J 37/088; B01D 53/8668; B01D 2255/20746; B01D 2255/20753; B01D 2255/702; B01D 2255/9205; B01D 2257/708; C07B 43/04
USPC ....................................................... 502/185
See application file for complete search history.

(56) References Cited

U.S. PATENT DOCUMENTS

| | | | | |
|---|---|---|---|---|
| 5,037,791 A * | 8/1991 | Comolli | ................. | C10G 49/02 |
| | | | | 502/185 |
| 9,101,981 B2 * | 8/2015 | Aoki | ..................... | C22C 1/0425 |

(Continued)

FOREIGN PATENT DOCUMENTS

| | | |
|---|---|---|
| CN | 103722169 A | 4/2014 |
| CN | 105032424 A | 11/2015 |

(Continued)

OTHER PUBLICATIONS

English Translation of the Written Opinion for PCT/CN2018/097303. (Year: 2018).*

(Continued)

*Primary Examiner* — Patricia L. Hailey
(74) *Attorney, Agent, or Firm* — Novick, Kim & Lee, PLLC; Allen Xue

(57) ABSTRACT

A carbon-coated transition metal nanocomposite material includes carbon-coated transition metal particles having a core-shell structure. The shell layer of the core-shell structure is a graphitized carbon layer doped with oxygen and/or nitrogen, and the core of the core-shell structure is a transition metal nanoparticle. The nanocomposite material has a structure rich in mesopores, is an adsorption/catalyst material with excellent performance, can be used for catalyzing various hydrogenation reduction reactions, or used as a catalytic-oxidation catalyst useful for the treatment of volatile organic compounds in industrial exhaust gases.

21 Claims, 35 Drawing Sheets

(56) References Cited

U.S. PATENT DOCUMENTS

| | | | | |
|---|---|---|---|---|
| 9,175,385 B2* | 11/2015 | Kim | ............... | B22F 9/28 |
| 2004/0065619 A1* | 4/2004 | Klabunde | ............... | B01J 20/20 |
| | | | | 210/681 |
| 2014/0087939 A1* | 3/2014 | Kim | ............... | B01J 29/045 |
| | | | | 502/185 |
| 2015/0343428 A1* | 12/2015 | Kim | ............... | B01J 37/08 |
| | | | | 502/185 |
| 2017/0368535 A1* | 12/2017 | Chopra | ............... | B01J 35/002 |
| 2020/0119337 A1* | 4/2020 | Jang | ............... | H01M 10/052 |

FOREIGN PATENT DOCUMENTS

| | | |
|---|---|---|
| CN | 105428614 A | 3/2016 |
| CN | 105478755 A | 4/2016 |
| CN | 105965009 A | 9/2016 |
| CN | 106732733 A | 5/2017 |

OTHER PUBLICATIONS

Bo Tang et al.; "MOF-derived Ni-based nanocomposites as robust catalyst for chemoselective hydrogenation of functionalized nitro compounds"; RSC Advances; 2017, 7, 1531-1539.

An et al., "Mesoporous Ni@C hybrids for a high energy aqueous asymmetric supercapacitor device", Journal of Materials Chemistry A; 2016,4, 9670-9676.

* cited by examiner

CARBON-COATED TRANSITION METAL NANOCOMPOSITE MATERIAL, PREPARATION AND APPLICATION THEREOF

CROSS-REFERENCE TO RELATED APPLICATIONS

The present application is a National Stage application of PCT international application No. PCT/CN2018/097303, filed on Jul. 27, 2018, which claims the priority of the Chinese patent application No. 201710627278.5, titled "Composite material of carbon and transition metal, its preparation and application thereof", filed on Jul. 28, 2017, the contents of which are incorporated herein by reference in their entirety.

TECHNICAL FIELD

The present application relates to the field of carbon-coated metallic nanocomposite materials, particularly to a nanocomposite material comprising carbon-coated transition metal particles, its preparation and application thereof.

BACKGROUND ART

It has been found that nanocarbon catalysts, such as carbon fibers, nanodiamonds, carbon nanotubes, and (oxidized) graphene, are catalytically active for a series of reactions, such as catalytic dehydrogenation, oxidative dehydrogenation, halogenation, hydroxylation, alkylation of hydrocarbons, and liquid-phase oxidation and condensation of aldehydes and ketones. Meanwhile, as a non-metallic material, the nano carbon material has the advantages of corrosion resistance against acid and alkali, stable chemical properties and the like. The active sites of nanocarbon catalysts are mainly the structural defects and heteroatom functional groups of the carbon material, and thus in order to improve the catalytic activity of nanocarbon catalysts, the number of the structural defects and heteroatom functional groups has to be increased, but such an increase would cause a reduction of the stability of the material.

Transition metal nano materials are widely concerned due to their excellent optical, electrical, magnetic and catalytic properties, but because of high reactivity of transition metal nanoparticles, the transition metal nanoparticles are easy to agglomerate or be oxidized and may even spontaneously combust in the air, which has a great influence on the performance and application of such materials.

It can be seen that transition metal nano materials have high catalytic activity and poor stability, while nano carbon materials have good chemical stability but need a further improvement to their catalytic activity. Thus, if the two materials are combined in a proper way, a new synergistic effect may be generated, so that a novel material having unique performance can be obtained.

In recent years, nanocarbon-coated metallic composite materials have become a focus of attention. Such materials comprise a core of metal nanoparticle tightly wrapped by a shell formed by one or more bent graphitized carbon layers, with the metal nanoparticle being isolated from the outside, so that the stability of the composite material is greatly improved. Therefore, such nano materials having the unique core-shell structure have a wide application prospect in the fields of catalytic materials, wave absorbing materials, information storage materials, magneto-optical materials, biomedical materials, lubricating oil additives and the like.

At present, the covering of transition metals with carbon materials have been reported in some relevant documents, but various problems are encountered in the practical application of existing materials, such as low mass transfer efficiency, unstability in use caused by poor carbon coverage and the like. In addition, many problems exist in their manufacturing process, such as harsh manufacturing conditions, complexity of process, low coverage rate, untight wrapping, and easy damage of carbon coating layer and adverse impact on the metal core caused by the nitric acid treatment needed for introducing an oxygen-containing group, and consequently they are not applicable in industrial production and application.

At present, methods for manufacturing carbon-coated metal nanoparticles known in the art mainly include the arc method, the Chemical Vapor Deposition (CVD) method, the high temperature pyrolysis method, the sol-gel method, and the like.

The arc method has the disadvantages of complexity in equipment used, poor operability, and high energy consumption, and is unfavorable to large-scale preparation of materials. As compared with the arc method, the CVD method has lower cost, higher yield and higher productivity, but it has a problem that nanoparticles of metal or compounds thereof with uniform size and good dispersion need to be prepared in advance, and the subsequent products are often accompanied by particles of carbon nanotubes and amorphous carbon generated.

Similar to the CVD method, the structure and properties of the products of the pyrolysis method are greatly affected by the precursor materials. However, the pyrolysis method has the advantages of simple process, low cost, high yield, controllable metal content and the like, and is one of the methods with prospects for large-scale production at present. The pyrolysis method can be mainly divided into two main types, in which the first type of methods comprise directly mixing a carbon source comprising nitrogen atoms (e.g. dicyanodiamine, melamine, urea easily convertible to melamine at high temperature, and the like) and a metal source, and then subjecting the mixture to high-temperature pyrolysis under an inert or reducing atmosphere. The method has the disadvantages of low graphitization efficiency, large consumption of cyanamide ligands and unsatisfactory covering effect. In addition, the method also facilitates the production of carbon nanotubes. Another type of methods comprise forming a crystalline solid material (i.e., metal-organic framework compound, MOF) with a periodic structure by self-assembly connection of metal ions and nitrogen-containing organic ligands in a characteristic reaction as a precursor. Unlike the pyrolysis method of cyanamides, since the metal in MOF is uniformly dispersed at atomic level, MOF is considered as an ideal precursor for pyrolysis, and has become a hot research focus in this field in recent years. The preparation of such precursors generally requires the use of organic solvents, and reactions conducted in reaction vessels under high temperature and high pressure. For example, Chinese Patent Application Publication No. CN105965009A discloses a method for preparing carbon-coated nickel nanoparticles, comprising coordinating $Ni^{2+}$ with aspartic acid and 4,4'-bipyridine ligands, using methanol and water as solvents, under high temperature and high pressure conditions to produce a precursor, and subjecting the precursor to high-temperature pyrolysis in an inert atmosphere. In the reference document Mesoporous Ni@C hybrids for a high energy aqueousasymmetric supercapacitor device, Electronic Supplementary Material (ESI) for Journal of Materials Chemistry A, 2016, 4, 9670-9676

(DOI: 10.1039/c6ta02339 h), carbon-coated nickel nanoparticles are prepared by producing a self-assembly precursor under high temperature and high pressure conditions using iminodiacetic acid as a carbon source, and $Ni(NO_3)_2$ as a metal source, and then subjecting the precursor to high-temperature pyrolysis under Ar atmosphere. The reference document MOF-derived Ni-based nanocomposites as robust catalyst for chemoselective hydrogenation of functionalized nitro compounds, Bo Tang et. al., RSC Advances, 2017, 7, 1531-1539 discloses a method for the synthesis of a porous carbon-coated nickel nanoparticle composite material, comprising first assembling a metal organic framework precursor (MOF) using a nitrogen-free organic ligand under high temperature and high pressure conditions, and then subjecting the precursor to high-temperature pyrolysis. However, generally in the preparation of MOFs, the conditions are relatively severe, the ligands used are expensive, and it is hard to perform mass production. In addition, these methods require the consumption of large amounts of organic compounds as carbon source, and thus are less efficient; and the carbon layer of the prepared carbon-coated material has more pores, and consequently the coverage of the core metal is insufficient, and the metal loss on acid leaching is higher, so that the materials are unstable in use.

The sol-gel method is used to prepare powders by forming a chelate compound of some weak acid and some cation, polymerizing the chelate compound with a polyol to form a solid polymer resin, and then calcining the resin obtained. In such a method, since metal ions are uniformly dispersed in the polymer resin by chemical reaction with the organic acid, mixing can be ensured at atomic level. Chinese Patent Application Publication No. CN105032424A discloses a pechini type sol-gel method, which comprises dispersing a precursor of an active metal in water containing a coordination compound, adding an aqueous polyol solution and a high-molecular auxiliary agent, adding a carrier, stirring for dispersion, carrying out a hydrothermal reaction, separating out the solid in the lower layer, and calcining in an inert atmosphere to obtain a catalyst comprising an active metal coated by carbon. Similar to the MOF method, the sol-gel method also requires the preparation of solid coordination polymers in solvents, and metal particles of the composite material obtained by such a method are not tightly wrapped. In addition, the method requires the use of a high-molecular auxiliary agent, and it is complex in the process.

Mesoporous materials generally refer to a class of porous materials having a pore structure with a pore size between 2-50 nm. The mesoporous materials can play a better role in separation of macromolecules, adsorption and catalytic reaction, and can serve as a microreactor for limited-domain catalysis. Due to the characteristics of high hydrothermal stability, strong hydrophobicity, organophilic property and the like, mesoporous carbon materials have unique advantages in reactions such as hydrogenation, oxidation, decomposition and the like. If carbon-coated transition metal materials can be manufactured with a mesoporous structure, their mass transfer efficiency can be obviously improved, their functional performance can be improved, and their applications can be expanded. At present, the methods for preparing mesoporous carbon materials mainly include the catalytic activation method, the organogel carbonization method and the template method, but those methods are still too complex in the preparation process.

The carbon-coated transition metal materials and the methods for their preparation known in the prior art have their respective disadvantages. Therefore, there is still a need for a carbon-coated transition metal nano material having a better covering of the core metal by carbon layer and a lower loss on acid leaching, and the carbon-coated transition metal nano material is more desirable to have a structure rich in mesopores; meanwhile, there is also a need for a simpler and more cost-effective method for preparing the carbon-coated transition metal nano material, of which the consumption of carbon source precursor is low, and the efficiency is high, particularly, in which an organic metal precursor can be prepared purely in water phase under normal pressure, and more desirably, a carbon-coated transition metal nano material with a structure rich in pores, especially mesopores, can be prepared through high-temperature pyrolysis.

In addition, the industrial exhaust gas often comprises volatile organic compounds (VOCs), which generally refer to organic compounds with a saturated vapor pressure of more than about 70 Pa at normal temperature and a boiling point of less than 250° C. at normal pressure, such as alkanes, aromatics, ether alcohols, halogenated hydrocarbons, etc. The generation and emission of VOCs are most common in chemical and petrochemical industries, and may also be easily encountered in life (e.g. formaldehyde and the like generated during decoration). For example, in the production of maleic anhydride from commercial n-butane, the above-mentioned VOCs are produced as the raw material and the oxygen in air cannot be converted into the product for one hundred percent over the catalyst. VOCs have become one of the main causes of photochemical smog, and have been considered, together with nitrogen oxides, inhalable particles and the like, to be important pollutants concerned in atmospheric quality control. Besides, VOCs are hazardous in some other aspects, such as high toxicity, and carcinogenicity. Therefore, a catalytic oxidation material having excellent performance for treating volatile organic compounds is urgently needed.

In addition, catalysts used for catalyzing hydrogenation of nitrobenzene in the prior art mainly include catalysts based on noble metals such as platinum (Pt), palladium (Pd), and rhodium (Rh), and catalysts based on non-noble metals such as copper (Cu), nickel (Ni), lead (Zn), and molybdenum (Mo). At present, Raney Ni catalysts are the most commonly used catalysts in industry for catalyzing the hydrogenation reduction of nitrobenzene compounds to produce aniline compounds, because of their low price and relatively high catalytic activity. However, Raney Ni catalysts still have many disadvantages, for example, framework nickel is very vulnerable to ignition in air and thus cannot be stored; hydrogen exists in the hydrogenation workshop, and thus explosion is easy to occur; the amount of reaction by-products is relatively large, the product yield is poor, the catalytic activity is relatively low and the like. Therefore, there is still a need for a catalytic material with high stability and catalytic activity that is suitable for catalyzing hydrogenation reduction reactions, especially nitrobenzene hydrogenation reactions.

It should be noted that the information disclosed in the above background section is only provided for the purpose of helping the understanding of the background of the present application, and therefore it may contain information that does not constitute a prior art known to a person of ordinary skill in the art.

SUMMARY OF THE INVENTION

To solve the problems in the prior art, the present application provides a nanocomposite material comprising carbon-coated transition metal particles having a core-shell structure, in which the transition metal nanoparticle core is tightly wrapped by a graphitized carbon shell layer, so that the loss of the transition metal in the core is reduced in usage, the stability of the material performance is better maintained, the safety of the material is ensured, and particularly, the material can also have a structure rich in mesopores, so that the mass transfer efficiency can be improved. Meanwhile, the present application also provides a simple, environmentally friendly and efficient method for preparing a carbon-coated transition metal nanocomposite material, in which a precursor of the target nanocomposite material can be obtained by simply mixing at normal pressure, and the preparation of the precursor can be carried out purely in water phase.

In one aspect, the present application provides a nanocomposite material comprising carbon-coated transition metal particles, the carbon-coated transition metal particles having a core-shell structure, the shell layer being a graphitized carbon layer doped with oxygen and/or nitrogen, and the core being a transition metal nanoparticle, wherein the nanocomposite material is a porous material having at least one distribution peak of mesopores.

Preferably, the nanocomposite material is a porous material having two or more distribution peaks of mesopores.

Preferably, the nanocomposite material has a loss on acid leaching of 40% or less, more preferably 30% or less, and particularly preferably 10% or less.

Preferably, the nanocomposite material further comprises an amorphous carbon matrix, the carbon-coated transition metal particles being dispersed in the amorphous carbon matrix; more preferably, the nanocomposite material is consisted of an amorphous carbon matrix and carbon-coated transition metal particles dispersed therein.

Preferably, the nanocomposite material has a proportion of mesopore volume to total pore volume of greater than about 50%, more preferably greater than about 80%, even more preferably greater than about 90%, particularly preferably greater than about 95%, and most preferably about 100%; more preferably, the mesopore volume of the nanocomposite material is between about 0.05 $cm^3/g$ and about 1.25 $cm^3/g$.

In another aspect, the present application provides a nanocomposite material comprising carbon-coated transition metal particles, the carbon-coated transition metal particles having a core-shell structure, the shell layer being a graphitized carbon layer doped with oxygen and/or nitrogen, and the core being a transition metal nanoparticle, wherein the nanocomposite material has a loss on acid leaching of no more than 10%.

Preferably, the nanocomposite material is a porous material having at least one distribution peak of mesopores, more preferably a porous material having two or more distribution peaks of mesopores.

Preferably, the nanocomposite material further comprises an amorphous carbon matrix, the carbon-coated transition metal particles being dispersed in the amorphous carbon matrix; more preferably, the nanocomposite material is consisted of an amorphous carbon matrix and carbon-coated transition metal particles dispersed therein.

Preferably, the nanocomposite material has a proportion of mesopore volume to total pore volume of greater than about 50%, more preferably greater than about 80%, even more preferably greater than about 90%, particularly preferably greater than about 95%, and most preferably about 100%; preferably, the mesopore volume of the nanocomposite material is between about 0.05 $cm^3/g$ and about 1.25 $cm^3/g$.

As compared with existing carbon-coated transition metal nanocomposite materials, the nanocomposite material according to the present application can provide one or more of the following advantages:

1) the nanocomposite material according to the present application has a tightly wrapped graphitized carbon layer/metal core-shell structure, and has no pore channel or defect that would allow access of a reactant to the transition metal core, so that the transition metal material in the core is very stable, not self-inflammable, resistant to acid corrosion, less hazardous, and easy for storage and transportation, thereby ensuring the security in use of the composite material.

2) the nanocomposite material according to the present application has a structure rich in mesopores, which is beneficial to mass transfer and diffusion of reactants and products during the reaction; the carbon material in the nanocomposite material has catalytic activity per se and can provide a synergetic effect with the transition metal, so that a higher mass transfer efficiency can be achieved; particularly, the nanocomposite material may have a multi-level mesoporous structure, thereby imparting more diverse properties to the material, making it suitable for more applications.

3) the nanocomposite material according to the present application comprises a strongly magnetic metal core wrapped by a graphitized carbon layer and has a highly porous structure, so that the nanocomposite material provides a better combination of magnetic separation function and adsorption function, and is particularly suitable for use in the field of adsorption separation.

4) the nanocomposite material according to the present application can be used as a catalyst for various organic reactions, and is beneficial to improving the catalytic efficiency for the reactions. When used for catalytic hydrogenation reaction, the material exhibits the advantages of good reproductivity, high activity, high selectivity and the like, and has good prospect of industrial application. When used as a catalytic oxidation catalyst, the material exhibits good low-temperature activity, which is of great significance for thoroughly removing volatile organic compounds present in industrial exhaust gases through catalytic combustion.

5) the nanocomposite material according to the present application is not self-inflammable in the air, and thus can be stored in the air for a long time like general goods, with no adverse impact on the service performance of the nanocomposite material in reactions such as catalytic oxidation, catalytic hydrogenation and the like.

6) in the preparation of the nanocomposite material according to the present application, the content of the doping element is adjustable, the oxygen element is not required to be introduced by means of nitric acid treatment or the like, and the electronic characteristic of the graphitized carbon layer can be adjusted, so that the nanocomposite material is suitable for catalyzing different reactions.

In yet another aspect, the present application provides a method for preparing a nanocomposite material comprising carbon-coated transition metal particles, comprising the steps of:

i) mixing a mixture comprising a transition metal source and a polybasic organic carboxylic acid with a solvent to form a homogeneous solution;

ii) removing the solvent from the homogeneous solution to obtain a precursor;

iii) subjecting the precursor to high-temperature pyrolysis under an inert protective atmosphere or a reducing atmosphere; and iv) optionally, subjecting the pyrolysis product obtained in step iii) to a treatment with a non-oxidizing strong acid.

Preferably, the mixture used in step i) of the method further comprises a nitrogen-containing organic compound and/or an oxygen-containing organic compound different from the polybasic organic carboxylic acid, wherein the nitrogen-containing organic compound is preferably one or more selected from the group consisting of urea, melamine, dicyanodiamine, hexamethylenetetramine and amino acids, and the oxygen-containing organic compound is preferably selected from polyols and organic carboxylic acids, such as lactic acid.

Preferably, the transition metal source is one or more selected from the group consisting of organic acid salts, carbonates, basic carbonates, oxides and hydroxides of transition metals; more preferably, the organic acid salt of the transition metal is a heteroatom-free organic carboxylate of the transition metal, such as acetate.

Further preferably, the polybasic organic carboxylic acid is one or more selected from the group consisting of citric acid, maleic acid, trimesic acid, terephthalic acid, malic acid, EDTA and dipicolinic acid.

Preferably, the non-oxidizing strong acid used in step iv) is one or more selected from the group consisting of hydrofluoric acid, hydrochloric acid, nitric acid and sulfuric acid, more preferably hydrochloric acid and/or sulfuric acid.

As compared with existing methods for preparing carbon-coated transition metal nanocomposite materials, the method according to the present application can provide one or more of the following advantages:

1) the method according to the present application is simpler and more efficient, as the precursor subjected to high-temperature pyrolysis directly obtained by mixing a transition metal source and a polybasic organic carboxylic acid uniformly in a solvent (e.g. water), and the atom utilization of the transition metal in the precursor can be 100%.

2) the method according to the present application can provide a better covering effect, and overcome the following defects of the prior art for preparing the precursor having a metallic organic framework structure, i.e. the need for a high-temperature and high-pressure reaction kettle in the self-assembly reaction, the waste of a large amount of organic solvent, the complexity in purification and the like. As compared with the sol-gel method, in the method according to the present application, no high-molecular auxiliary agent is needed, and the reaction steps can be simplified.

4) in the nanocomposite material prepared by the method according to the present application, the nano metal particles are wrapped more tightly by the graphitized carbon layer, so that the nanocomposite material can be used under harsher conditions.

5) in the method according to the present application, the content of the doping element in the graphitized carbon layer is adjustable, the oxygen element is not required to be introduced by means of nitric acid treatment or the like, the electronic characteristic of the graphitized carbon layer can be adjusted, so that the nanocomposite material obtained is suitable for catalyzing different reactions.

In yet another aspect, the present application provides a nanocomposite material comprising carbon-coated transition metal particles prepared by the method according to the present application.

In a further aspect, the present application provides the use of the nanocomposite material according to the present application as a catalyst in the treatment of volatile organic compounds and in a hydrogenation reduction reaction.

Preferably, said use in the treatment of volatile organic compounds comprises: contacting a volatile organic compound with the nanocomposite material to conduct a catalytic oxidation reaction.

Preferably, said use in a hydrogenation reduction reaction comprises use in a reaction selected from the group consisting of: the hydrogenation reaction of p-chloronitrobenzene for producing p-chloroaniline, the hydrogenation reaction of nitrobenzene for producing aniline, the hydrogenation reaction of nitrophenol for producing aminophenol, the hydrogenation reaction of p-nitroanisole for producing p-anisidine, the hydrogenation reaction of phenol for producing cyclohexanol, the hydrogenation reaction of olefins, the hydrogenation reaction of aromatic hydrocarbons for producing cyclohexane derivatives, the hydrogenation reaction of aldehydes for producing alcohols, and the hydrogenation reaction of ketones for producing alcohols.

BRIEF DESCRIPTION OF THE DRAWINGS

The drawings, forming a part of the present description, are provided to help the understanding of the present application, and should not be considered to be limiting. The present application can be interpreted with reference to the drawings in combination with the detailed description hereinbelow. In the drawings:

Part I

FIG. 1-2 shows a photograph of the magnetic test of the carbon-coated nickel nanocomposite material obtained in Example 1-1.

FIG. 1-3 shows a Transmission Electron Microscope (TEM) image of the carbon-coated nickel nanocomposite material obtained in Example 1-1.

FIG. 1-4 shows an XRD pattern of the carbon-coated nickel nanocomposite material obtained in Example 1-1.

FIG. 1-5A is a diagram showing the $N_2$ adsorption-desorption isotherm of the carbon-coated nickel nanocomposite material obtained in Example 1-1.

FIG. 1-5B is a diagram showing the pore-size distribution curve of the carbon-coated nickel nanocomposite material obtained in Example 1-1.

FIG. 1-6 shows a TEM image of the carbon-coated nickel nanocomposite material obtained in Example 1-2.

FIG. 1-7 shows an XRD pattern of the carbon-coated nickel nanocomposite material obtained in Example 1-2.

FIG. 1-8 is a diagram showing the pore-size distribution curve of the carbon-coated nickel nanocomposite material obtained in Example 1-2.

FIG. 1-9 shows a TEM image of the carbon-coated cobalt nanocomposite material obtained in Example 1-3.

FIG. 1-10 shows an XRD pattern of the carbon-coated cobalt nanocomposite material obtained in Example 1-3.

FIG. 1-11 is a diagram showing the pore-size distribution curve of the carbon-coated cobalt nanocomposite material obtained in Example 1-3.

FIG. 1-12 shows a TEM image of the carbon-coated nickel nanocomposite material obtained in Example 1-4.

FIG. 1-13 shows a TEM image of the carbon-coated nickel nanocomposite material obtained in Example 1-5.

FIG. 1-14 shows a TEM image of the carbon-coated nickel-cobalt nanocomposite material obtained in Example 1-6.

FIG. 1-15 shows an XRD pattern of the carbon-coated nickel-cobalt nanocomposite material obtained in Example 1-6.

FIG. 1-16 is a diagram showing the pore-size distribution curve of the carbon-coated nickel-cobalt nanocomposite material obtained in Example 1-6.

FIG. 1-17 shows a TEM image of the carbon-coated nickel nanocomposite material obtained in Example 1-7.

FIG. 1-18 shows an XRD pattern of the carbon-coated nickel nanocomposite material obtained in Example 1-7.

FIG. 1-19 is a diagram showing the pore-size distribution curve of the carbon-coated nickel nanocomposite material obtained in Example 1-7.

FIG. 1-20 shows a TEM image of the carbon-coated nickel nanocomposite material obtained in Example 1-8.

FIG. 1-21 shows an XRD pattern of the carbon-coated nickel nanocomposite material obtained in Example 1-8.

FIG. 1-22 shows a TEM image of the carbon-coated nickel nanocomposite material obtained in Example 1-9.

FIG. 1-23 shows an XRD pattern of the carbon-coated nickel nanocomposite material obtained in Example 1-9.

FIG. 1-24 shows a photograph of the magnetic test of the carbon-coated nickel nanocomposite material obtained in Example 1-10.

FIG. 1-25 shows a TEM image of the carbon-coated nickel nanocomposite material obtained in Example 1-10.

FIG. 1-26 shows an XRD pattern of the carbon-coated nickel nanocomposite material obtained in Example 1-10.

FIG. 1-27 is a diagram showing the pore-size distribution curve of the carbon-coated nickel nanocomposite material obtained in Example 1-10.

FIG. 1-28 shows an XRD pattern of the nanocomposite material obtained in Comparative Example 1-4.

Part II

Figure 1:
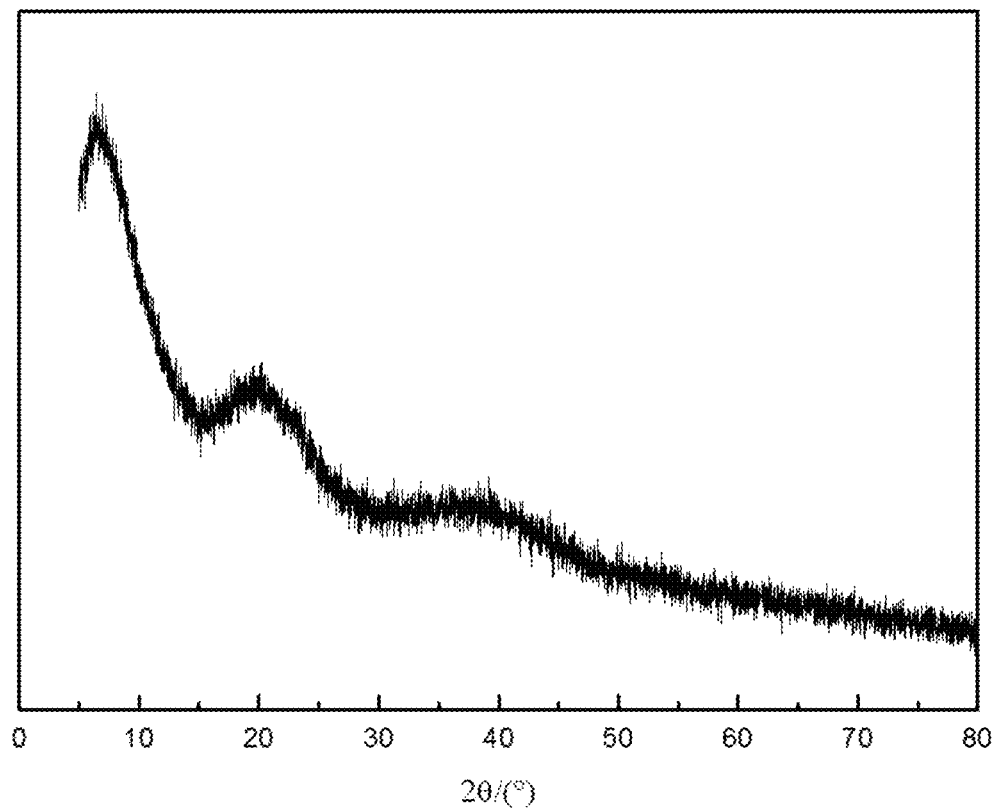
FIG. 1-1 shows an X-ray diffraction (XRD) pattern of the precursor obtained in Example 1-1.
Figures 1, 2:
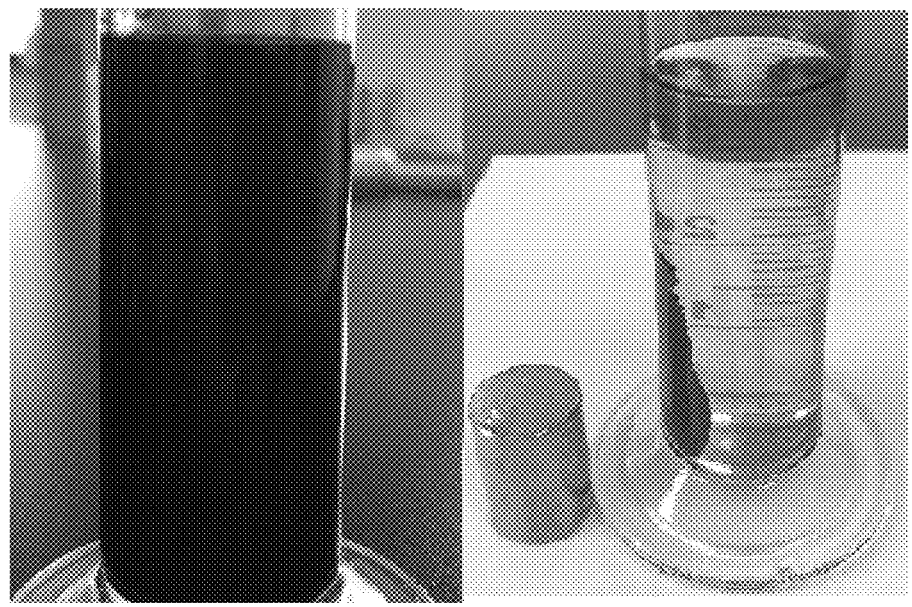

FIG. 2-1 is a photograph of the magnetic test of the carbon-coated nickel nanocomposite material obtained in Example 2-1.

FIG. 2-2 is a TEM image of the carbon-coated nickel nanocomposite material obtained in Example 2-1.

Figures 1, 2, 3:
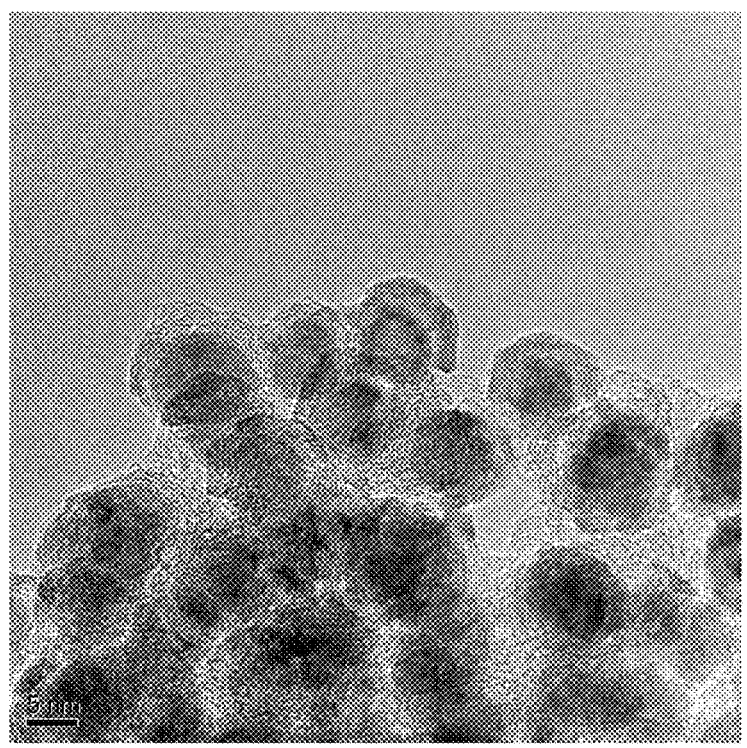

FIG. 2-3 shows an XRD pattern of the carbon-coated nickel nanocomposite material obtained in Example 2-1.

FIG. 2-4A is a diagram showing the $N_2$ adsorption-desorption isotherm of the carbon-coated nickel nanocomposite material obtained in Example 2-1.

FIG. 2-4B is a diagram showing the pore-size distribution curve of the carbon-coated nickel nanocomposite material obtained in Example 2-1.

FIG. 2-5 shows a TEM image of the carbon-coated nickel nanocomposite material obtained in Example 2-2.

FIG. 2-6 shows an XRD pattern of the carbon-coated nickel nanocomposite material obtained in Example 2-2.

FIG. 2-7 is a diagram showing the pore-size distribution curve of the carbon-coated nickel nanocomposite material obtained in Example 2-2.

FIG. 2-8 shows a TEM image of the carbon-coated cobalt nanocomposite material obtained in Example 2-3.

FIG. 2-9 shows an XRD pattern of the carbon-coated cobalt nanocomposite material obtained in Example 2-3.

FIG. 2-10 is a diagram showing the pore-size distribution curve of the carbon-coated cobalt nanocomposite material obtained in Example 2-3.

FIG. 2-11 shows an XRD pattern of the precursor obtained in Example 2-1.

FIG. 2-12 shows a TEM image of the carbon-coated nickel-cobalt nanocomposite material obtained in Example 2-4.

FIG. 2-13 shows an XRD pattern of the carbon-coated nickel-cobalt nanocomposite material obtained in Example 2-4.

FIG. 2-14 is a diagram showing the pore-size distribution curve of the carbon-coated nickel-cobalt nanocomposite material obtained in Example 2-4.

FIG. 2-15 shows a TEM image of the carbon-coated nickel nanocomposite material obtained in Example 2-5.

FIG. 2-16 shows an XRD pattern of the carbon-coated nickel nanocomposite material obtained in Example 2-5.

FIG. 2-17 shows a TEM image of the carbon-coated nickel nanocomposite material obtained in Example 2-6.

FIG. 2-18 shows an XRD pattern of the carbon-coated nickel nanocomposite material obtained in Example 2-6.

FIG. 2-19 shows a TEM image of the carbon-coated nickel nanocomposite material obtained in Example 2-7.

FIG. 2-20 shows an XRD pattern of the carbon-coated nickel nanocomposite material obtained in Example 2-7.

FIG. 2-21 shows a TEM image of the carbon-coated nickel nanocomposite material obtained in Example 2-8.

FIG. 2-22 shows an XRD pattern of the carbon-coated nickel nanocomposite material obtained in Example 2-8.

FIG. 2-23 is a diagram showing the pore-size distribution curve of the carbon-coated nickel nanocomposite material obtained in Example 2-8.

FIG. 2-24 shows a TEM image of the carbon-coated nickel nanocomposite material obtained in Example 2-9.

FIG. 2-25 shows an XRD pattern of the carbon-coated nickel nanocomposite material obtained in Example 2-9.

FIG. 2-26 is a diagram showing the pore-size distribution curve of the carbon-coated nickel nanocomposite material obtained in Example 2-9.

FIG. 2-27 shows a photograph of the magnetic test of the carbon-coated nickel nanocomposite material obtained in Example 2-10.

FIG. 2-28 shows a TEM image of the carbon-coated nickel nanocomposite material obtained in Example 2-10.

FIG. 2-29 shows an XRD pattern of the carbon-coated nickel nanocomposite material obtained in Example 2-10.

FIG. 2-30 is a diagram showing the pore-size distribution curve of the carbon-coated nickel nanocomposite material obtained in Example 2-10.

Part III

FIG. 3-1 shows an XRD pattern of the carbon-coated nickel nanocomposite material P2 obtained in Example 3-1.

Figures 1, 3:
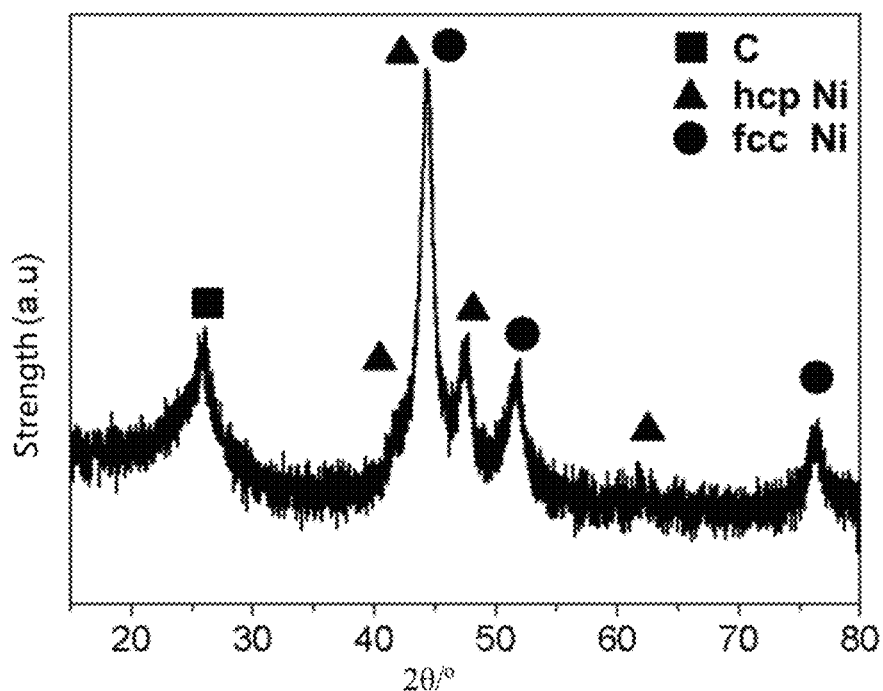
Figures 2A, 3:
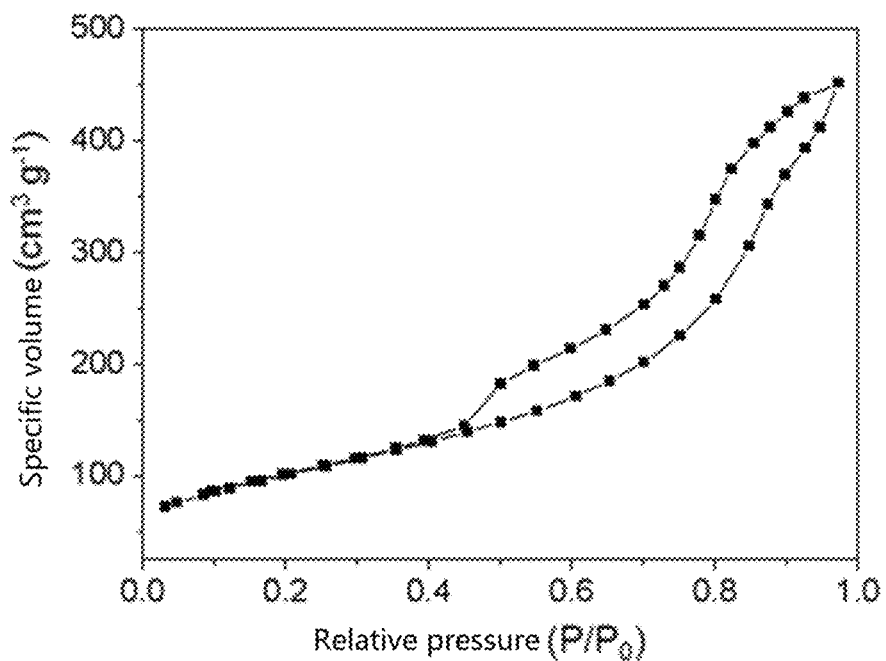

FIG. 3-2A is a diagram showing the $N_2$ adsorption-desorption isotherm of the carbon-coated nickel nanocomposite material P2 obtained in Example 3-1.

Figures 2B, 3:
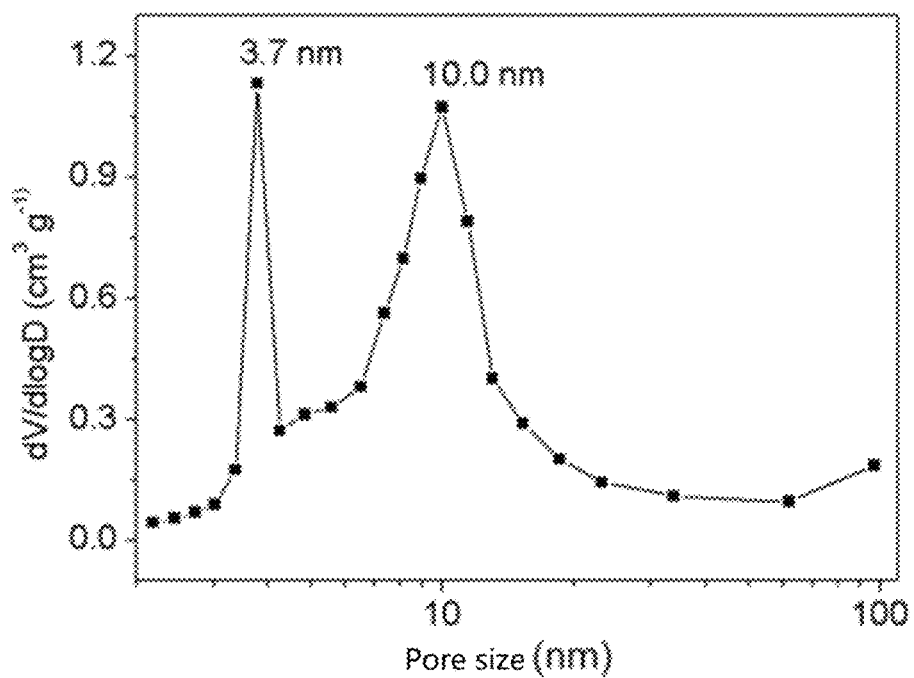
Figure 3:
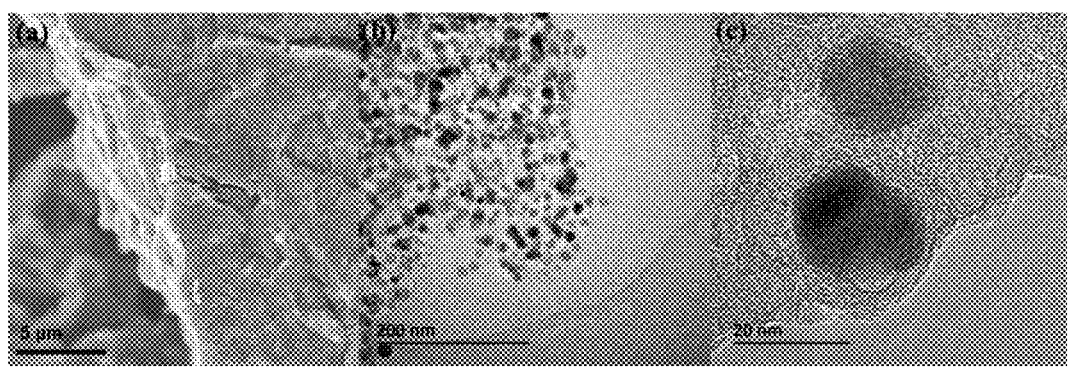
Figures 3, 4:
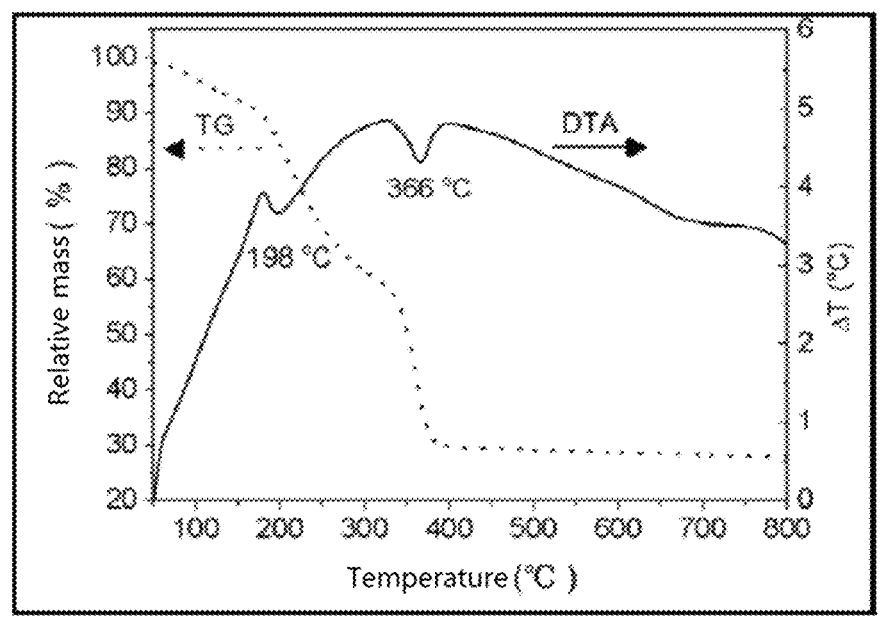
Figures 3, 4, 5:
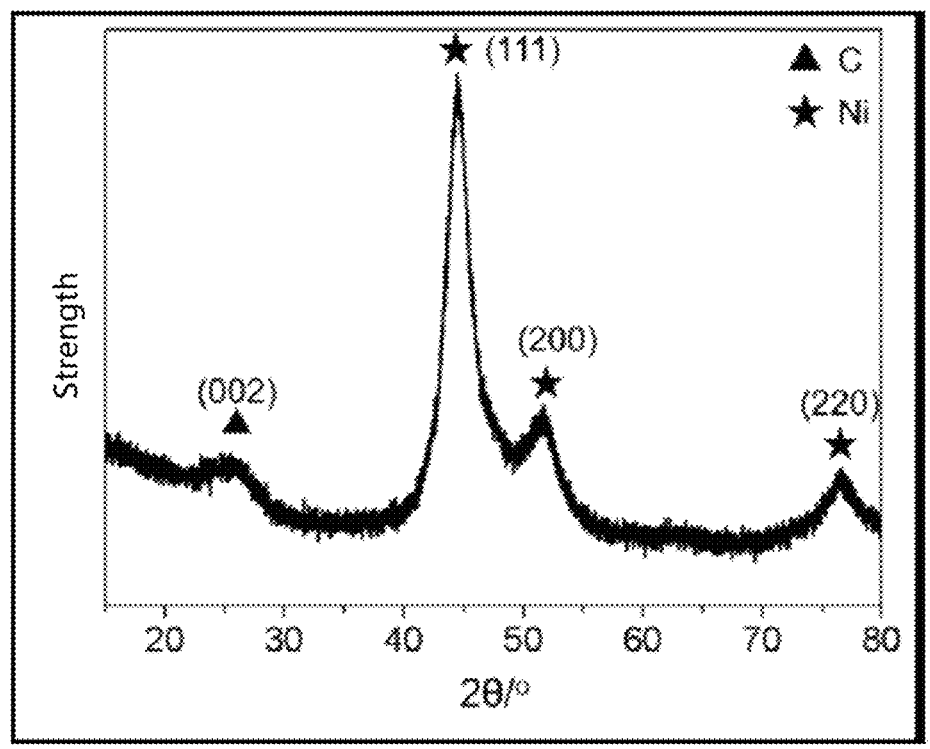
Figures 3, 4, 5, 6:
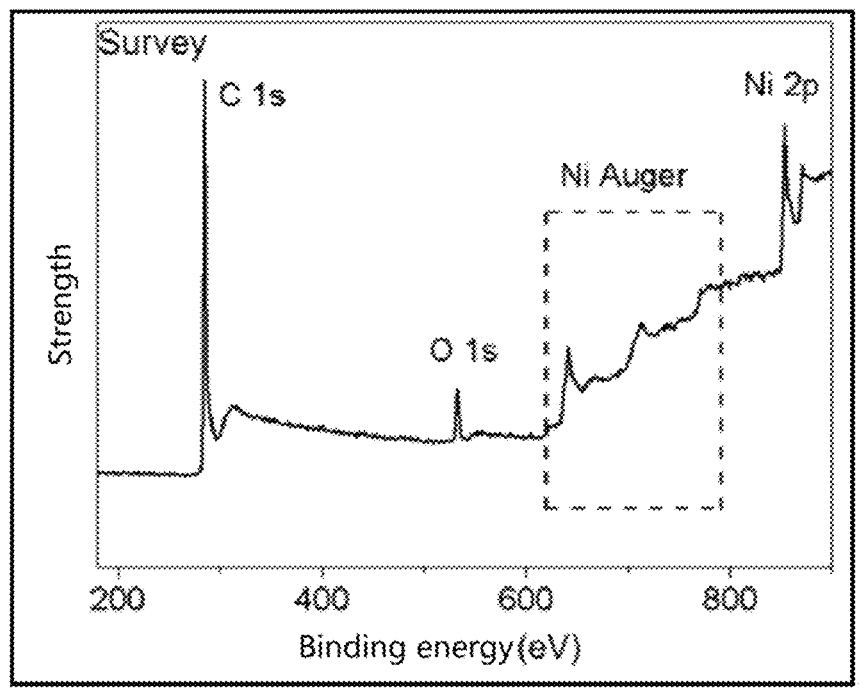
Figures 3, 4, 5, 6, 7, 7A:
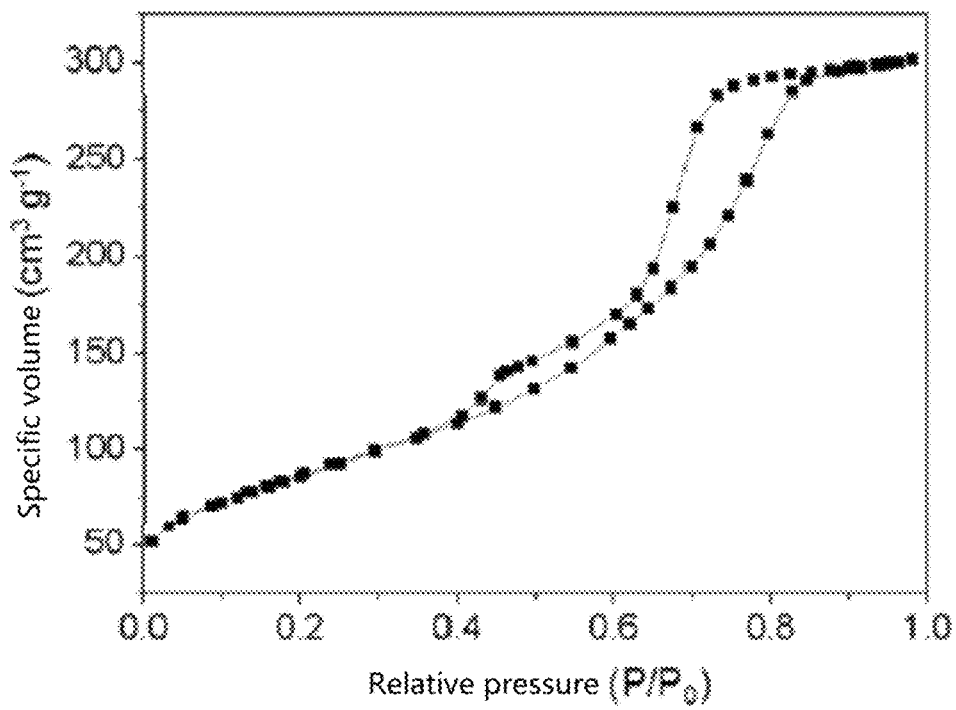
Figures 3, 4, 5, 6, 7, 7B:
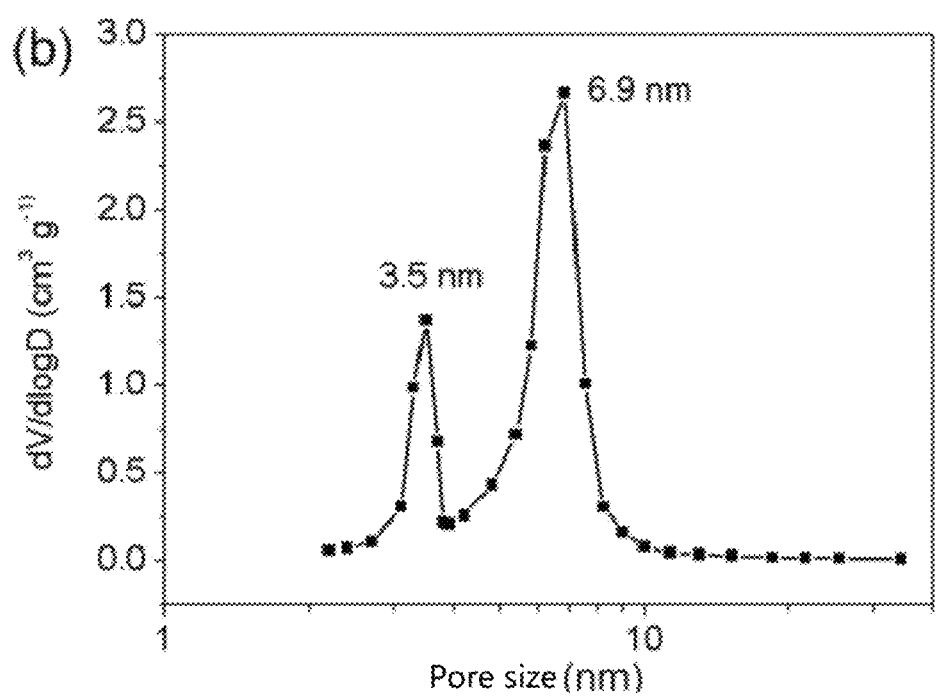

FIG. 3-2B is a diagram showing the pore-size distribution curve of the carbon-coated nickel nanocomposite material P2 obtained in Example 3-1.

FIG. 3-3 shows Scanning Electron Microscope (SEM) and Transmission Electron Microscope (TEM) images of the carbon-coated nickel nanocomposite material P2 obtained in Example 3-1.

Figures 1, 2, 3, 4:
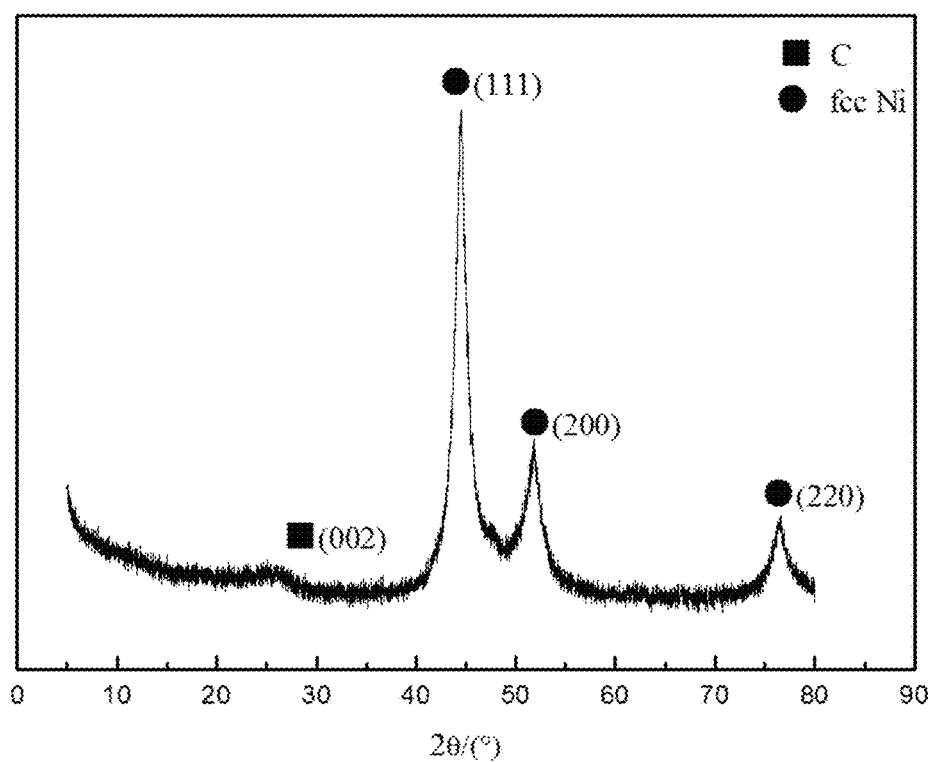

FIG. 3-4 is a diagram showing the Thermogravimetric-Differential Thermal Analysis curve (TG-DTA) of the precursor obtained in Example 3-2.

Figures 1, 2, 3, 4, 5, 5A:
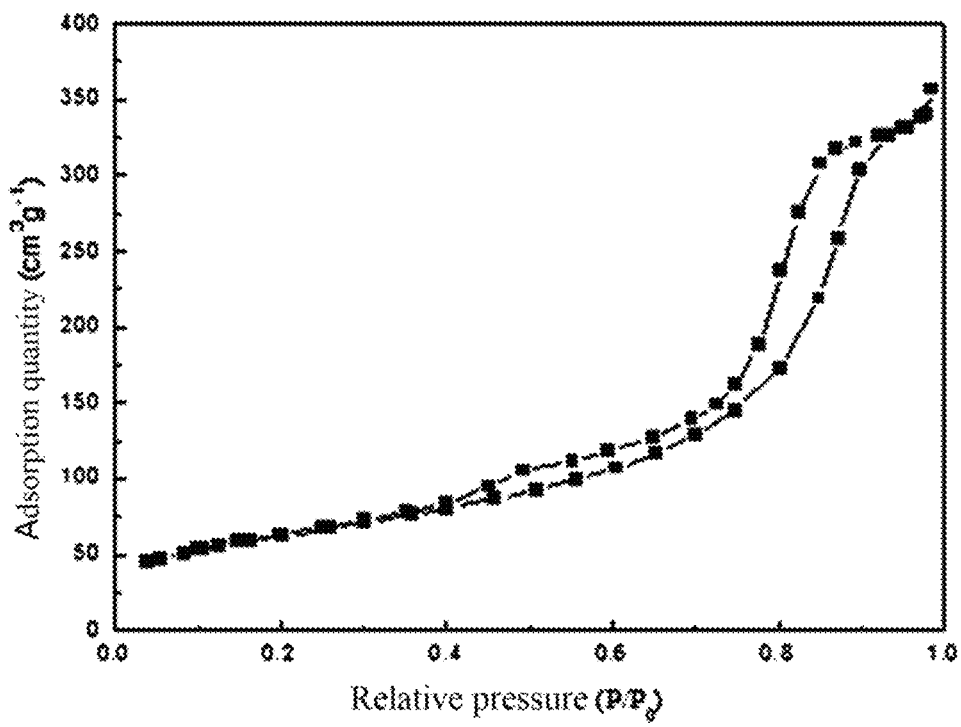
Figures 1, 2, 3, 4, 5, 5B:
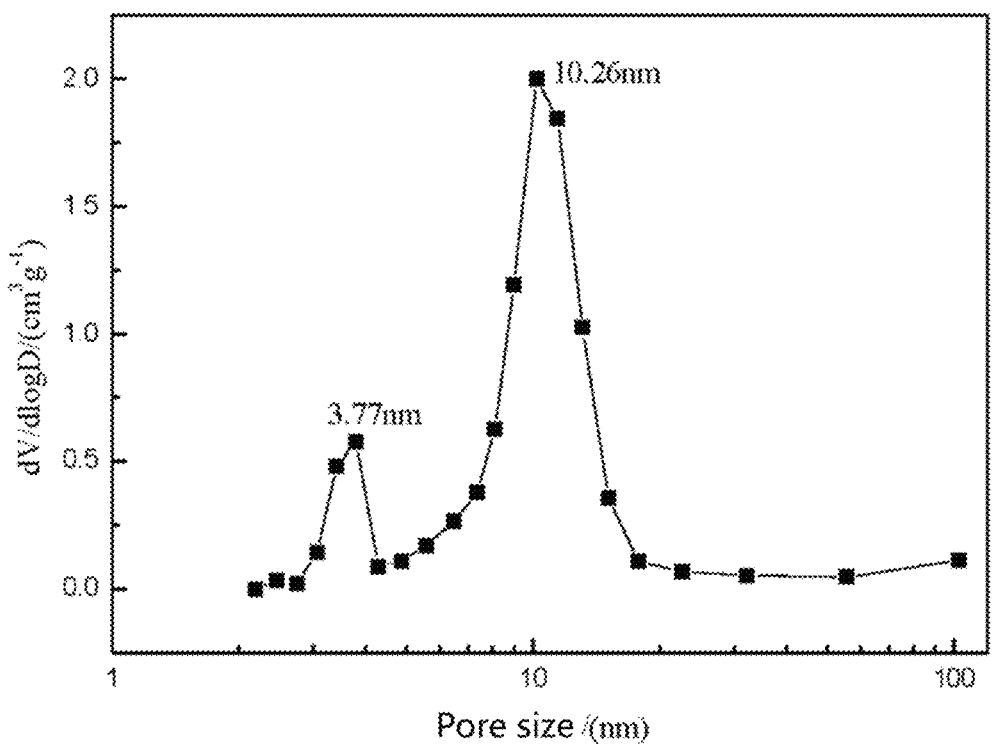
Figures 1, 2, 3, 4, 5, 6:
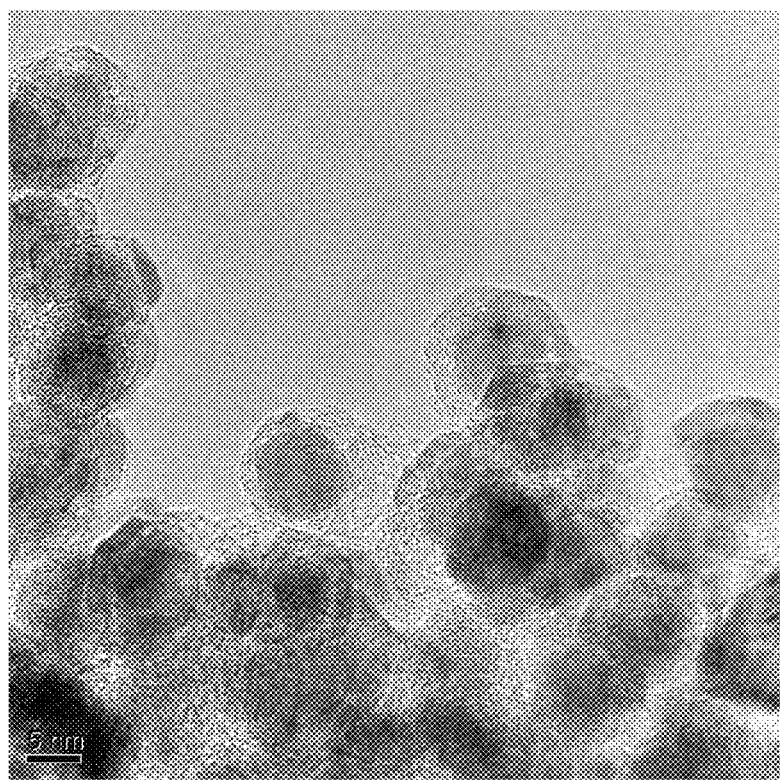
Figures 1, 2, 3, 4, 5, 6, 7:
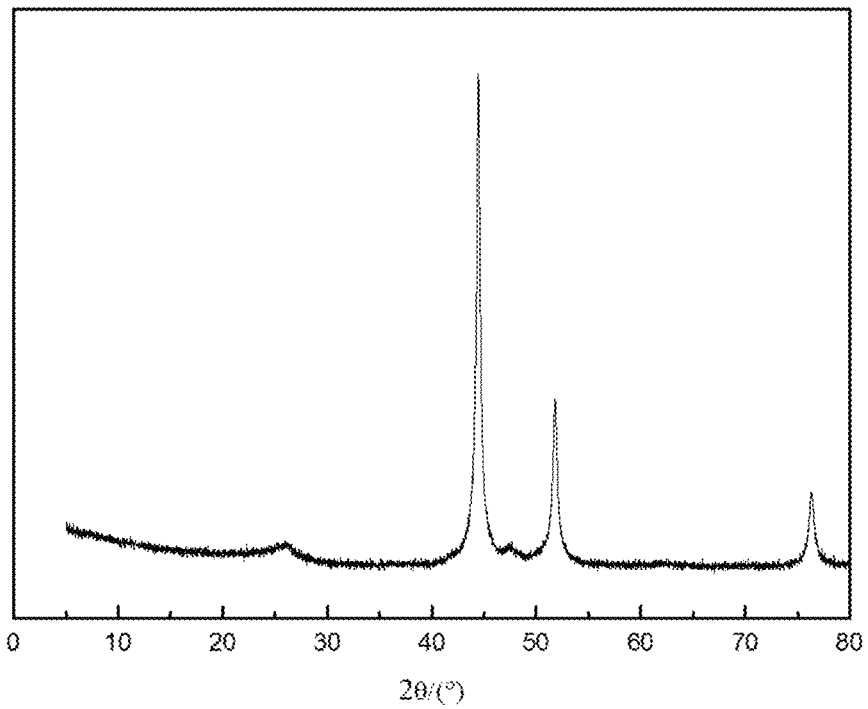
Figures 1, 2, 3, 4, 5, 6, 7, 8:
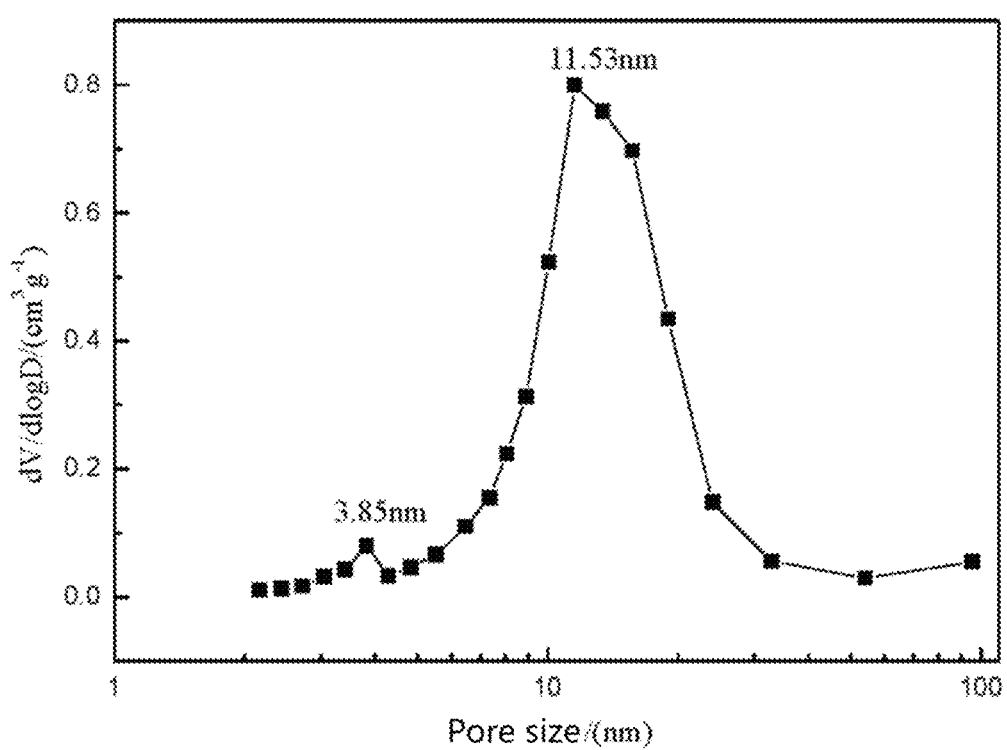
Figures 1, 2, 3, 4, 5, 6, 7, 8, 9:
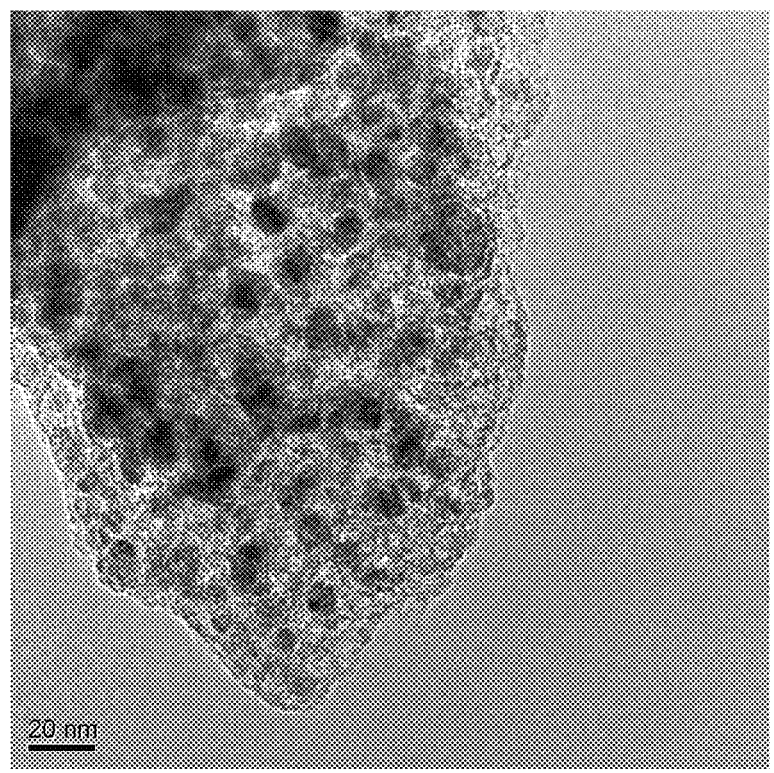
Figures 1, 2, 3, 4, 5, 6, 7, 8, 9, 10:
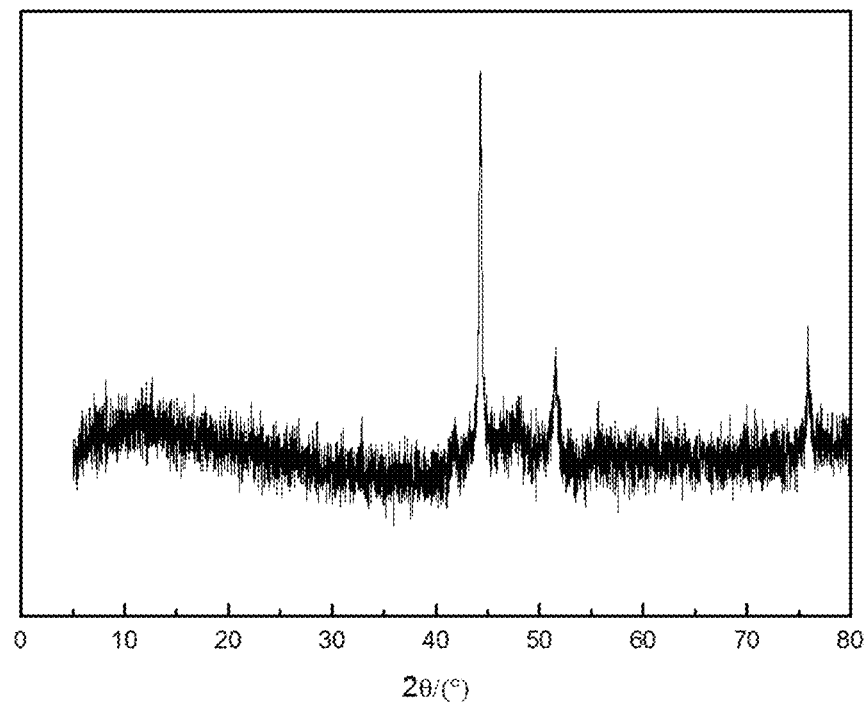
Figures 1, 2, 3, 4, 5, 6, 7, 8, 9, 10, 11:
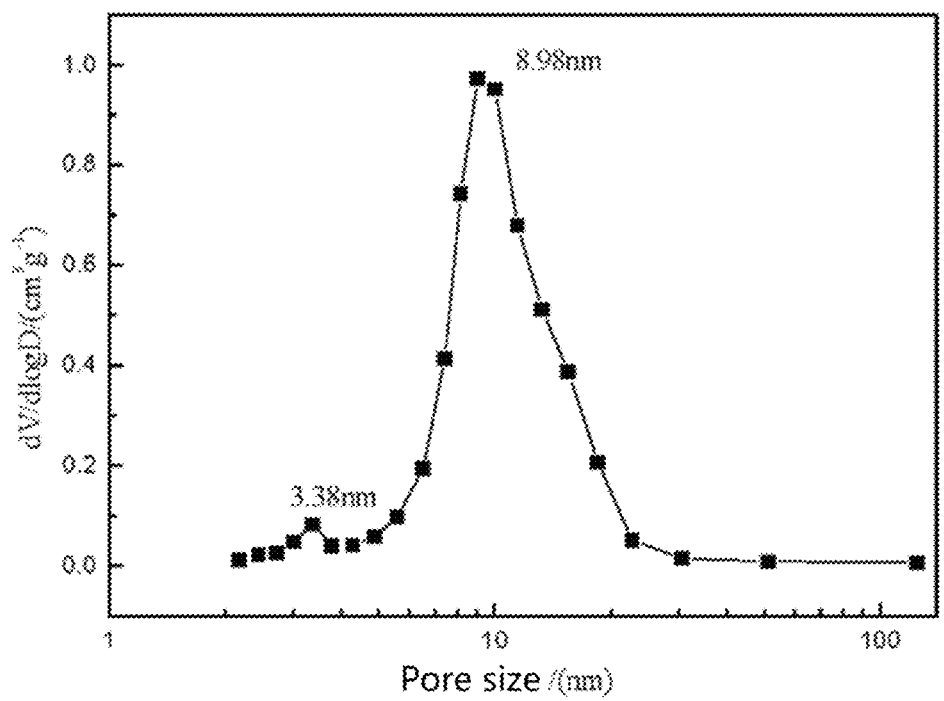
Figures 1, 2, 3, 4, 5, 6, 7, 8, 9, 10, 11, 12:
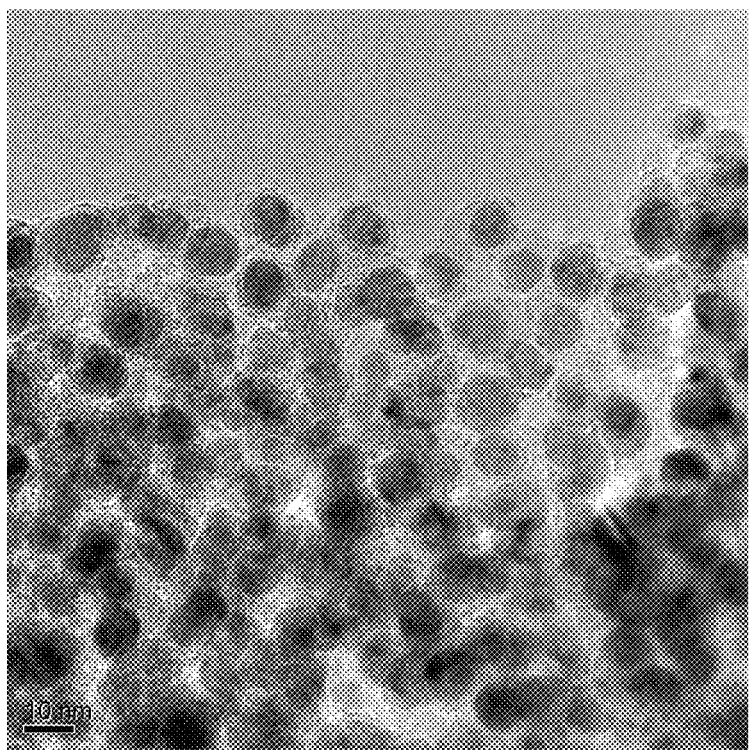
Figures 1, 2, 3, 4, 5, 6, 7, 8, 9, 10, 11, 12, 13:
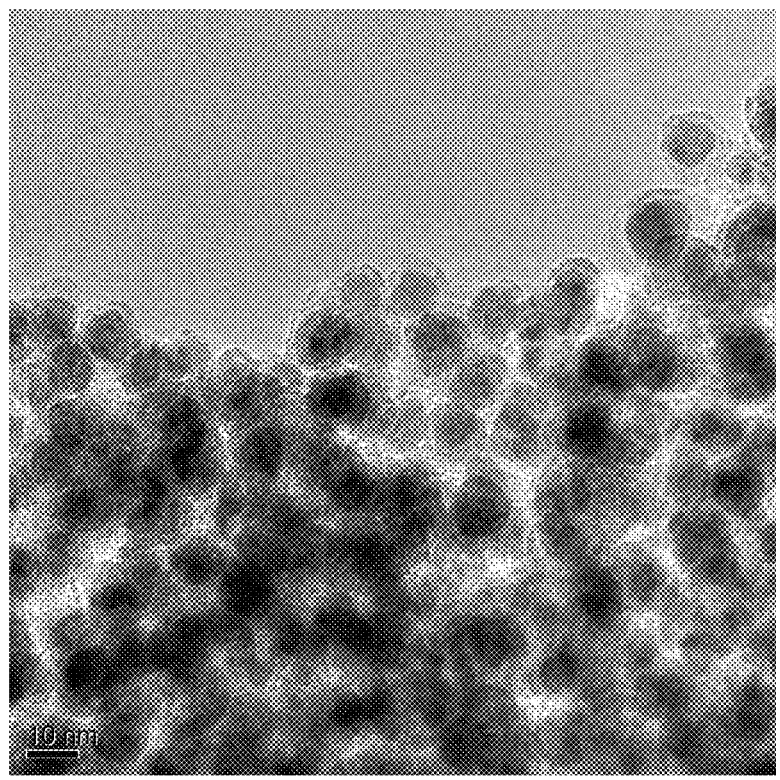
Figures 1, 2, 3, 4, 5, 6, 7, 8, 9, 10, 11, 12, 13, 14:
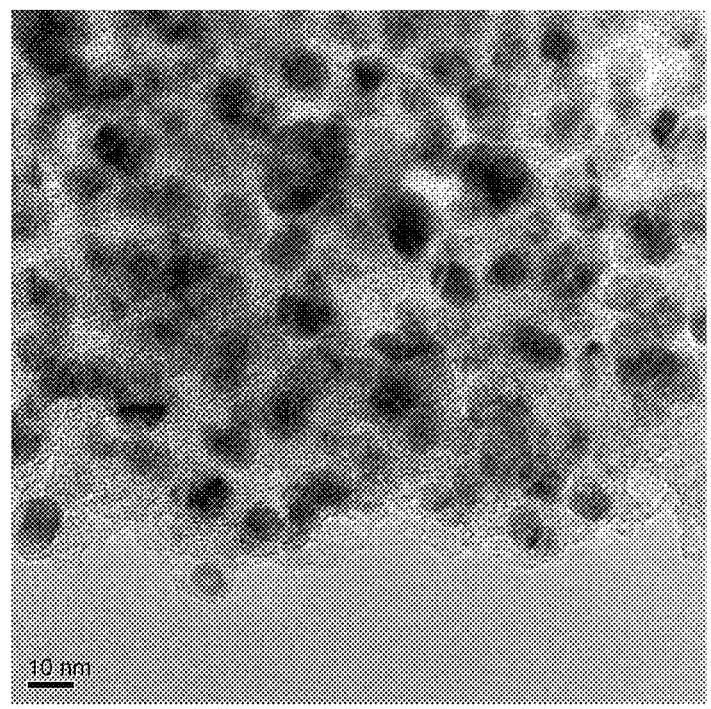
Figures 1, 2, 3, 4, 5, 6, 7, 8, 9, 10, 11, 12, 13, 14, 15:
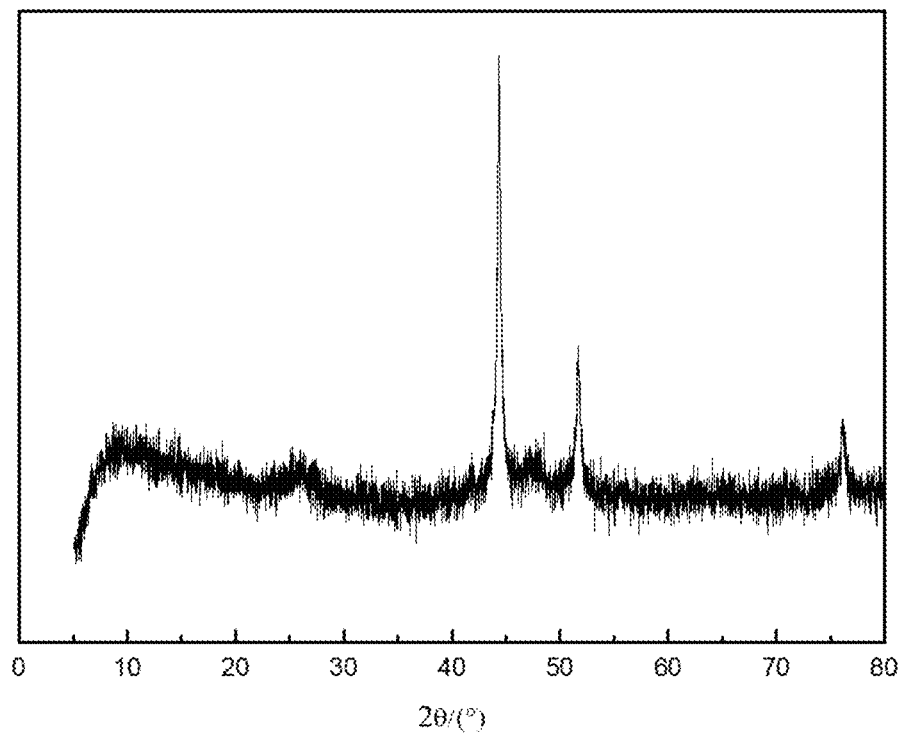
Figures 1, 2, 3, 4, 5, 6, 7, 8, 9, 10, 11, 12, 13, 14, 15, 16:
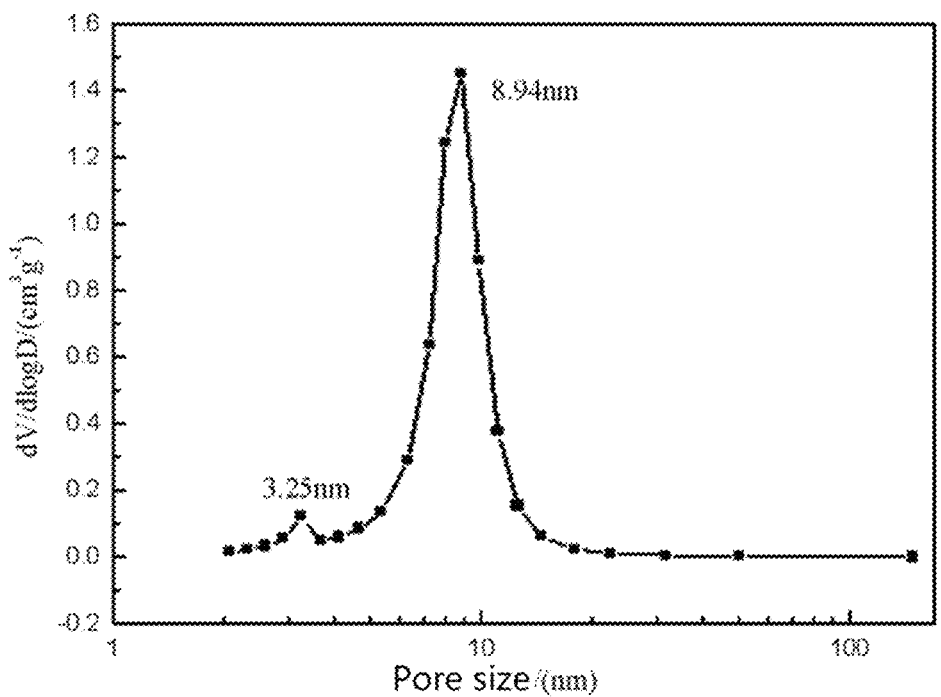
Figures 1, 2, 3, 4, 5, 6, 7, 8, 9, 10, 11, 12, 13, 14, 15, 16, 17:
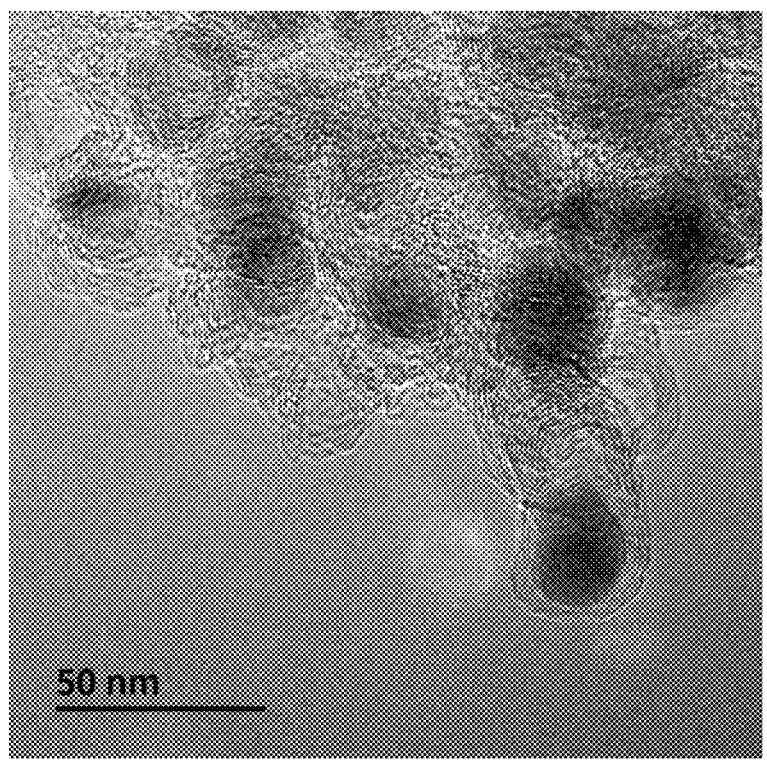
Figures 1, 2, 3, 4, 5, 6, 7, 8, 9, 10, 11, 12, 13, 14, 15, 16, 17, 18:
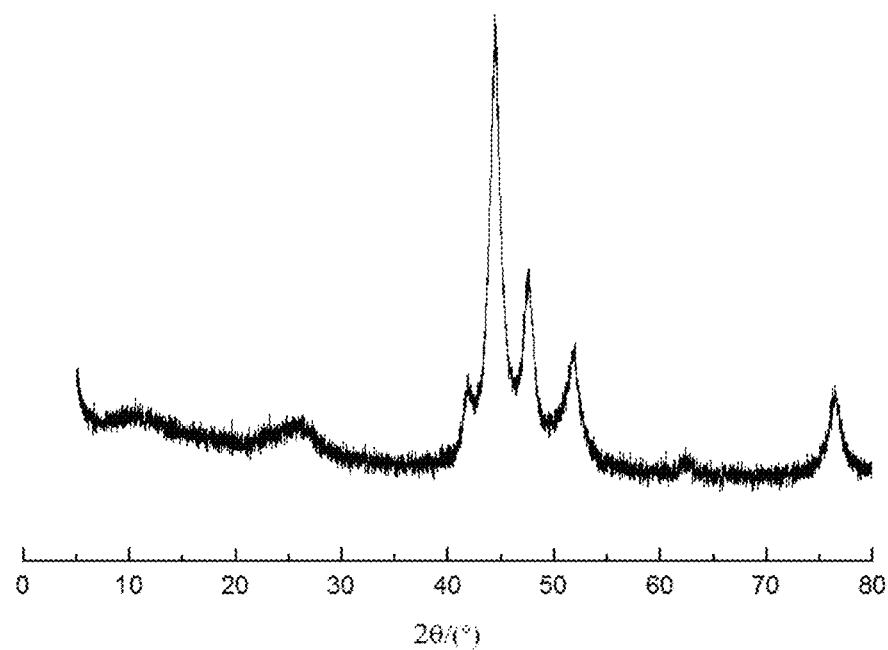
Figures 1, 2, 3, 4, 5, 6, 7, 8, 9, 10, 11, 12, 13, 14, 15, 16, 17, 18, 19:
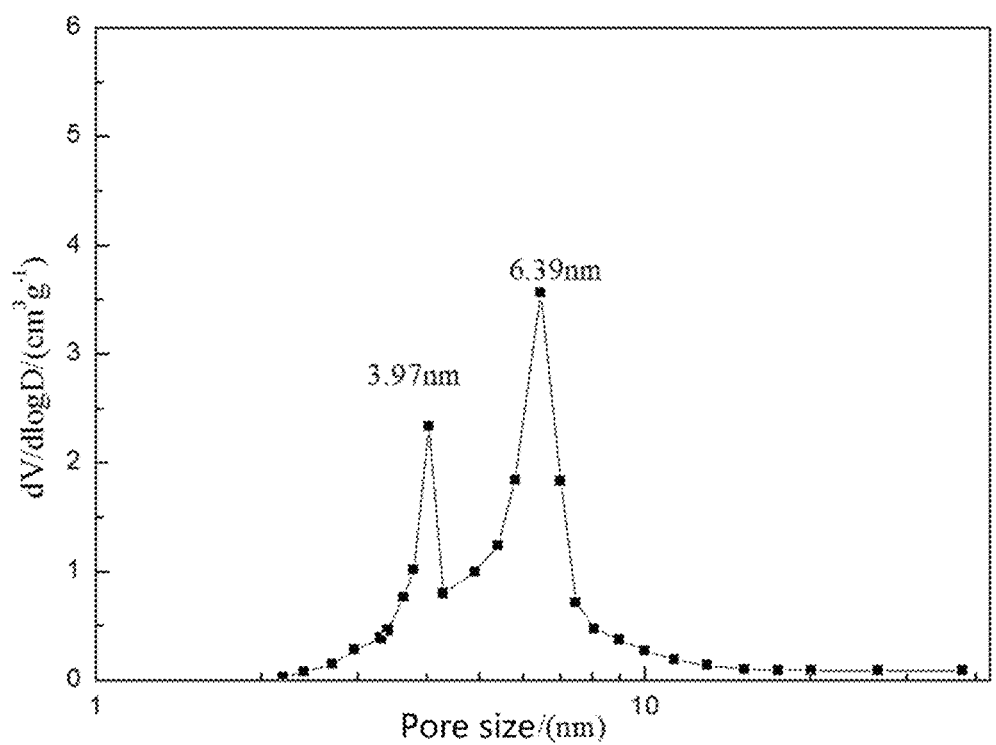
Figures 1, 2, 3, 4, 5, 6, 7, 8, 9, 10, 11, 12, 13, 14, 15, 16, 17, 18, 19, 20:
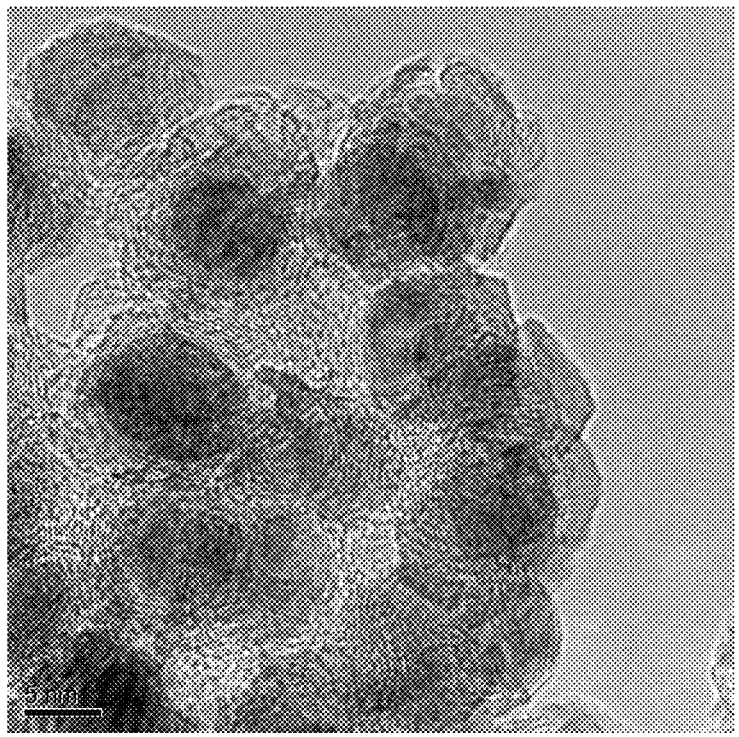
Figures 1, 2, 3, 4, 5, 6, 7, 8, 9, 10, 11, 12, 13, 14, 15, 16, 17, 18, 19, 20, 21:
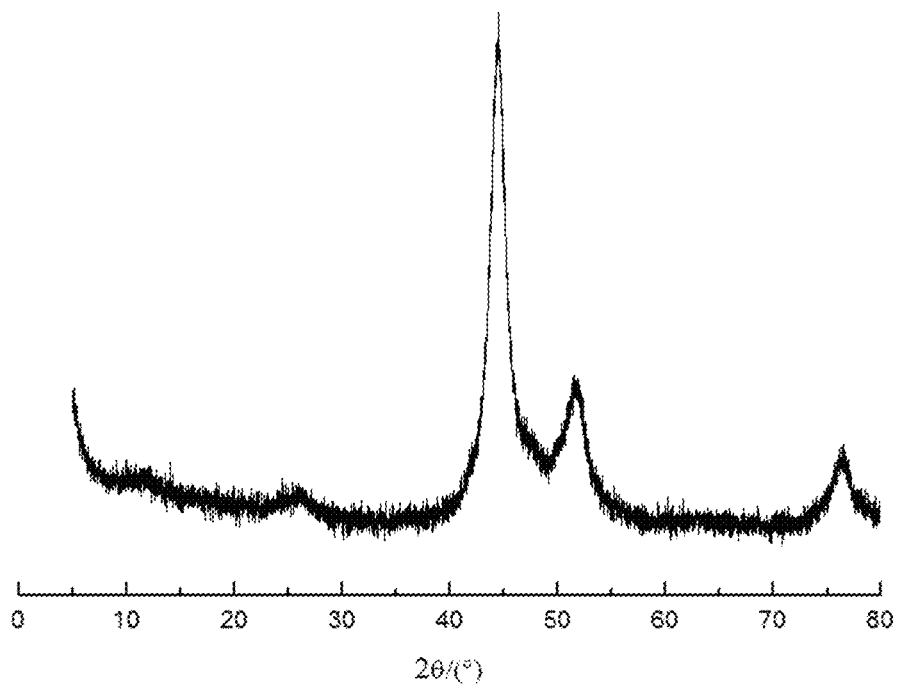
Figures 1, 2, 3, 4, 5, 6, 7, 8, 9, 10, 11, 12, 13, 14, 15, 16, 17, 18, 19, 20, 21, 22:
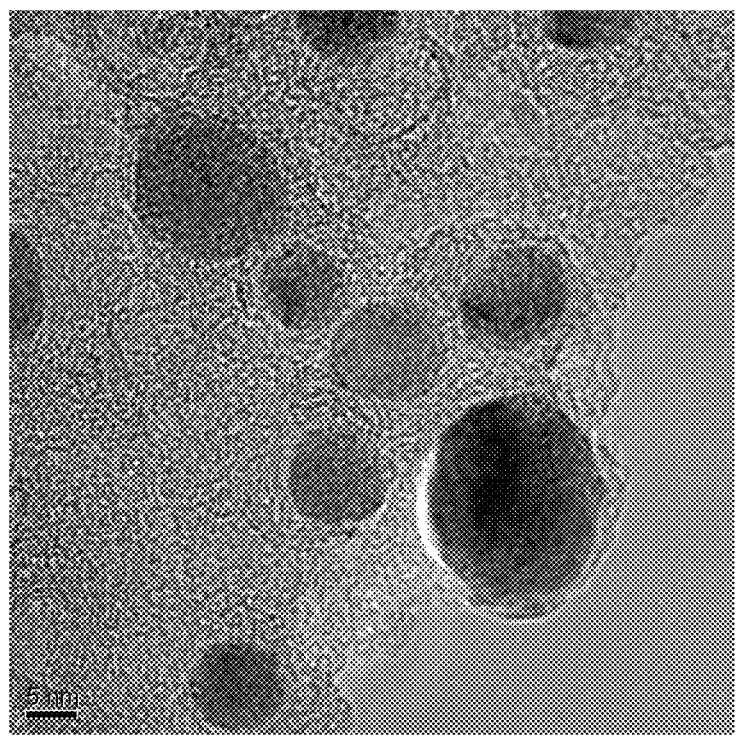
Figures 1, 2, 3, 4, 5, 6, 7, 8, 9, 10, 11, 12, 13, 14, 15, 16, 17, 18, 19, 20, 21, 22, 23:
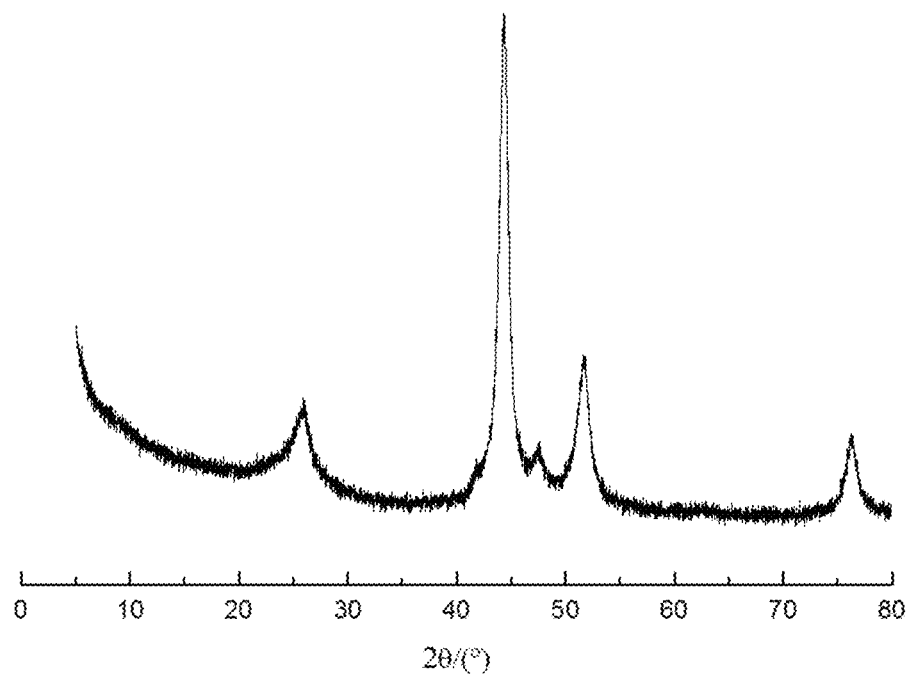
Figures 1, 2, 3, 4, 5, 6, 7, 8, 9, 10, 11, 12, 13, 14, 15, 16, 17, 18, 19, 20, 21, 22, 23, 24:
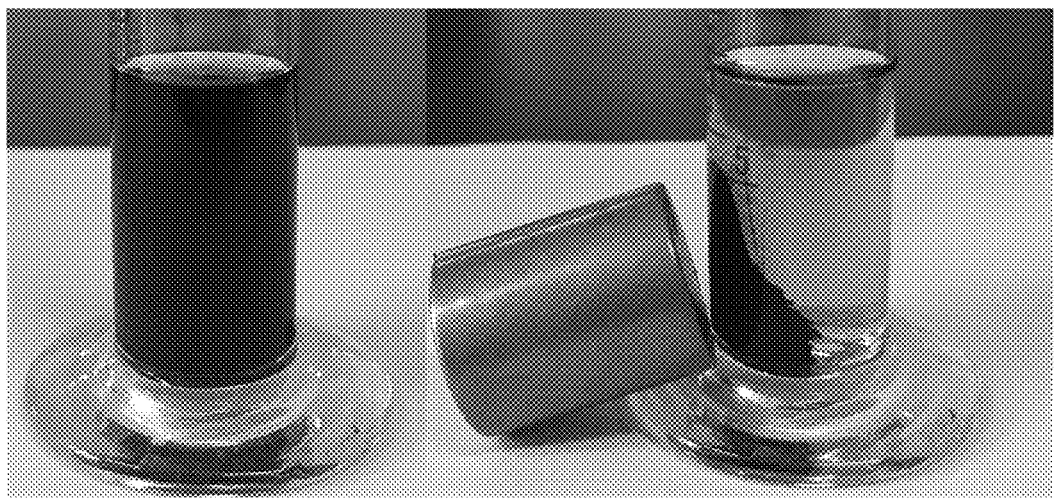
Figures 1, 2, 3, 4, 5, 6, 7, 8, 9, 10, 11, 12, 13, 14, 15, 16, 17, 18, 19, 20, 21, 22, 23, 24, 25:
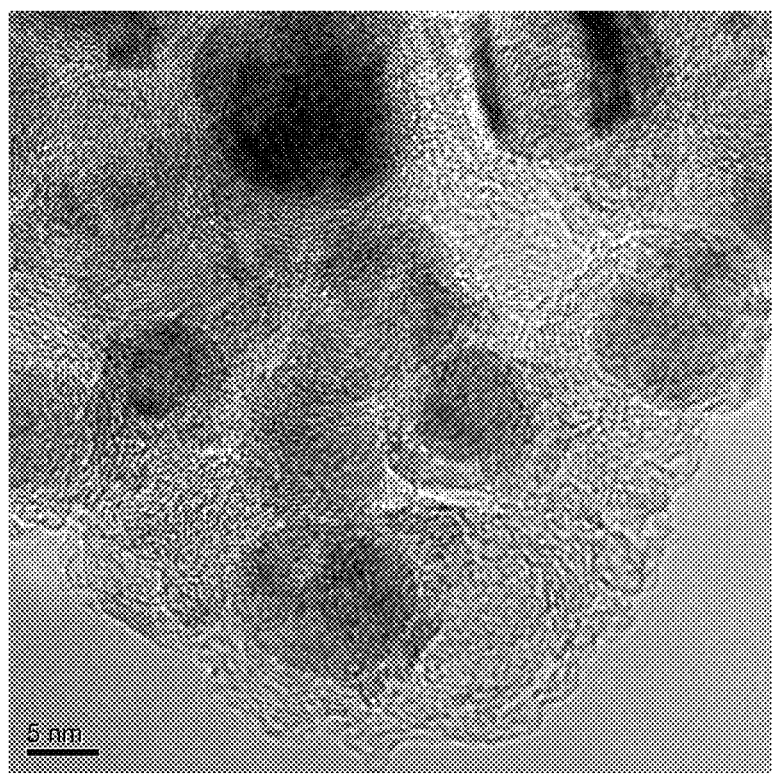
Figures 1, 2, 3, 4, 5, 6, 7, 8, 9, 10, 11, 12, 13, 14, 15, 16, 17, 18, 19, 20, 21, 22, 23, 24, 25, 26:
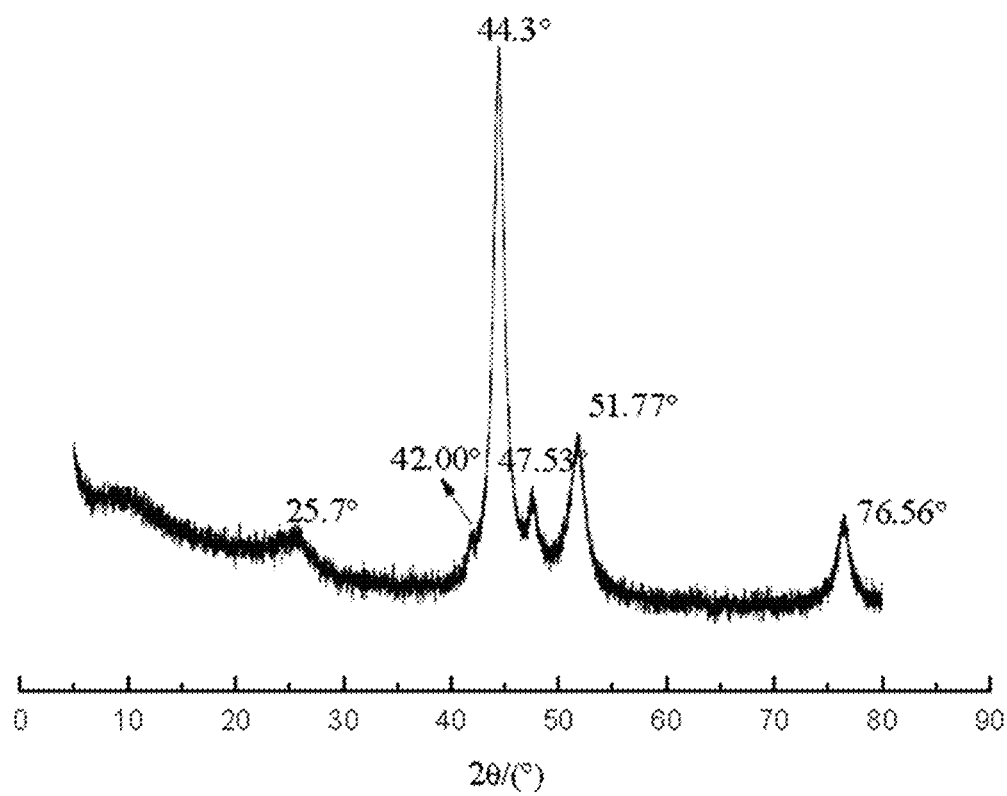
Figures 1, 2, 3, 4, 5, 6, 7, 8, 9, 10, 11, 12, 13, 14, 15, 16, 17, 18, 19, 20, 21, 22, 23, 24, 25, 26, 27:
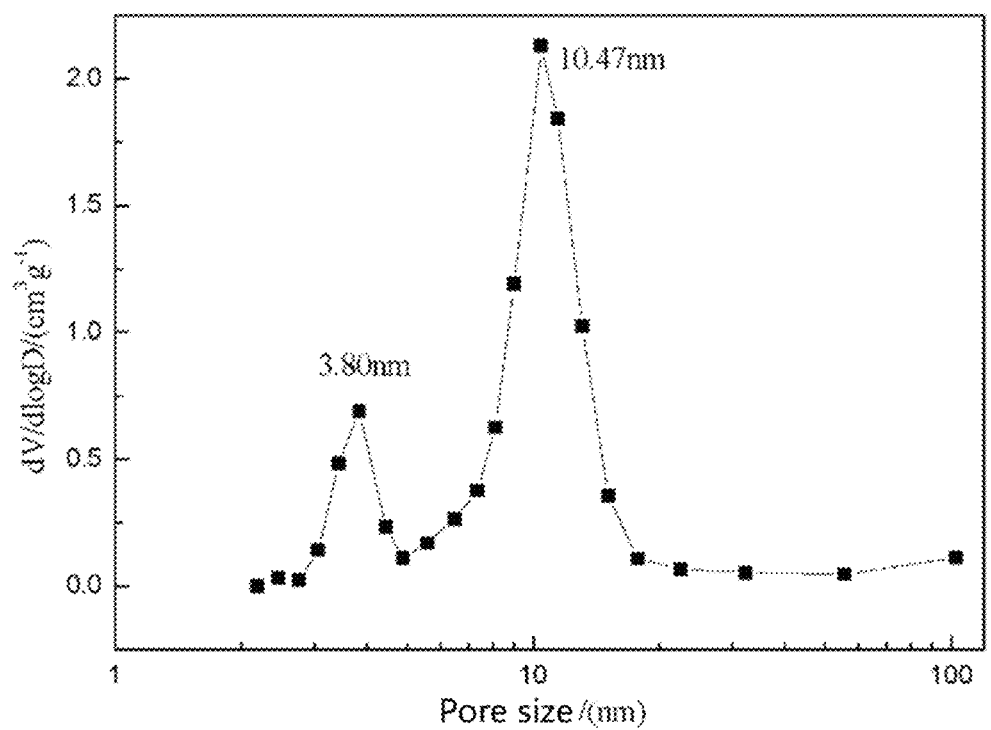
Figures 1, 2, 3, 4, 5, 6, 7, 8, 9, 10, 11, 12, 13, 14, 15, 16, 17, 18, 19, 20, 21, 22, 23, 24, 25, 26, 27, 28:
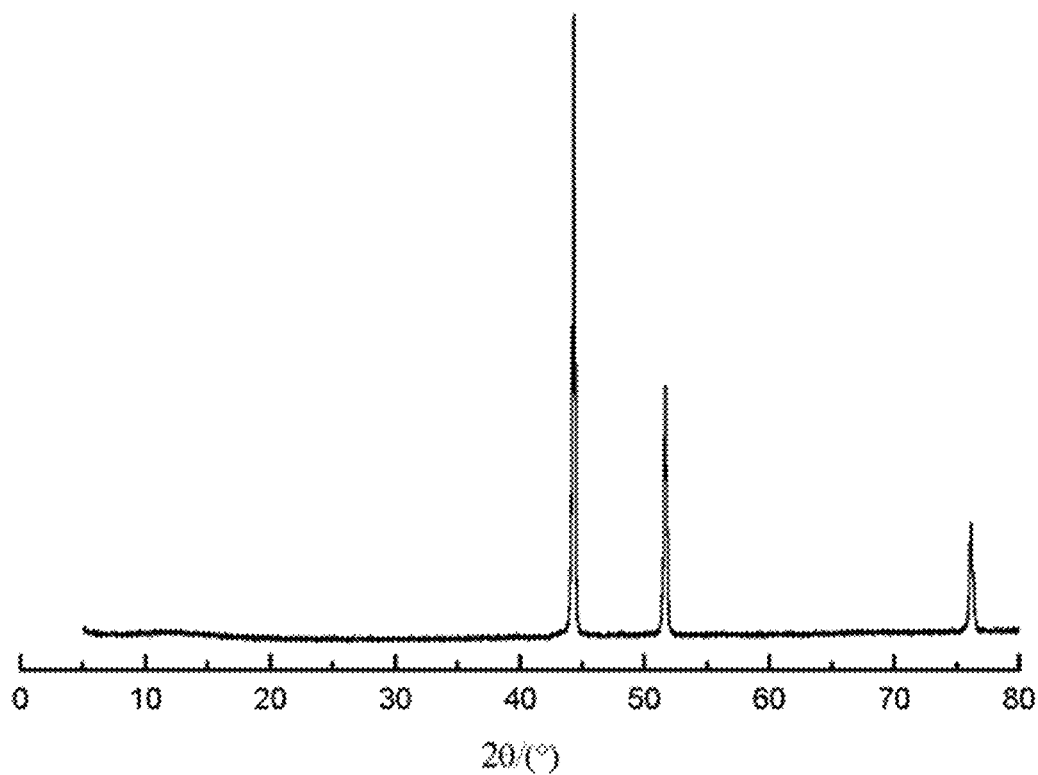
Figures 1, 2:
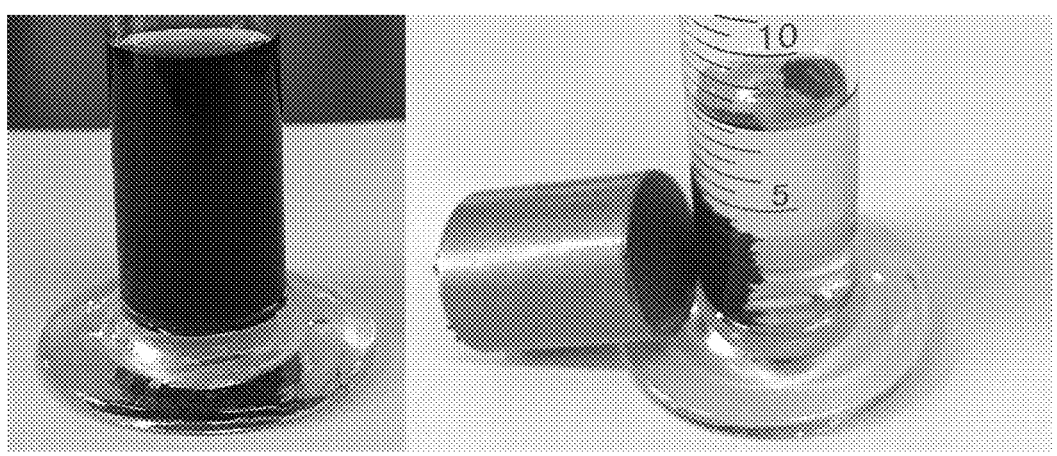
Figure 2:
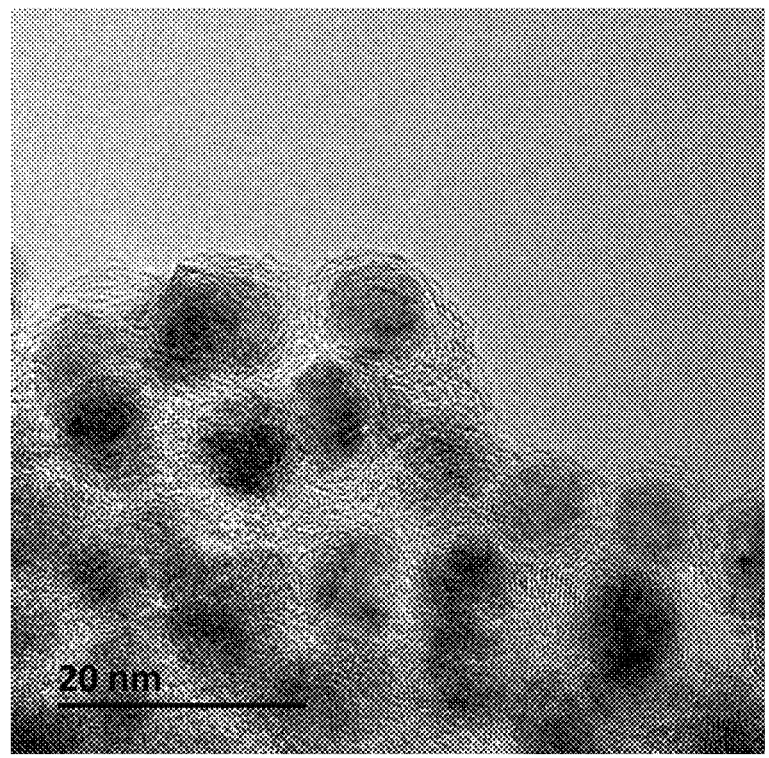
Figures 2, 3:
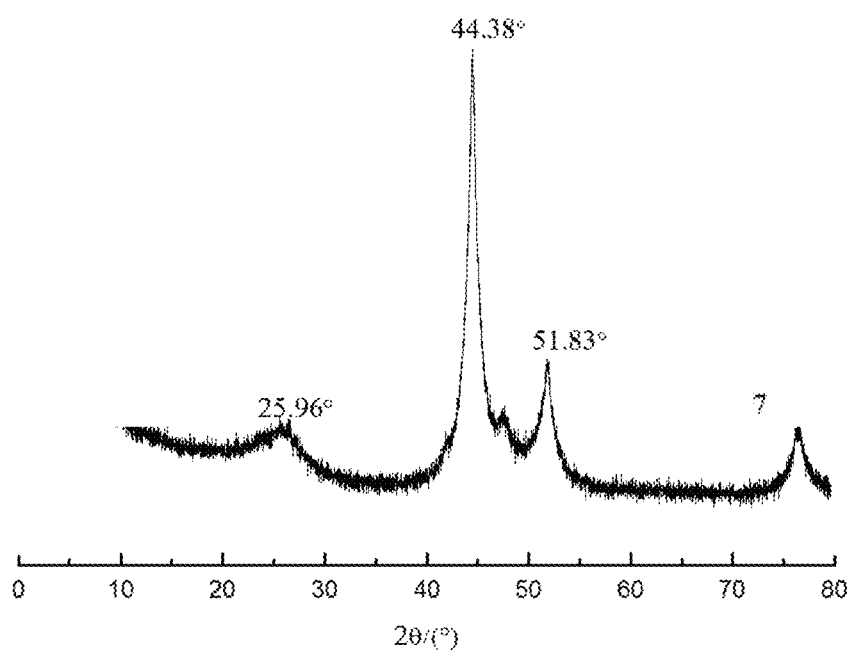
Figures 2, 3, 4, 4A:
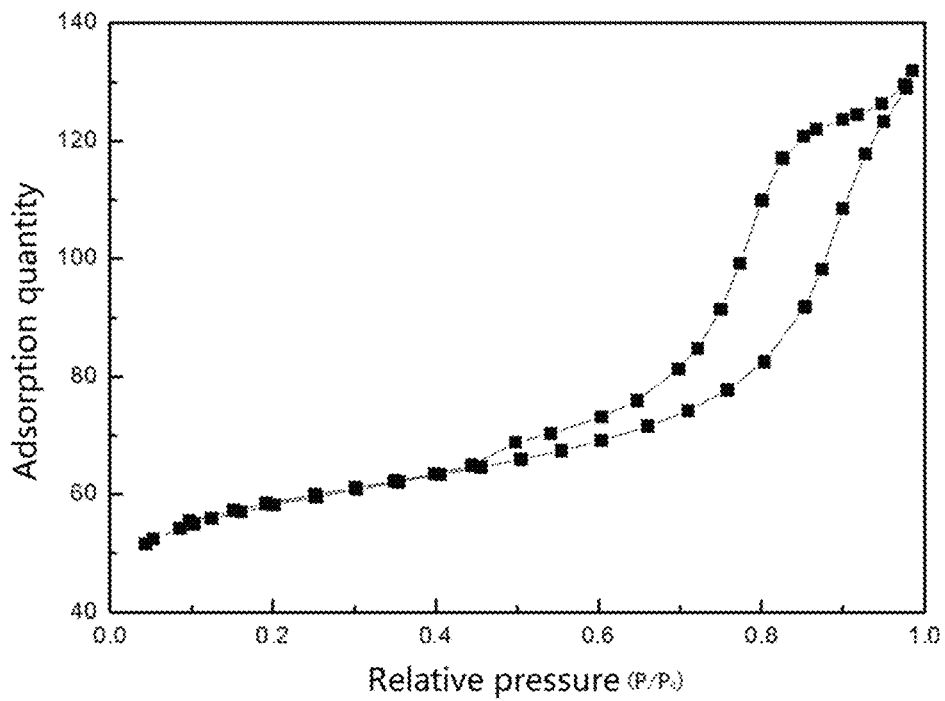
Figures 2, 3, 4, 4B:
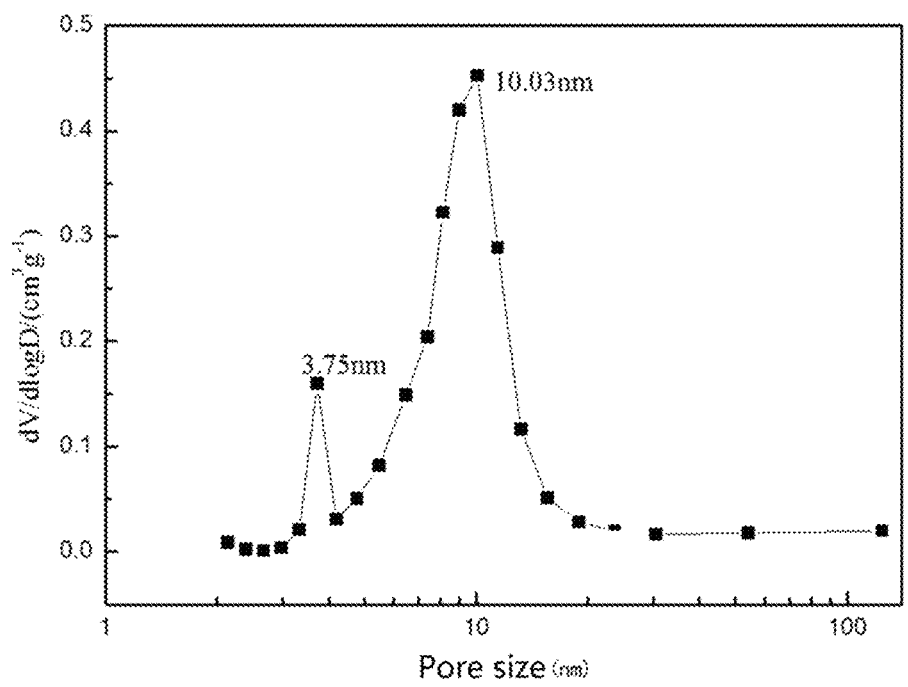
Figures 2, 3, 4, 5:
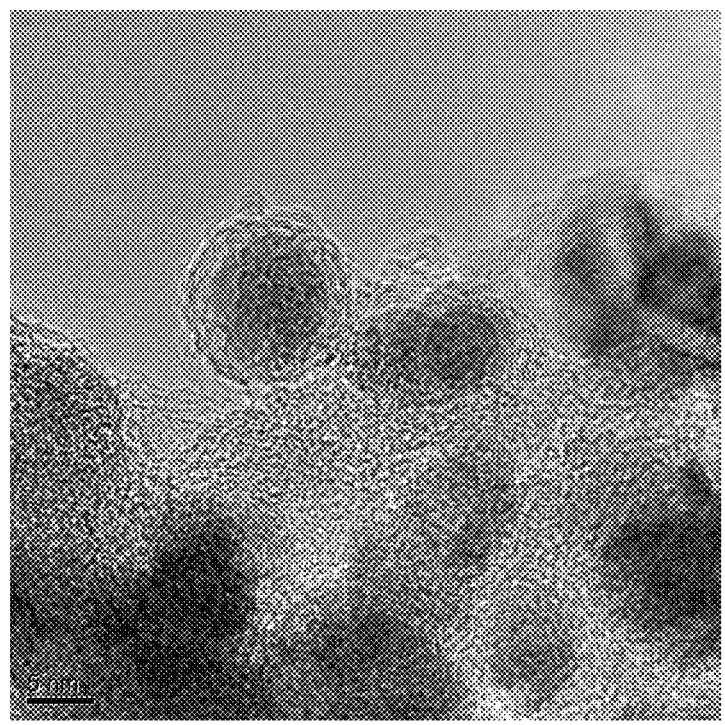
Figures 2, 3, 4, 5, 6:
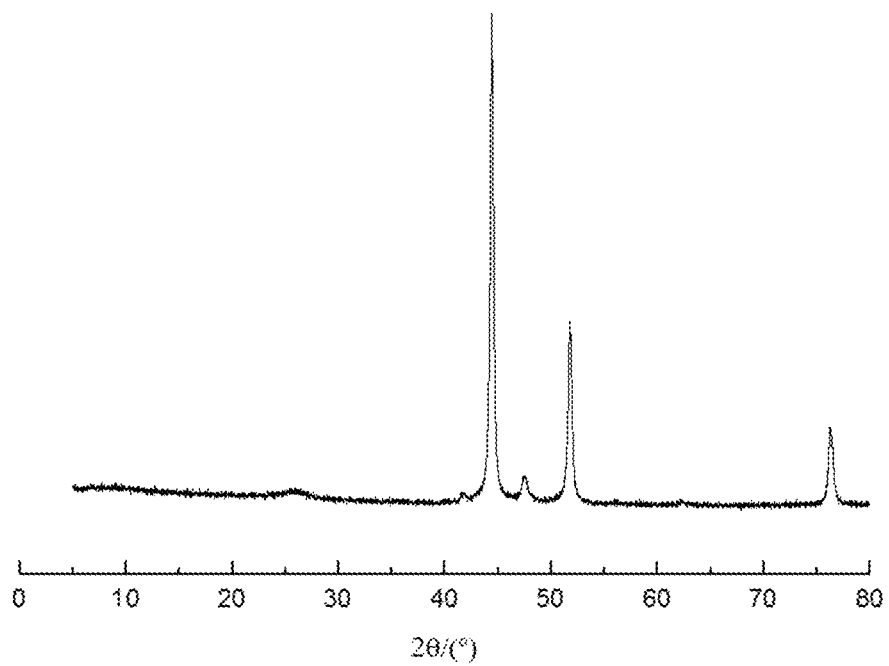
Figures 2, 3, 4, 5, 6, 7:
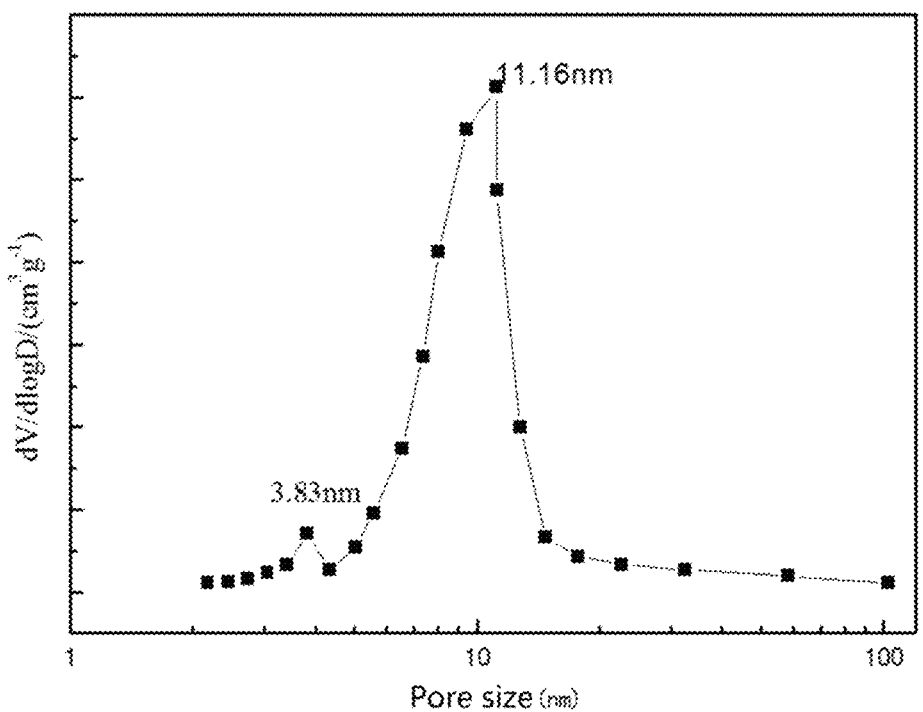
Figures 2, 3, 4, 5, 6, 7, 8:
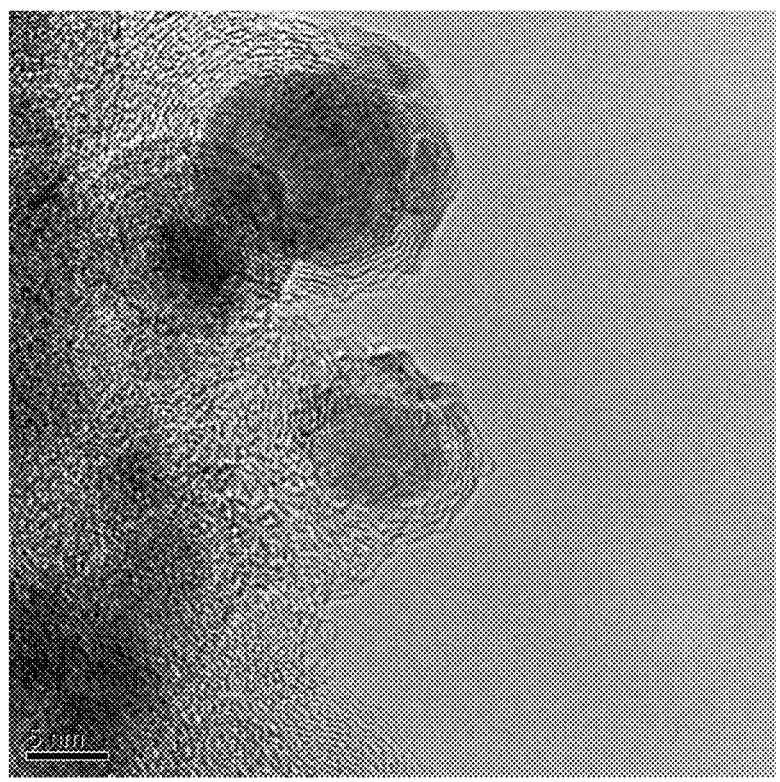
Figures 2, 3, 4, 5, 6, 7, 8, 9:
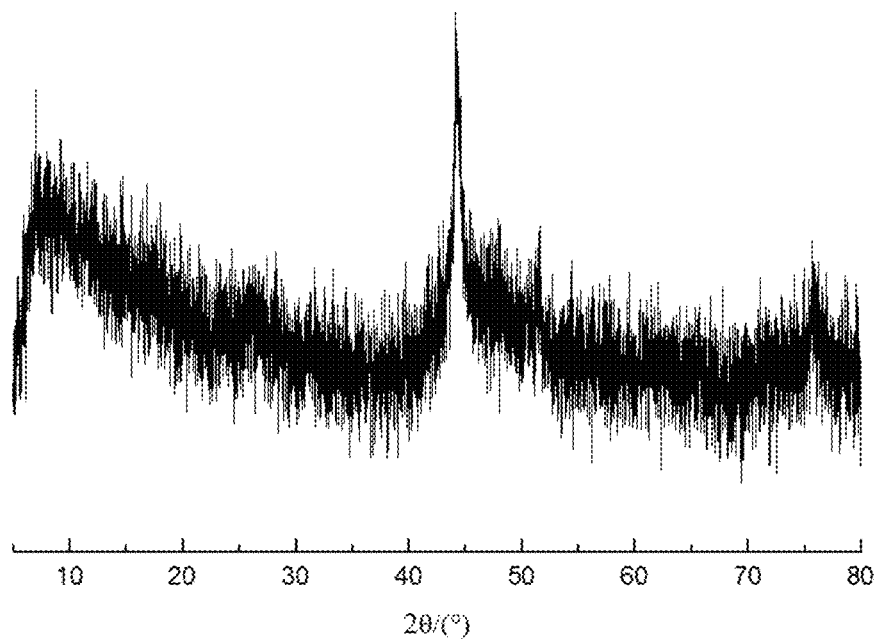
Figures 2, 3, 4, 5, 6, 7, 8, 9, 10:
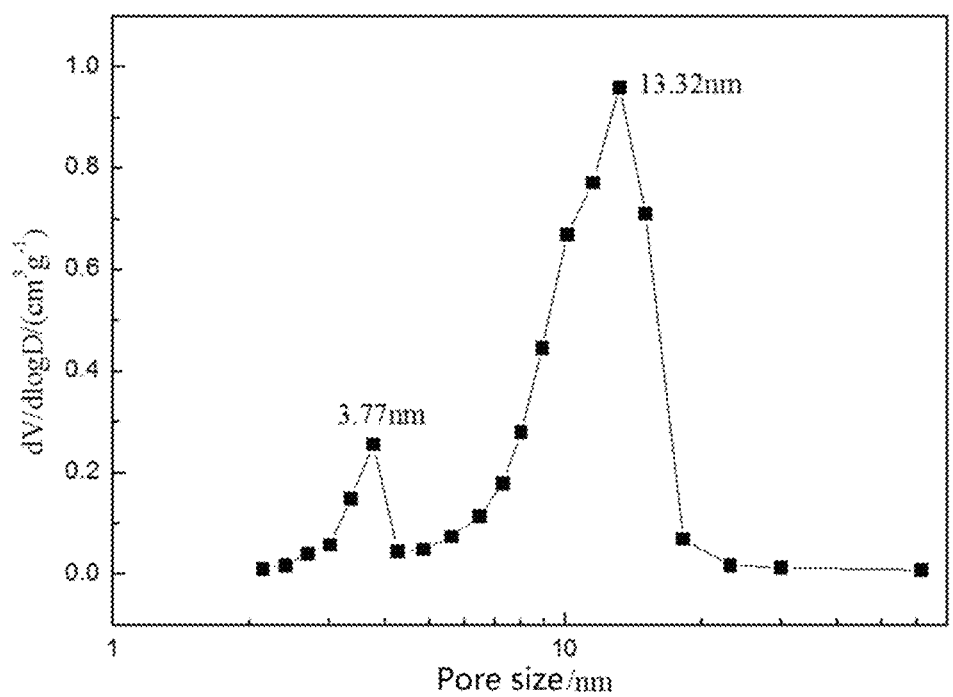
Figures 2, 3, 4, 5, 6, 7, 8, 9, 10, 11:
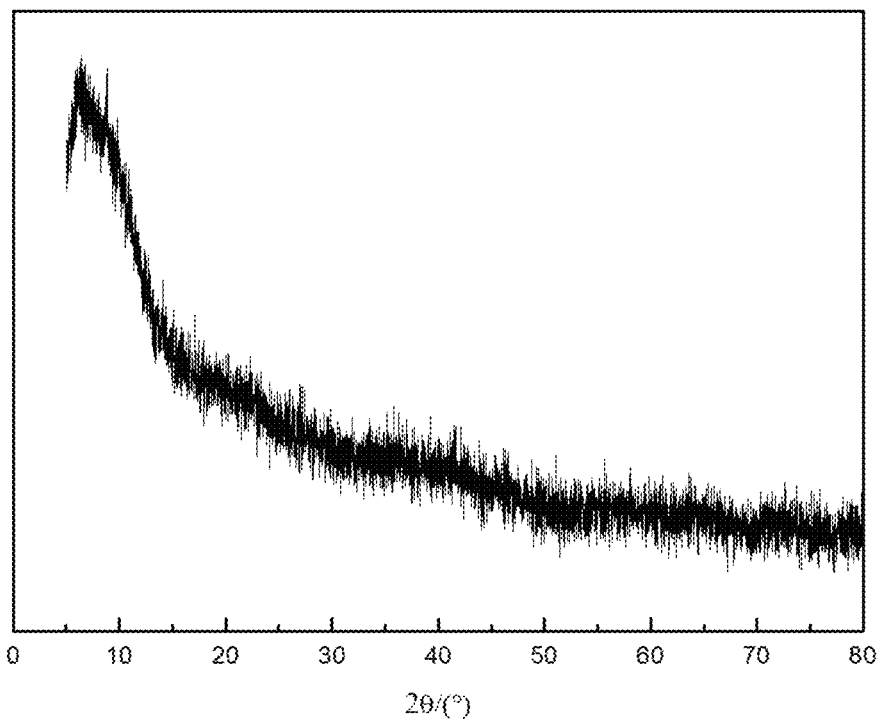
Figures 2, 3, 4, 5, 6, 7, 8, 9, 10, 11, 12:
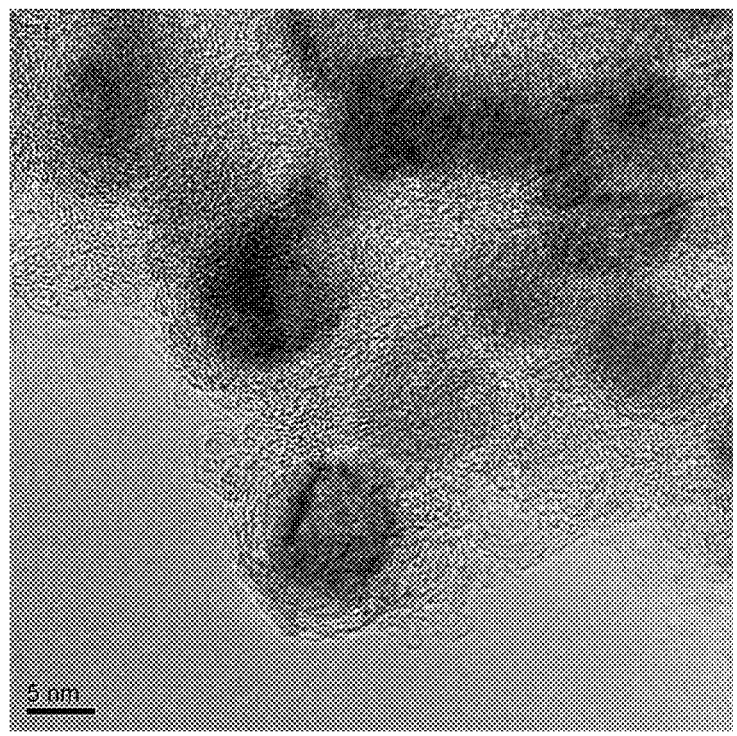
Figures 2, 3, 4, 5, 6, 7, 8, 9, 10, 11, 12, 13:
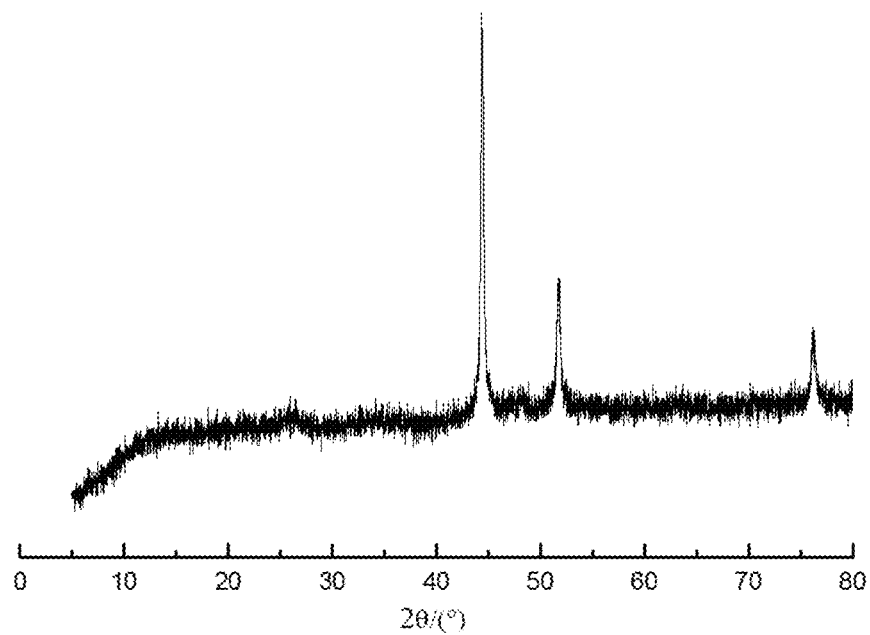
Figures 2, 3, 4, 5, 6, 7, 8, 9, 10, 11, 12, 13, 14:
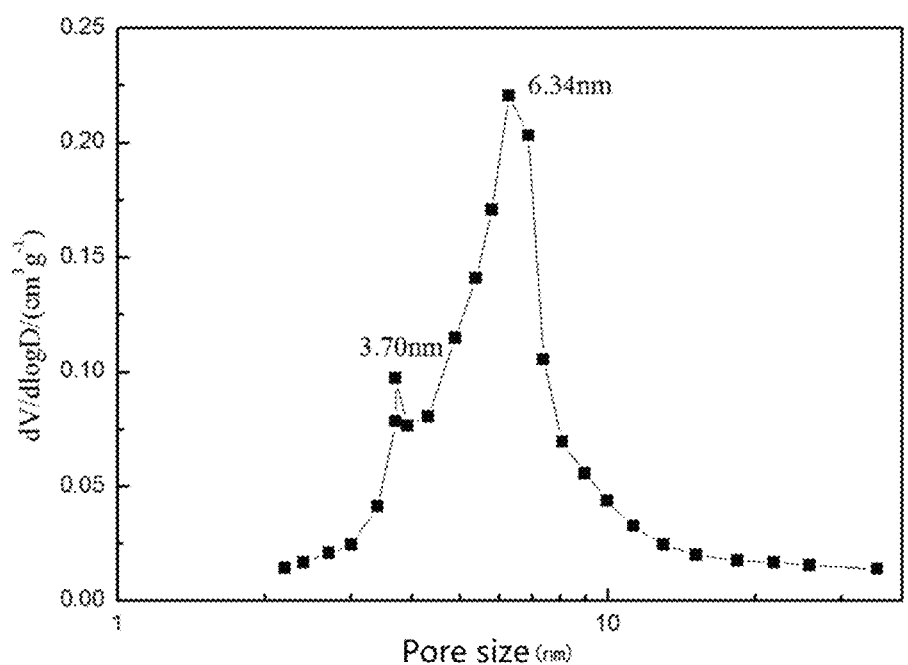
Figures 2, 3, 4, 5, 6, 7, 8, 9, 10, 11, 12, 13, 14, 15:
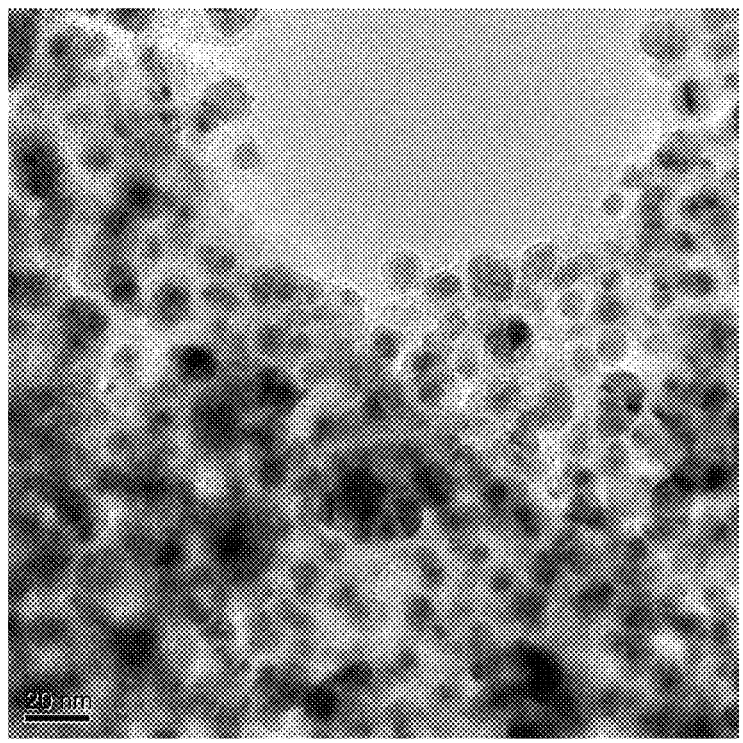
Figures 2, 3, 4, 5, 6, 7, 8, 9, 10, 11, 12, 13, 14, 15, 16:
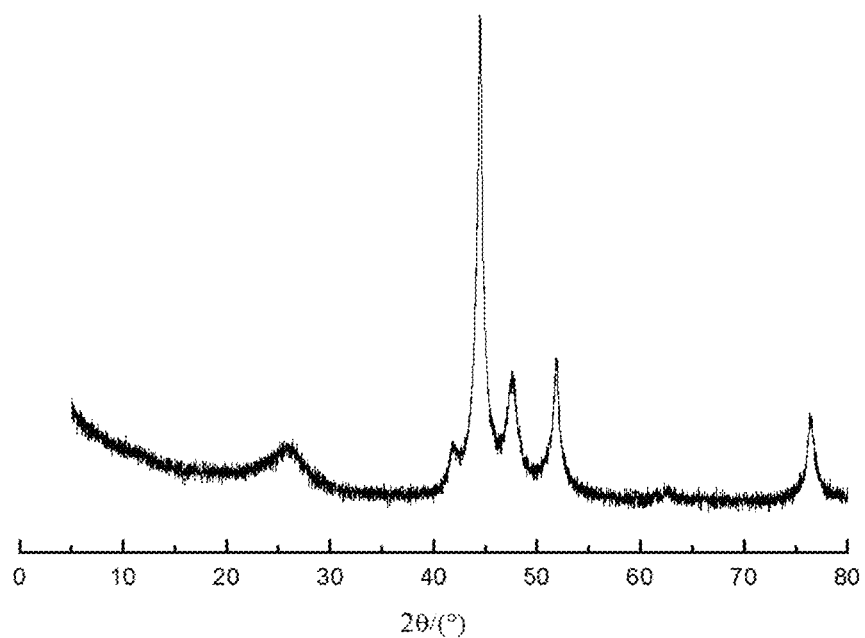
Figures 2, 3, 4, 5, 6, 7, 8, 9, 10, 11, 12, 13, 14, 15, 16, 17:
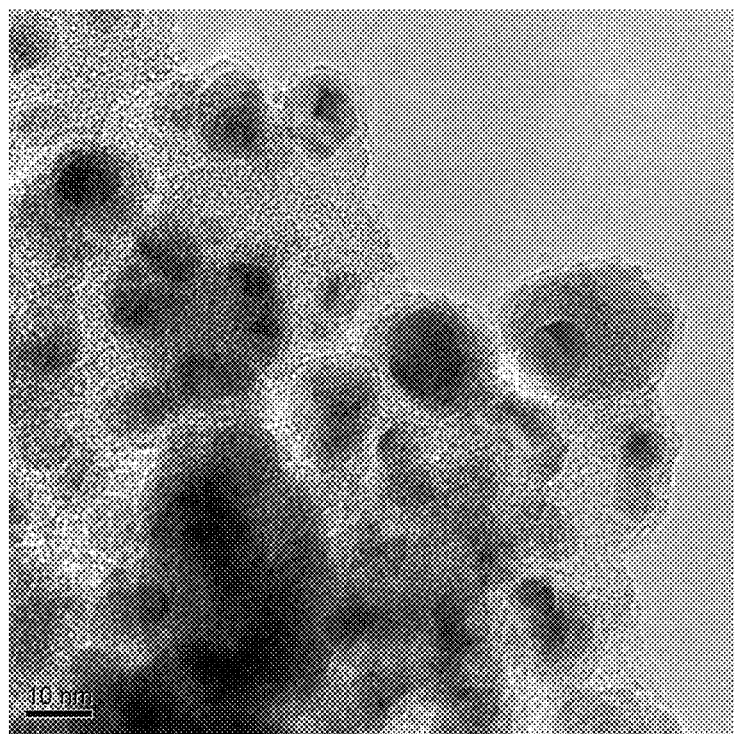
Figures 2, 3, 4, 5, 6, 7, 8, 9, 10, 11, 12, 13, 14, 15, 16, 17, 18:
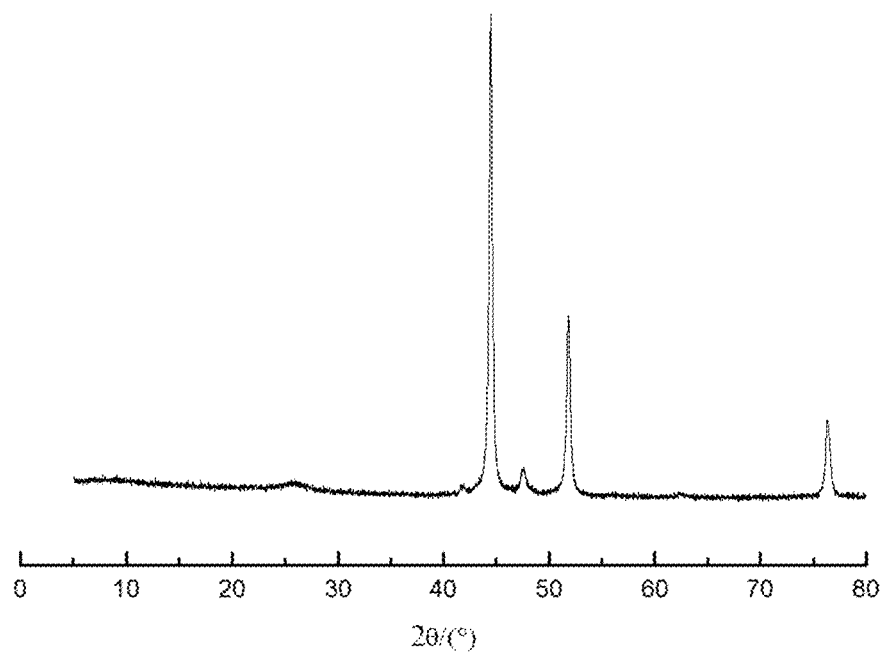
Figures 2, 3, 4, 5, 6, 7, 8, 9, 10, 11, 12, 13, 14, 15, 16, 17, 18, 19:
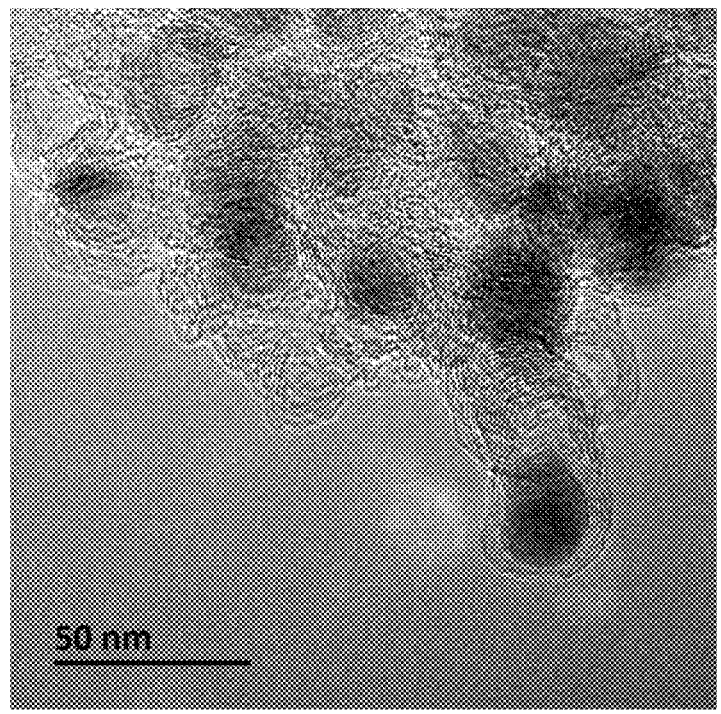
Figures 2, 3, 4, 5, 6, 7, 8, 9, 10, 11, 12, 13, 14, 15, 16, 17, 18, 19, 20:
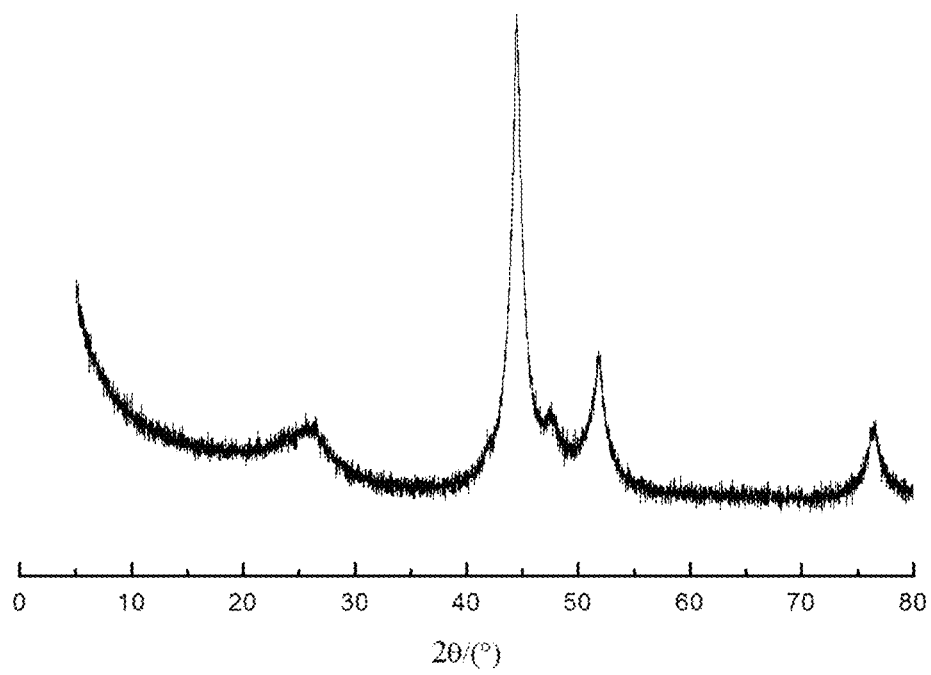
Figures 2, 3, 4, 5, 6, 7, 8, 9, 10, 11, 12, 13, 14, 15, 16, 17, 18, 19, 20, 21:
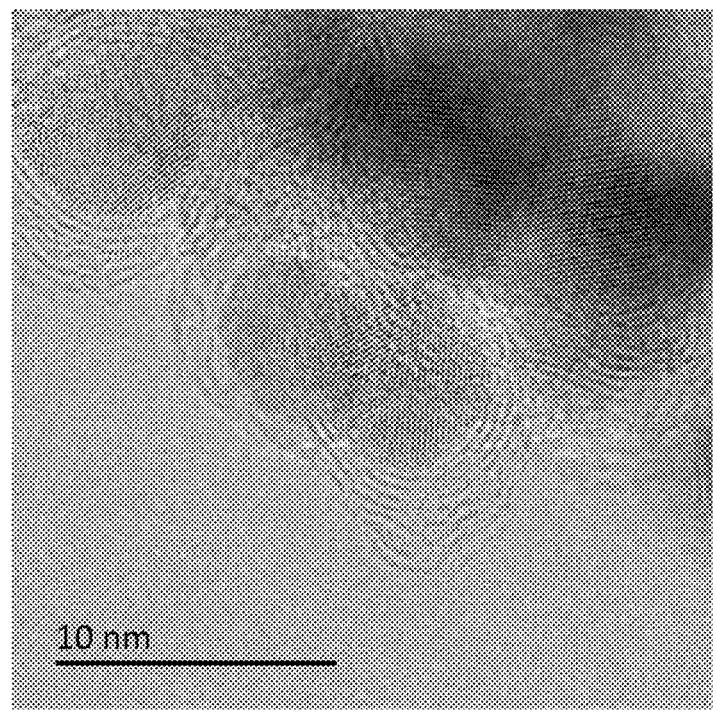
Figures 2, 3, 4, 5, 6, 7, 8, 9, 10, 11, 12, 13, 14, 15, 16, 17, 18, 19, 20, 21, 22:
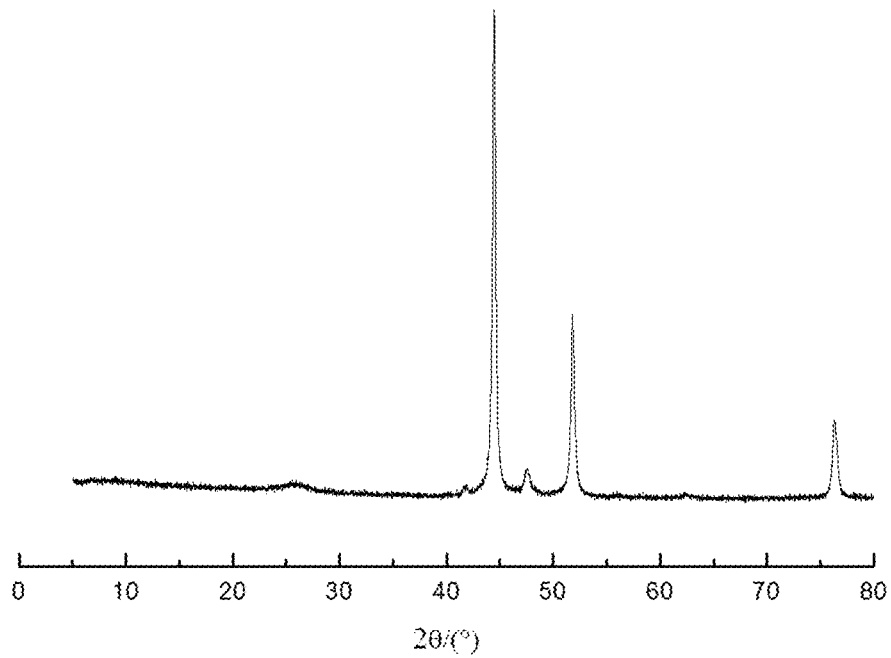
Figures 2, 3, 4, 5, 6, 7, 8, 9, 10, 11, 12, 13, 14, 15, 16, 17, 18, 19, 20, 21, 22, 23:
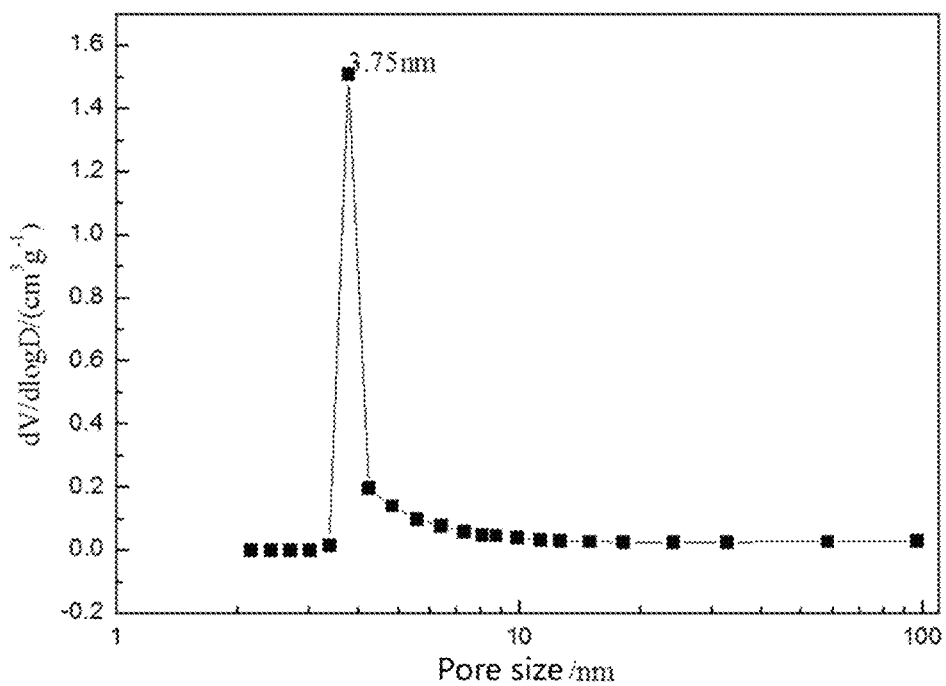
Figures 2, 3, 4, 5, 6, 7, 8, 9, 10, 11, 12, 13, 14, 15, 16, 17, 18, 19, 20, 21, 22, 23, 24:
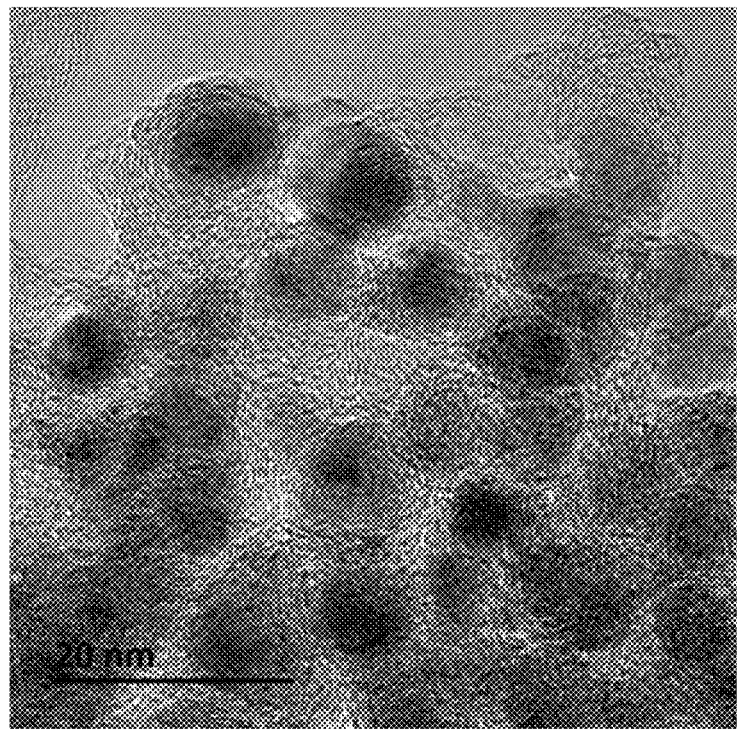
Figures 2, 3, 4, 5, 6, 7, 8, 9, 10, 11, 12, 13, 14, 15, 16, 17, 18, 19, 20, 21, 22, 23, 24, 25:
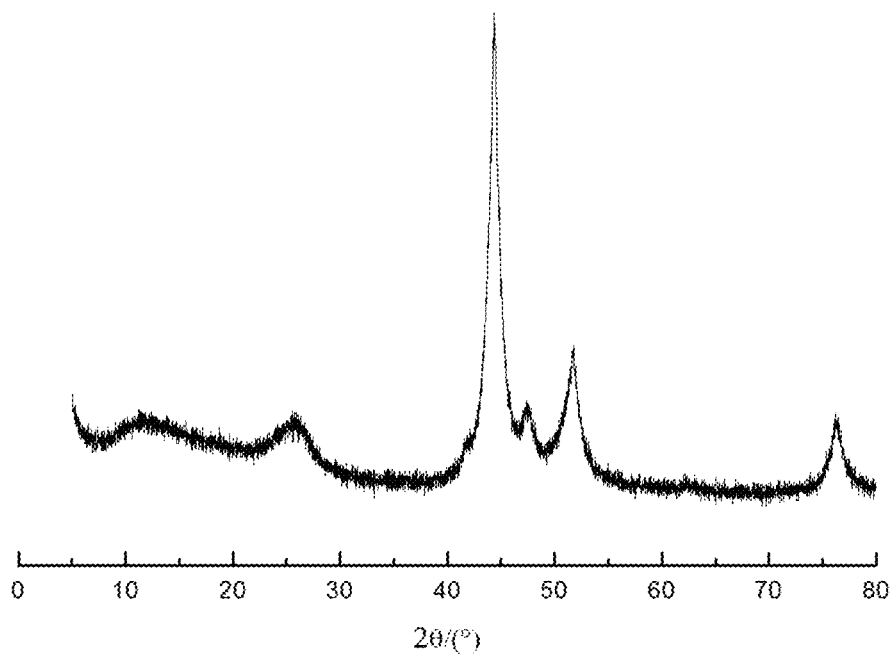
Figures 2, 3, 4, 5, 6, 7, 8, 9, 10, 11, 12, 13, 14, 15, 16, 17, 18, 19, 20, 21, 22, 23, 24, 25, 26:
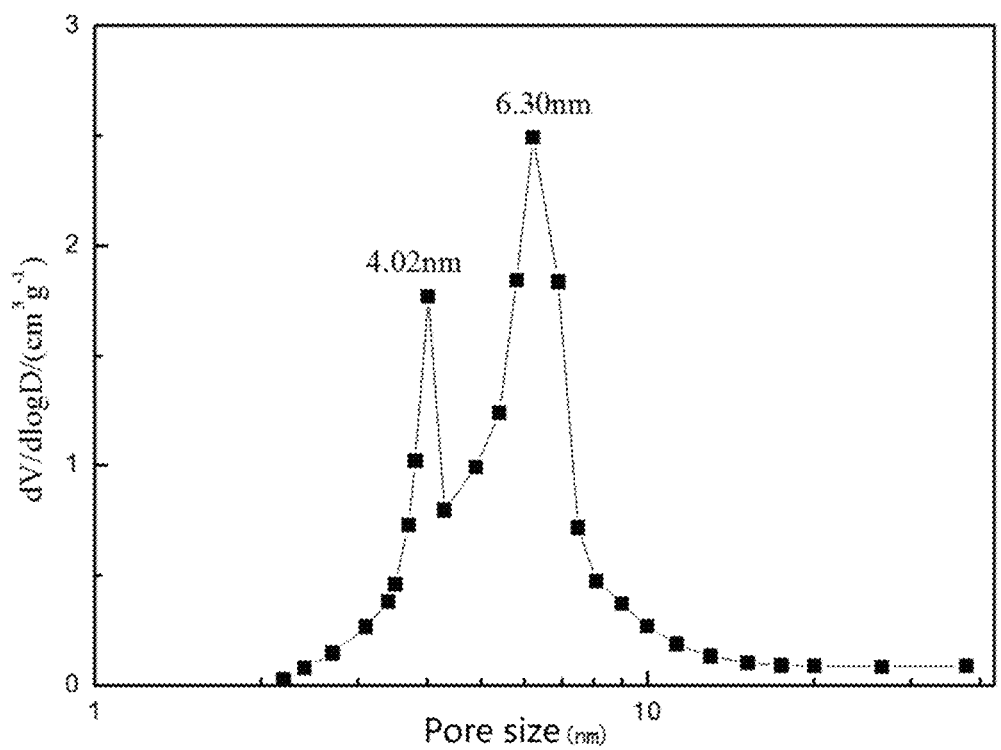
Figures 2, 3, 4, 5, 6, 7, 8, 9, 10, 11, 12, 13, 14, 15, 16, 17, 18, 19, 20, 21, 22, 23, 24, 25, 26, 27:
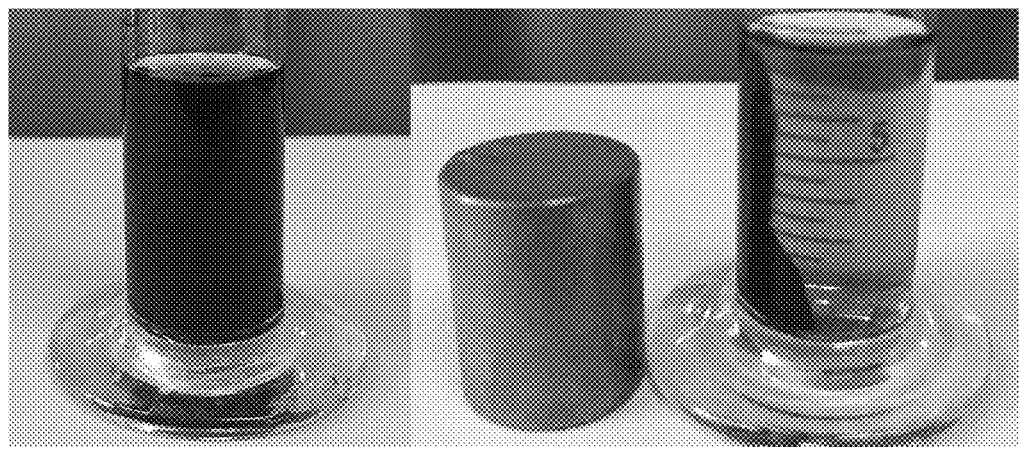
Figures 2, 3, 4, 5, 6, 7, 8, 9, 10, 11, 12, 13, 14, 15, 16, 17, 18, 19, 20, 21, 22, 23, 24, 25, 26, 27, 28:
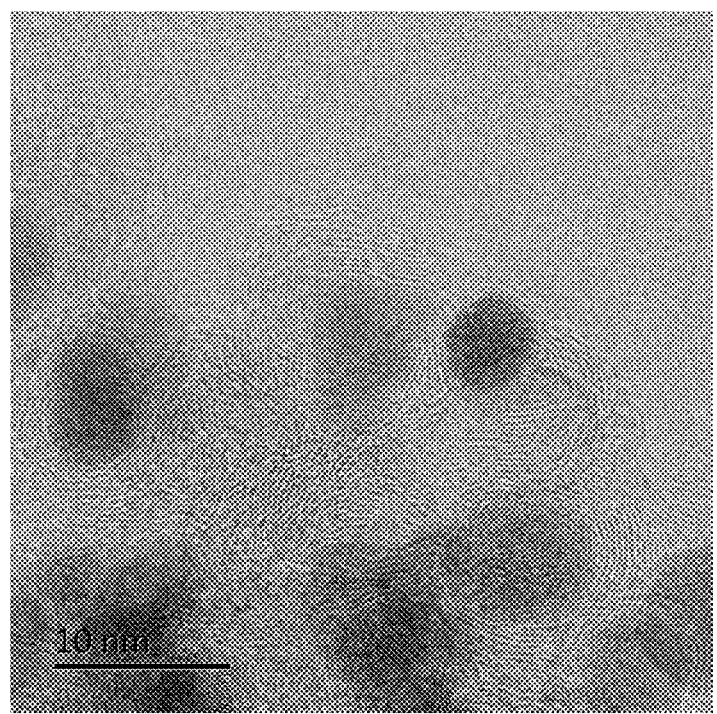
Figures 2, 3, 4, 5, 6, 7, 8, 9, 10, 11, 12, 13, 14, 15, 16, 17, 18, 19, 20, 21, 22, 23, 24, 25, 26, 27, 28, 29:
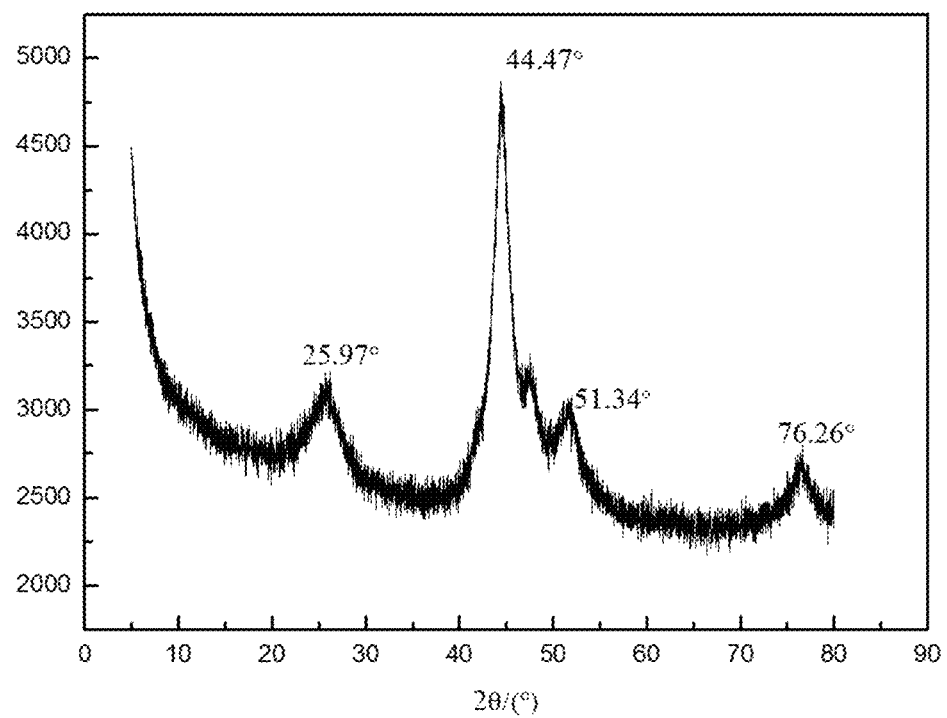
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30:
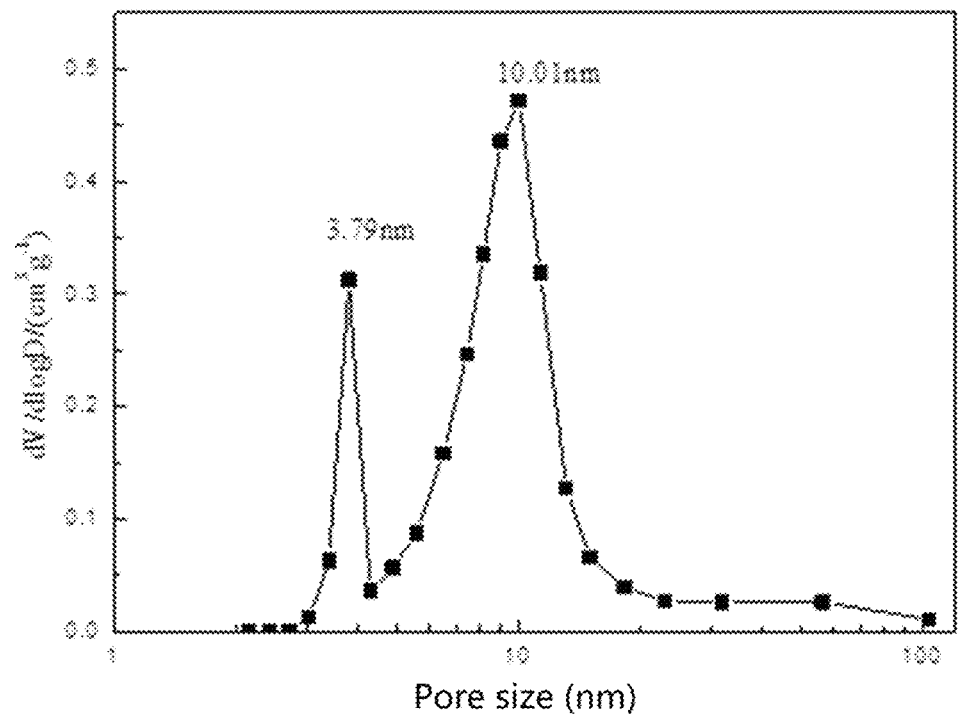

FIG. 3-5 shows an XRD pattern of the carbon-coated nickel nanocomposite material P4 obtained in Example 3-2.

FIG. 3-6 shows an X-ray Photoelectron Spectroscopy (XPS) spectrum of the carbon-coated nickel nanocomposite material P4 obtained in Example 3-2.

FIG. 3-7A is a diagram showing the $N_2$ adsorption-desorption isotherm of the carbon-coated nickel nanocomposite material P4 obtained in Example 3-2.

FIG. 3-7B is a diagram showing the pore-size distribution curve of the carbon-coated nickel nanocomposite material P4 obtained in Example 3-2.

DETAILED DESCRIPTION OF THE INVENTION

The present application will be further described hereinafter in detail with reference to specific embodiments thereof and the accompanying drawings. It should be noted that the specific embodiments of the present application are provided for illustration purpose only, and are not intended to be limiting in any manner.

In the context of the present application, in addition to those matters explicitly stated, any matter or matters not mentioned are considered to be the same as those known in the art without any change. Moreover, any of the embodiments described herein can be freely combined with another one or more embodiments described herein, and the technical solutions or ideas thus obtained are considered as part of the original disclosure or original description of the present application, and should not be considered to be a new matter that has not been disclosed or anticipated herein, unless it is clear to those skilled in the art that such a combination is obviously unreasonable.

The numerical values disclosed in the present description include not only the numerical values specifically disclosed in the working examples but also the endpoints of each numerical range described in the description, and the ranges obtained by any combination of the numerical values should be considered to be disclosed or recited in the present application. Unless otherwise indicated, the numerical ranges defined herein are inclusive of their endpoints.

As used herein, the terms "comprise(s)/comprising" and "include(s)/including" are open-ended expressions that are substantially equivalent to the phrase "including, but not limited to".

As used herein, the singular forms "a", "an" and "the" include plural aspects unless the context clearly dictates otherwise. Thus, for example, when referring to "a thing", it may include more than one such thing, as in all embodiments and variations substantially described hereinbefore with reference to the examples and drawings.

All patents and non-patent documents cited herein, including but not limited to textbooks and journal articles and the like, are incorporated herein by reference in their entirety.

Definition of Terms

Unless otherwise stated, the terms used in the present description should be understood to have the following meanings. Any term not directly defined herein should be understood to have a meaning corresponding to its common understanding in the art to which the present application pertains.

In the context herein, the terms "nanocomposite material comprising carbon-coated transition metal particles" and "carbon-coated transition metal nanocomposite material" are used interchangeably, and refer to a nanocomposite material comprising carbon-coated transition metal particles having a "core-shell structure".

As used herein, the term "core-shell structure" refers to a composite structure having a core that is a transition metal nanoparticle and a shell (i.e., an outer layer) that is a graphitized carbon layer, formed by covering the outer surface of the transition metal nanoparticle with a graphitized carbon material.

As used herein, the term "graphitized carbon layer" refers to a carbon structure that can be clearly observed as a layered structure, rather than an amorphous structure, under a high-resolution transmission electron microscope, with an interlayer distance of about 0.34 nm. The composite material formed by covering a transition metal nanoparticle with the graphitized carbon layer generally has a spherical or quasi-spherical shape.

As used herein, the expression "graphitized carbon layer doped with oxygen and/or nitrogen" means that said graphitized carbon layer is a "graphitized carbon layer doped with oxygen" or a "graphitized carbon layer doped with oxygen and nitrogen", which may generally be further doped with a minor amount of hydrogen.

As used herein, the "oxygen" in the "graphitized carbon layer doped with oxygen" refers to the oxygen element, including the oxygen element present in the graphitized carbon layer in any form. The "oxygen content" of the nanocomposite material refers to the content of the oxygen element, i.e., the total content of the oxygen element present in various forms.

As used herein, in the "graphitized carbon layer doped with oxygen and nitrogen", the "oxygen" refers to the oxygen element, while the "nitrogen" refers to the nitrogen element, including the oxygen element and the nitrogen element present in the graphitized carbon layer in any form. The "oxygen content" of the nanocomposite material refers to the content of the oxygen element, i.e., the total content of the oxygen element present in various forms; likewise, the "nitrogen content" of the nanocomposite material refers to the content of the nitrogen element, i.e., the total content of the nitrogen element present in various forms.

As used herein, the term "mesopore(s)" refers to pores having a pore size in the range of 2 to 50 nm.

As used herein, pores with a pore size of less than 2 nm are defined as micropores, while pores with a pore size of more than 50 nm are defined as macropores.

As used herein, the term "distribution peak of mesopores" refers to the distribution peak of mesopores observed on a pore-size distribution curve obtained via calculation from a desorption curve in accordance with the Barrett-Joyner-Halenda (BJH) method.

As used herein, the term "carbon coverage rate" is used to define the proportion of the transition metal nanoparticles that are effectively covered by the graphitized carbon layer, which can be observed by high-resolution transmission electron microscopy (HRTEM).

As used herein, the term "tightness of carbon wrapping" is used to define the proportion of the transition metal nanoparticles isolated from the external environment by the graphitized carbon layer, which can be characterized by the results of the acid leaching test.

As used herein, the term "acid treatment" refers to a treatment carried out on the pyrolysis product obtained after the high-temperature pyrolysis step with a non-oxidizing strong acid during the preparation of the carbon-coated transition metal nanocomposite material, which treatment is an optional step in the preparation of the nanocomposite material, i.e. said treatment, if present, forms a part of the preparation.

As used herein, the term "acid leaching" refers to a step of treating the carbon-coated transition metal nanocomposite material with an aqueous sulfuric acid solution to measure its "loss on acid leaching", which does not form a part of the preparation of the carbon-coated transition metal nanocomposite material.

As used herein, the term "loss on acid leaching" refers to the loss rate of the transition metal after acid leaching of the carbon-coated transition metal nanocomposite material, which is used to reflect the tightness of the wrapping of the transition metal nanoparticle by the graphitized carbon layer. If the transition metal nanoparticle is not tightly wrapped by the graphitized carbon layer, a loss of the transition metal in the core may occur after acid leaching due to the dissolution in acid. The greater the loss on acid leaching is, the lower the tightness of the wrapping of the transition metal nanoparticles by the graphitized carbon layer is; conversely, the smaller the loss on acid leaching is, the higher the tightness of the wrapping of the transition metal nanoparticles by the graphitized carbon layer.

In the present application, a nanocomposite material with a loss on acid leaching of 10% or less is defined as a "tightly-wrapped nanocomposite material". Having a loss on acid leaching of 10% or less indicates that the carbon-coated transition metal particles comprised in the nanocomposite material have a tightly coated core-shell structure, i.e. the transition metal nanoparticles are tightly wrapped by the graphitized carbon layer and substantially isolated from the outside.

In a first aspect, the present application provides a nanocomposite material comprising carbon-coated transition metal particles, the carbon-coated transition metal particles having a core-shell structure, the shell layer being a graphitized carbon layer doped with oxygen and/or nitrogen, and the core being a transition metal nanoparticle, wherein the nanocomposite material is a porous material having at least one distribution peak of mesopores, i.e., there is at least one distribution peak of mesopores on the pore-size distribution curve of the nanocomposite material obtained via calculation from a desorption curve in accordance with the Barrett-Joyner-Halenda (BJH) method.

In a preferred embodiment, the shell layer of the carbon-coated transition metal particles is a graphitized carbon layer doped with oxygen, which may not be doped with any element other than hydrogen and oxygen.

In another preferred embodiment, the shell layer of the carbon-coated transition metal particles is a graphitized carbon layer doped with oxygen and nitrogen, which may not be doped with any element other than hydrogen, oxygen and nitrogen.

In a preferred embodiment, the nanocomposite material is a porous material having two or more distribution peaks of mesopores.

In preferred embodiments, the nanocomposite material may have a loss on acid leaching of 40% or less, for example, about 10% to about 20%, about 20% to about 30%, or about 30% to about 40%, preferably 30% or less, and more preferably 10% or less. As described above, the loss on acid leaching reflects the tightness of the wrapping of the transition metal core by the graphitized carbon layer, and a smaller loss on acid leaching indicates a higher tightness of wrapping.

In a preferred embodiment, the nanocomposite material may further comprise an amorphous carbon matrix, the carbon-coated transition metal particles being dispersed in the amorphous carbon matrix. More preferably, the nanocomposite material is consisted of an amorphous carbon matrix and carbon-coated transition metal particles dispersed therein.

Particularly, the nanocomposite material according to the present application does not comprise any carbon nanotube.

In a preferred embodiment, the shell layer of the carbon-coated transition metal particles is a graphitized carbon layer doped with oxygen, and the nanocomposite material has a distribution peak of mesopores in the pore size range of 2-7 nm and a distribution peak of mesopores in the pore size range of 8-20 nm; or the shell layer of the carbon-coated transition metal particle is a graphitized carbon layer doped with oxygen and nitrogen, and the nanocomposite material has a distribution peak of mesopores in the pore size range of 2-5 nm and a distribution peak of mesopores in the pore size range of 6-15 nm, and further preferably, the proportion of the mesopore volume within the pore size range of 2-5 nm to the total pore volume of the nanocomposite material is more than about 5%, such as about 10% to about 30%.

In a preferred embodiment, the nanocomposite material has a proportion of mesopore volume to total pore volume of greater than about 50%, more preferably greater than about 80%, even more preferably greater than about 90%, particularly preferably greater than about 95%, and most preferably about 100%. By controlling the proportion of mesopore volume to total pore volume, the composite material may have a structure rich in mesopores, thereby providing a higher mass transfer efficiency.

In a preferred embodiment, the mesopore volume of the nanocomposite material is between about 0.05 cm$^3$/g and about 1.25 cm$^3$/g. In some particular embodiments, when the shell layer of the carbon-coated transition metal particles is a graphitized carbon layer doped with oxygen, the mesopore volume of the nanocomposite material may be about 0.30-0.50 cm$^3$/g. In other particular embodiments, when the shell layer of the carbon-coated transition metal particles is a graphitized carbon layer doped with oxygen and nitrogen, the mesopore volume of the nanocomposite material may be about 0.10-0.30 cm$^3$/g.

In a preferred embodiment, the specific surface area of the nanocomposite material is greater than about 140 m$^2$/g, preferably greater than about 200 m$^2$/g.

In a preferred embodiment, the nanocomposite material has a carbon content of about 10.0% to about 60.0% by mass and a transition metal content of about 30.0% to about 85.0% by mass. In some particular embodiments, when the shell layer of the carbon-coated transition metal particles is a graphitized carbon layer doped with oxygen, the nanocomposite material may have a carbon content of about 15.0% to about 40.0%, and a transition metal content of about 50.0% to about 80.0%; or alternatively, when the shell layer of the carbon-coated transition metal particles is a graphitized carbon layer doped with oxygen and nitrogen, the nanocomposite material may have a carbon content of about 30.0% to about 50.0%, and a transition metal content of about 30.0% to about 60.0%.

In a preferred embodiment, the shell layer of the carbon-coated transition metal particles is a graphitized carbon layer doped with oxygen, and the nanocomposite material has an oxygen content of less than about 15.0% by mass, preferably about 1.0% to about 10.0%, more preferably about 0.2% to about 5.0%; or alternatively, the shell layer of the carbon-coated transition metal particles is a graphitized carbon layer doped with oxygen and nitrogen, and the nanocomposite material has a total content of nitrogen and oxygen of less than about 15.0% by mass, preferably about 0.2% to about 12.0%, and more preferably about 0.5% to about 10.0%; further preferably, the nitrogen content is about 0.1% to about 10%, particularly preferably about 1% to about 5%.

In some particular embodiments, the graphitized carbon layer may be further doped with hydrogen, and the nanocomposite material has a hydrogen content of about 0.2-2% by mass.

In a particular embodiment, the transition metal element is present in a reduced state (e.g. zero-valent state) in the nanocomposite material according to the present application, i.e. there is no transition metal element present in an oxidized state (e.g. oxide).

Particularly, the sum of the content of each component in the nanocomposite material according to the present application is 100%.

In a preferred embodiment, the graphitized carbon layer has a thickness of about 0.3 nm to about 6.0 nm, more preferably about 0.3 nm to about 3 nm, and even more preferably about 1 nm to about 3 nm.

In a preferred embodiment, the particle size of the carbon-coated transition metal particles having a core-shell structure is about 1 nm to about 200 nm, more preferably about 3 nm to about 100 nm, and still more preferably about 4 nm to about 50 nm.

In a preferred embodiment, the transition metal is one or more selected from the group consisting of iron (Fe), cobalt (Co), nickel (Ni), copper (Cu) and zinc (Zn), more preferably one or more of iron, cobalt, nickel and copper, most preferably nickel (Ni).

In a preferred embodiment, the shell layer of the carbon-coated transition metal particle is a graphitized carbon layer doped with oxygen and nitrogen, and the transition metal nanoparticle may have a face-centered-cubic (fcc) lattice structure and/or a hexagonal-close-packed (hcp) lattice structure, i.e., there may be only particles having the face-centered-cubic lattice structure, only particles having the hexagonal-close-packed lattice structure, or both particles having the face-centered-cubic lattice structure and particles having the hexagonal-close-packed lattice structure.

Without being bound to a particular theory, the nanocomposite material according to the first aspect of the present application is considered to be a composite material having a mesoporous structure and composed of an amorphous carbon matrix, and "transition metal nanoparticles tightly wrapped by a graphitized carbon layer (substantially isolated from the outside)" and "transition metal nanoparticles accessible from the outside" dispersed therein. The surface of the graphitized carbon layer doped with oxygen and/or nitrogen of the nanocomposite material is rich in defective sites, and the carbon material has catalytic activity per se and can provide a synergetic effect with the transition metal nanoparticles, so that the nanocomposite material shows a better catalytic performance.

In addition, the nanocomposite material according to the first aspect of the present application has a structure rich in mesopores, which is beneficial to the diffusion of reactants and products, and provides a higher mass transfer efficiency, thereby exhibiting a more superior catalytic performance. When the nanocomposite material has a multi-level mesoporous structure with mesopores within different pore size ranges, the nanocomposite material can provide more unique performance and can be applied to a wider range of applications.

The nanocomposite material according to the first aspect of the present application is doped with oxygen and/or nitrogen in the graphitized carbon layer, in which the oxygen content can be adjusted by additionally introducing an oxygen-containing organic compound such as a polyol during its preparation, and the nitrogen content can be adjusted by additionally introducing a nitrogen-containing organic compound such as hexamethylenetetramine during its preparation. The catalytic performance of the carbon layer can be modified by adjusting the contents of nitrogen and oxygen in the nanocomposite material, so that it may be suitable for catalyzing different reactions.

In a second aspect, the present application provides a nanocomposite material comprising carbon-coated transition metal particles, the carbon-coated transition metal particles having a core-shell structure, the shell layer being a graphitized carbon layer doped with oxygen and/or nitrogen, and the core being a transition metal nanoparticle, wherein the nanocomposite material has a loss on acid leaching of 10% or less, i.e., the nanocomposite material is a tightly-wrapped nanocomposite material.

In a preferred embodiment, the shell layer of the carbon-coated transition metal particles is a graphitized carbon layer doped with oxygen, which may not be doped with any element other than hydrogen and oxygen.

In another preferred embodiment, the shell layer of the carbon-coated transition metal particles is a graphitized carbon layer doped with oxygen and nitrogen, which may not be doped with any element other than hydrogen, oxygen and nitrogen.

In a preferred embodiment, the nanocomposite material is a porous material having at least one distribution peak of mesopores. More preferably, the nanocomposite material is a porous material having two or more distribution peaks of mesopores.

In a preferred embodiment, the nanocomposite material may further comprise an amorphous carbon matrix, the carbon-coated transition metal particles being dispersed in the amorphous carbon matrix. More preferably, the nanocomposite material is consisted of an amorphous carbon matrix and carbon-coated transition metal particles dispersed therein.

Particularly, the nanocomposite material according to the present application does not comprise any carbon nanotube.

In a preferred embodiment, the nanocomposite material has a proportion of mesopore volume to total pore volume of greater than about 50%, more preferably greater than about 80%, even more preferably greater than about 90%, particularly preferably greater than about 95%, and most preferably about 100%.

In a preferred embodiment, the mesopore volume of the nanocomposite material is about 0.05 $cm^3/g$ to about 1.25 $cm^3/g$, and in some particular embodiments, the mesopore volume of the nanocomposite material may be about 0.30 $cm^3/g$ to about 0.50 $cm^3/g$. In some other particular embodiments, the mesopore volume of the nanocomposite material may be about 0.10 $cm^3/g$ to about 0.30 $cm^3/g$.

In a preferred embodiment, the specific surface area of the nanocomposite material is greater than about 140 $m^2/g$, preferably greater than about 200 $m^2/g$.

In a preferred embodiment, the shell layer of the carbon-coated transition metal particles is a graphitized carbon layer doped with oxygen, and the nanocomposite material has a distribution peak of mesopores in the pore size range of 2-7 nm and a distribution peak of mesopores in the pore size range of 8-20 nm; or alternatively, the shell layer of the carbon-coated transition metal particles is a graphitized carbon layer doped with oxygen and nitrogen, and the nanocomposite material has a distribution peak of mesopores in the pore size range of 2-5 nm and a distribution peak of mesopores in the pore size range of 6-16 nm, and further preferably, the proportion of the mesopore volume within the pore size range of 2-5 nm to the total pore volume of the nanocomposite material is more than about 5%, such as about 10% to about 30%.

In a preferred embodiment, the nanocomposite material has a carbon content of about 15.0% to about 60.0% by mass and a transition metal content of about 30.0% to about 80.0% by mass. In some particular embodiments, the nanocomposite material may have a carbon content of about 30% to about 60% by mass and a transition metal content of about 30% to about 60% by mass.

In a preferred embodiment, the shell layer of the carbon-coated transition metal particles is a graphitized carbon layer doped with oxygen, and the nanocomposite material has an oxygen content of less than about 15.0% by mass, preferably about 1.0% to about 10.0%, more preferably about 0.2% to about 5.0%; or alternatively, the shell layer of the carbon-coated transition metal particles is a graphitized carbon layer doped with oxygen and nitrogen, and the nanocomposite material has a total content of nitrogen and oxygen of less than about 15.0% by mass, preferably about 0.2% to about 12.0%, and more preferably about 0.5% to about 10.0%; further preferably, the nitrogen content is about 0.1% to about 10%, particularly preferably about 1% to about 5%.

In certain preferred embodiments, the shell layer of the carbon-coated transition metal particles is a graphitized carbon layer doped with oxygen and nitrogen, and the nanocomposite material has a nitrogen content of about 2-8% by mass.

In certain preferred embodiments, the shell layer of the carbon-coated transition metal particles is a graphitized carbon layer doped with oxygen and nitrogen, and the nanocomposite material has an oxygen content of about 3-9% by mass.

In some particular embodiments, the graphitized carbon layer may be further doped with hydrogen, and the nanocomposite material has a hydrogen content of about 0.2-2% by mass.

In a particular embodiment, the transition metal element is present in a reduced state (e.g. zero-valent state) in the nanocomposite material according to the present application, i.e. there is no transition metal element present in an oxidized state (e.g. oxide).

Particularly, the sum of the content of each component in the nanocomposite material according to the present application is 100%.

In a preferred embodiment, the graphitized carbon layer has a thickness of about 0.3 nm to about 6.0 nm, more preferably about 0.3 nm to about 3 nm, and even more preferably about 1 nm to about 3 nm.

In a preferred embodiment, the particle size of the carbon-coated transition metal particles having a core-shell structure is about 1 nm to about 200 nm, more preferably about 3 nm to about 100 nm, and still more preferably about 4 nm to about 50 nm.

In a preferred embodiment, the transition metal is one or more selected from the group consisting of iron (Fe), cobalt (Co), nickel (Ni), copper (Cu) and zinc (Zn), more preferably one or more of iron, cobalt, nickel and copper, most preferably nickel (Ni).

In a preferred embodiment, the shell layer of the carbon-coated transition metal particles is a graphitized carbon layer doped with oxygen and nitrogen, and the transition metal nanoparticles have a face-centered-cubic (fcc) lattice structure and/or a hexagonal-close-packed (hcp) lattice structure.

Without being bound to a particular theory, the nanocomposite material according to the second aspect of the present application is considered to be a composite material having a mesoporous structure and composed of an amorphous carbon matrix and "transition metal nanoparticles tightly wrapped by a graphitized carbon layer (substantially isolated from the outside)" dispersed therein. As compared with non-tightly-wrapped nanocomposite materials, a tightly-wrapped nanocomposite material can with better assurance provide a reduced loss rate of the transition metal in the core in application, so that the composite material can function more efficiently.

It is generally recognized in the art that the active site for catalyzing the hydrogenation reaction is the transition metal, and therefore regardless of the structure of the catalyst, it is necessary to allow the reactant to contact with the metal core. However, the nanocomposite material according to the present application in which the transition metal nanoparticles are tightly wrapped by the graphitized carbon layer still has an excellent capability of catalyzing the hydrogenation reduction of organic compounds.

In addition, the nanocomposite material according to the second aspect of the present application has a structure rich in mesopores, which is beneficial to the diffusion of reactants and products, and provides a higher mass transfer efficiency, thereby exhibiting a more superior catalytic performance. When the nanocomposite material has a multi-level mesoporous structure with mesopores within different pore size ranges, the nanocomposite material can provide more unique performance and can be applied to a wider range of applications.

The nanocomposite material according to the second aspect of the present application is doped with oxygen and/or nitrogen in the graphitized carbon layer, in which the oxygen content can be adjusted by additionally introducing an oxygen-containing organic compound such as a polyol during its preparation, and the nitrogen content can be adjusted by additionally introducing a nitrogen-containing organic compound such as hexamethylenetetramine during its preparation. The catalytic performance of the carbon layer can be modified by adjusting the contents of nitrogen and oxygen in the nanocomposite material, so that it may be suitable for catalyzing different reactions.

In a third aspect, the present application provides a method for preparing a nanocomposite material comprising carbon-coated transition metal particles, comprising the steps of:

i) mixing a mixture comprising a transition metal source and a polybasic organic carboxylic acid with a solvent to form a homogeneous solution;

ii) removing the solvent from the homogeneous solution to obtain a precursor;

iii) subjecting the precursor to high-temperature pyrolysis under an inert protective atmosphere or a reducing atmosphere; and iv) optionally, subjecting the pyrolysis product obtained in step iii) to a treatment with a non-oxidizing strong acid.

In a preferred embodiment, the mass ratio of the transition metal source to the polybasic organic carboxylic acid in the mixture used in step i) is about 1:0.1 to about 1:10, more preferably about 1:0.5 to about 1:5, and particularly preferably about 1:0.8 to about 1:3.

In a preferred embodiment, the mixture used in step i) further comprises a nitrogen-containing organic compound and/or an oxygen-containing organic compound different from the polybasic organic carboxylic acid.

In a further preferred embodiment, the mass ratio of the transition metal source, the polybasic organic carboxylic acid and the nitrogen-containing organic compound in the mixture used in step i) is about 1:0.1-100:0.1-100, more preferably about 1:0.5-5:0.5-5, and particularly preferably about 1:0.8-2:1-2.

In a further preferred embodiment, the nitrogen-containing organic compound is one or more selected from the group consisting of urea, melamine, dicyanodiamine, hexamethylenetetramine and amino acids, and the oxygen-containing organic compound is selected from polyols and organic carboxylic acids, such as lactic acid.

In certain preferred embodiments, the mixture used in step i) may further comprise other organic compound(s) different from the polybasic organic carboxylic acid, the nitrogen-containing organic compound and the oxygen-containing organic compound. Any organic compound that can supplement the carbon source required in the product and comprises no other doping atoms can be used, and non-volatile organic compounds are preferred. More preferably, the mass ratio of said other organic compound(s) to the transition metal source in the mixture is about 0-10:1, and still more preferably about 0-3:1.

In a preferred embodiment, the transition metal is one or more selected from the group consisting of iron, cobalt, nickel, copper and zinc, more preferably one or more of iron, cobalt, nickel and copper, most preferably nickel.

In a preferred embodiment, the transition metal source is one or more selected from the group consisting of organic acid salts, carbonates, basic carbonates, oxides and hydroxides of transition metals.

The organic acid salt of the transition metal is not particularly limited in the present application as long as it can be mixed with the polybasic organic carboxylic acid in the solvent to form a homogeneous solution. For example, the organic acid salt of the transition metal includes, but not limited to, heteroatom-free organic carboxylates of the transition metal, such as acetates and the like.

The polybasic organic carboxylic acid is not particularly limited in the present application as long as it can be mixed with the organic acid salt of the transition metal in the solvent to form a homogeneous solution. The polybasic organic carboxylic acid may be a nitrogen-containing or nitrogen-free polybasic organic carboxylic acid, and in the case of a nitrogen-containing polybasic organic carboxylic acid, it may correspond to a combination of a nitrogen-free polybasic organic carboxylic acid and a nitrogen-containing organic compound. In other words, when the polybasic organic carboxylic acid used is a nitrogen-containing polybasic organic carboxylic acid, there is no need to additionally introduce a nitrogen-containing organic compound, and such an embodiment is also within the scope of the present application.

In a preferred embodiment, the polybasic organic carboxylic acid is one or more selected from the group consisting of citric acid, maleic acid, trimesic acid, terephthalic acid, malic acid, EDTA and dipicolinic acid. Further preferably, the dipicolinic acid may be 2,3-dipicolinic acid, 2,4-dipicolinic acid, 2,5-dipicolinic acid, 2,6-dipicolinic acid, 3,4-dipicolinic acid and/or 3,5-dipicolinic acid.

In certain preferred embodiments, the mixture used in step i) comprises a transition metal source and a nitrogen-containing polybasic organic carboxylic acid, and optionally an oxygen-containing organic compound and/or other organic compound(s).

In a particularly preferred embodiment, the polybasic organic carboxylic acid includes, but not limited to, citric acid, the nitrogen-containing polybasic organic carboxylic acid includes, but not limited to, ethylenediaminetetraacetic acid (EDTA), the transition metal source includes, but not limited to, an acetate of the transition metal, the nitrogen-containing organic compound includes, but not limited to, hexamethylenetetramine, and the oxygen-containing organic compound includes, but not limited to, an organic polyol.

In a preferred embodiment, the solvent used in step i) is one or more selected from the group consisting of water, methanol, ethanol, n-propanol and isopropanol, more preferably selected from water, ethanol or a combination thereof, most preferably water.

In a preferred embodiment, in step ii), the solvent may be removed, for example, by evaporation, for example by spray drying at 80-120° C., or by drying in an oven.

In step ii) of the method according to the present application, the precursor obtained after removal of the solvent may be a mixture, and the mixture may be water-soluble.

In a preferred embodiment, in step iii), the inert protective atmosphere is nitrogen or argon, and the reducing atmosphere is a mixed gas of an inert gas and hydrogen; the high-temperature pyrolysis process comprises a temperature-rising stage and a temperature-sustaining stage, wherein in the temperature-rising stage the temperature is raised at a heating rate of about 0.5-30° C./min to the level employed at the temperature-sustaining stage, and the temperature is kept constant at the temperature-sustaining stage for about 20-600 min, with the temperature employed at the temperature-sustaining stage being about 400-800° C. More preferably, the heating rate adopted in the temperature-rising stage is about 0.5-10° C./min, further preferably about 1-10° C./min, particularly preferably about 2.5-10° C./min, most preferably about 1-5° C./min; the temperature is kept constant at the temperature-sustaining stage for about 30-480 min, further preferably for about 60-300 min; and the temperature employed at the temperature-sustaining stage is about 500-800° C., further preferably about 500-700° C.

In a preferred embodiment, the non-oxidizing strong acid used in step iv) includes, but not limited to, hydrofluoric acid, hydrochloric acid, nitric acid and sulfuric acid, or a combination of any two or more of them, preferably hydrochloric acid and/or sulfuric acid.

In a further preferred embodiment, the acid treatment of step iv) is carried out at a temperature of about 30-100° C. for at least about 1 hour, preferably at a temperature of about 60-100° C. for about 1-20 h, more preferably at a temperature of about 70-90° C. for about 1-10 h.

In a particular embodiment, the transition metal element is present in a reduced state (e.g., zero-valent state) in the nanocomposite material prepared by the method according to the present application, i.e., there is no transition metal element present in an oxidized state (e.g., oxide).

In certain preferred embodiments, the method for preparing a nanocomposite material according to the present application comprises the steps of:

i) mixing a transition metal source, a polybasic organic carboxylic acid, optionally a nitrogen-containing organic compound, optionally an oxygen-containing organic compound, and optionally other organic compound(s) in a solvent selected from the group consisting of water and ethanol to form a homogeneous solution;

ii) removing the solvent by evaporation to obtain a water-soluble mixture comprising the transition metal;

iii) subjecting the water-soluble mixture to high-temperature pyrolysis under an inert or reducing atmosphere; and iv) optionally, subjecting the product obtained by high-temperature pyrolysis to a treatment with an acid.

In a further preferred embodiment, the method and conditions employed for removing the solvent by evaporation can be any available technology known in the art, for example spray drying at about 80-120° C., or drying in an oven.

In a further preferred embodiment, the transition metal source, the nitrogen-free polybasic organic carboxylic acid, the nitrogen-containing organic compound, the optional oxygen-containing organic compound and the optional additional organic compound(s) are mixed in step i) in a solvent.

In a further preferred embodiment, the transition metal source, the nitrogen-containing polybasic organic carboxylic acid, the optional oxygen-containing organic compound and the optional additional organic compound(s) are mixed in step i) in a solvent.

As compared with the prior art, the method for the preparation of the nanocomposite material is simple and efficient, the precursor subjected to high-temperature pyrolysis is obtained by directly mixing the transition metal source, the polybasic organic carboxylic acid, the optional nitrogen-containing organic compound, the optional oxygen-containing organic compound and the optional additional organic compound(s) in an aqueous solution, so that the atom utilization of the transition metal in the precursor obtained can be 100%, and the following defects of the prior art for preparing the precursor having a metallic organic framework structure can be overcome, i.e. the need for a high-temperature and high-pressure reaction kettle in the self-assembly reaction, the waste of a large amount of precursor of carbon source, the consumption of a large amount of organic solvent, the complexity in purification and the like.

The method according to the present application does not require the formation of a metal-organic framework compound, and allows easy adjustment of the content of the doping element in the graphitized carbon layer during the preparation, so that the catalytic performance of the nanocomposite material can be conveniently adjusted for different catalytic reactions.

In addition, it is hard to prepare a nano-scale core-shell structure having a tightly wrapped graphitized carbon layer and a transition metal core in the prior art, especially in case where it is required to form a composite material having both a tightly wrapped core-shell structure and a structure rich in mesopores. The method according to the present application can not only fulfil the purposes, but also provide a composite material having both a tightly wrapped core-shell structure and a multilevel mesoporous structure rich in mesopores.

In a fourth aspect, the present application also provides a nanocomposite material comprising carbon-coated transition metal particles prepared by the method according to the present application.

In a particular embodiment, the carbon-coated transition metal particles of the nanocomposite material prepared by the method according to the present application have a core-shell structure, in which the shell layer is a graphitized carbon layer doped with oxygen and/or nitrogen, and the core is a transition metal nanoparticle. Preferably, the carbon-coated transition metal particles have a spherical or quasi-spherical shape and have a particle size of about 1 nm to about 200 nm, preferably about 3 nm to about 100 nm, and more preferably about 4 nm to about 50 nm.

In a particular embodiment, the transition metal element is present in a reduced state (e.g., zero-valent state) in the nanocomposite material prepared by the method according to the present application, i.e., there is no transition metal element present in an oxidized state (e.g., oxide).

In a preferred embodiment, the nanocomposite material prepared by the method according to the present application further comprises an amorphous carbon matrix, the carbon-coated transition metal particles being dispersed in the amorphous carbon matrix; more preferably, the nanocomposite material is consisted of an amorphous carbon matrix and carbon-coated transition metal particles dispersed therein.

In a preferred embodiment, the nanocomposite material has at least one distribution peak of mesopores, preferably two or more distribution peaks of mesopores.

In a preferred embodiment, the nanocomposite material has a proportion of mesopore volume to total pore volume of greater than about 50%, more preferably greater than about 80%, even more preferably greater than about 90%, particularly preferably greater than about 95%, and most preferably about 100%.

In a preferred embodiment, the nanocomposite material has a loss on acid leaching of 40% or less, more preferably 30% or less, and particularly preferably 10% or less.

In a preferred embodiment, the transition metal nanoparticles have a face-centered-cubic lattice structure and/or a hexagonal-close-packed lattice structure.

In certain preferred embodiments, the nanocomposite material has the characteristics as described above for the nanocomposite material according to the first aspect of the present application.

In certain preferred embodiments, the nanocomposite material has the characteristics as described above for the nanocomposite material according to the second aspect of the present application.

As can be seen from the transmission electron microscope test, the nanocomposite material prepared by the method according to the present application does not contain any carbon nanotube.

The nanocomposite material prepared by the method according to the present application has a structure rich in mesopores, which is beneficial to the diffusion of reactants and products, and provides a higher mass transfer efficiency, thereby exhibiting more superior catalytic performance. In some embodiments, the composite material made in a single batch has two distribution peaks within the range of mesopores; and if the composite materials made in a plurality of batches are mixed, more distribution peaks within the range of mesopores can be observed. Where the nanocomposite material has a multilevel mesoporous structure with mesopores having pore sizes within different ranges, the nanocomposite material can provide more unique performance, and can be applied to a wider range of applications.

The nanocomposite material prepared by the method according to the present application is doped with oxygen and/or nitrogen in the graphitized carbon layer, in which the oxygen content can be adjusted by additionally introducing an oxygen-containing organic compound such as polyol during the preparation process, and the nitrogen content can be adjusted by additionally introducing a nitrogen-containing organic compound such as hexamethylenetetramine during the preparation process. The catalytic performance of the carbon layer can be modified by adjusting the contents of nitrogen and oxygen in the nanocomposite material, so that it may be suitable for catalyzing different reactions.

The nanocomposite material prepared by the method according to the present application can be widely used in the fields of catalytic materials, wave-absorbing materials, information storage materials, magneto-optical materials, biomedical materials, lubricating oil additives and the like. In particular, when the transition metal is iron, cobalt, nickel or copper, the composite material can be used as a catalyst for reactions such as the hydrogenation reaction of p-chloronitrobenzene for producing p-chloroaniline, the hydrogenation reaction of nitrobenzene for producing aniline, the hydrogenation reaction of nitrophenol for producing aminophenol, the hydrogenation reaction of p-nitroanisole for producing p-anisidine, the hydrogenation reaction of phenol for producing cyclohexanol, the hydrogenation reaction of olefins, the hydrogenation reaction of aromatic hydrocarbons for producing cyclohexane derivatives, the hydrogenation reaction of aldehydes for producing alcohols, and the hydrogenation reaction of ketones for producing alcohols.

In a fifth aspect, the present application also provides the use of a nanocomposite material according to the present application as a catalyst in the treatment of volatile organic compounds, comprising: contacting a volatile organic compound with the nanocomposite material to conduct a catalytic oxidation reaction.

In a preferred embodiment, the volatile organic compound is a volatile organic compound contained in industrial exhaust gases.

In a preferred embodiment, the volatile organic compound comprises butane, and the butane accounts for about 0.01% to about 2% by volume of the industrial exhaust gas.

In a preferred embodiment, the catalytic oxidation reaction is carried out at a temperature of about 200-500° C., more preferably at a temperature of about 300-400° C., and even more preferably at a temperature of about 350-400° C.

In a further preferred embodiment, the reaction space velocity of the catalytic oxidation reaction is about 2000 ml to about 5000 ml industrial exhaust gas/(hr·g of the catalyst).

In a preferred embodiment, the industrial exhaust gas is industrial exhaust gas generated during the preparation of maleic anhydride by oxidation of n-butane.

When the nanocomposite material according to the present application is used as a catalyst for catalytic oxidation reaction of volatile organic compounds, the severity of the reaction can be reduced. For example, the butane component present in an amount of about 0.01-2 vol % in the exhaust gas generated during the process for producing maleic anhydride can be catalytically oxidized into $CO_2$ at about 350° C. with a removal rate of 90 vol % or more, and the butane component can be completely catalytically oxidized into $CO_2$ at about 400° C. As compared with the prior art, the reaction temperature can be reduced, the reaction space velocity can be increased, etc., so that a complete oxidation of the butane present at low concentration in the exhaust gas generated during chemical production processes can be achieved at a lower temperature, and thus the present invention has a good prospect of industrial application.

In a sixth aspect, the present application also provides the use of a nanocomposite material according to the present application as a catalyst in a hydrogenation reduction reaction.

In a preferred embodiment, the hydrogenation reduction reaction is selected from the group consisting of the hydrogenation reaction of p-chloronitrobenzene for producing p-chloroaniline, the hydrogenation reaction of nitrobenzene for producing aniline, the hydrogenation reaction of nitrophenol for producing aminophenol, the hydrogenation reaction of p-nitroanisole for producing p-anisidine, the hydrogenation reaction of phenol for producing cyclohexanol, the hydrogenation reaction of olefins, the hydrogenation reaction of aromatic hydrocarbons for producing cyclohexane derivatives, the hydrogenation reaction of aldehydes for producing alcohols, and the hydrogenation reaction of ketones for producing alcohols.

In the nanocomposite material according to the present application, the transition metal core is tightly wrapped by the graphitized carbon layer, so that the security of the nanocomposite material during transportation and usage can be ensured. In addition, the graphitized carbon layer of the nanocomposite material has excellent capability of catalyzing the hydrogenation reduction reaction of organic compounds, which is beneficial to a further improvement of the catalytic performance of the composite material.

In certain preferred embodiments, the present application provides the following technical solutions:

A1. A nanocomposite material comprising carbon-coated transition metal particles, the carbon-coated transition metal particles having a core-shell structure, the shell layer being a graphitized carbon layer doped with oxygen, and the core being a transition metal nanoparticle, wherein the nanocomposite material is a porous material having at least one distribution peak of mesopores.

A2. The nanocomposite material of Item A1, wherein the nanocomposite material is a porous material having two or more distribution peaks of mesopores.

A3. The nanocomposite material of Items A1 or A2, wherein the proportion of mesopore volume to total pore volume of the porous material is greater than about 50%, preferably greater than about 80%.

A4. The nanocomposite material of any one of Items A1-A3, wherein the mesopore volume of the nanocomposite material is about 0.05-1.25 $cm^3/g$.

A5. The nanocomposite material of any one of Items A1-A4, wherein the nanocomposite material has a loss on acid leaching of 40% or less.

A6. The nanocomposite material of any one of Items A1-A5, wherein the nanocomposite material has a carbon content of about 10.0% to about 60.0% by mass and a transition metal content of about 30.0% to about 85.0% by mass; particularly, the carbon content can be about 15.0% to about 40.0% and the transition metal content can be about 50.0% to about 80.0%.

A7. The nanocomposite material of any one of Items A1-A6, wherein the nanocomposite material has an oxygen content of less than about 15.0% by mass, preferably about 0.2-5.0%.

A8. The nanocomposite material of any one of Items A1-A7, wherein the graphitized carbon layer has a thickness of about 0.3-6 nm, preferably about 0.3-3 nm.

A9. The nanocomposite material of any one of Items A1-A8, wherein the core-shell structure has a particle size of about 1-200 nm, preferably about 3-100 nm, more preferably about 4-50 nm.

A10. The nanocomposite material of any one of Items A1-A9, wherein the transition metal is one or more selected from iron, cobalt, nickel, copper, and zinc.

B1. A nanocomposite material comprising carbon-coated transition metal particles, the carbon-coated transition metal particles having a core-shell structure, the shell layer being a graphitized carbon layer doped with oxygen, and the core being a transition metal nanoparticle, wherein the nanocomposite material has a loss on acid leaching of 10% or less.

B2. The nanocomposite material of Item B1, wherein the nanocomposite material is a porous material having at least one distribution peak of mesopores.

B3. The nanocomposite material of Item B1, wherein the nanocomposite material is a porous material having two or more distribution peaks of mesopores.

B4. The nanocomposite material of any one of Items B1-B3, wherein the proportion of mesopore volume to total pore volume of the porous material is greater than about 50%, preferably greater than about 80%.

B5. The nanocomposite material of any one of Items B1-B4, wherein the mesopore volume of the nanocomposite material is about 0.05-1.25 $cm^3/g$.

B6. The nanocomposite material of any one of Items B1-B5, wherein the nanocomposite material has a carbon content of about 15-60% by mass and a transition metal content of about 30-80% by mass, particularly, the carbon content can be about 30-60% and the transition metal content can be about 30-60%.

B7. The nanocomposite material of any one of Items B1-B6, wherein the nanocomposite material has an oxygen content of less than about 15.0% by mass, preferably about 1.0-10.0%.

B8. The nanocomposite material of any one of Items B1-B7, wherein the graphitized carbon layer has a thickness of about 0.3-6.0 nm, preferably about 0.3-3 nm.

B9. The nanocomposite material of any one of Items B1-B8, wherein the core-shell structure has a particle size of about 1-200 nm, preferably about 3-100 nm, more preferably about 4-50 nm.

B10. The nanocomposite material of any one of Items B1-B9, wherein the transition metal is one or more selected from iron, cobalt, nickel, copper, and zinc, preferably nickel.

C1. A nanocomposite material comprising carbon-coated transition metal particles, the carbon-coated transition metal particles having a core-shell structure, the shell layer being a graphitized carbon layer doped with oxygen and nitrogen, and the core being a transition metal nanoparticle, wherein the nanocomposite material has a loss on acid leaching of 10% or less.

C2. The nanocomposite material of Item C1, wherein the nanocomposite material is a porous material having at least one distribution peak of mesopores.

C3. The nanocomposite material of Item C2, wherein the nanocomposite material is a porous material having two or more distribution peaks of mesopores.

C4. The nanocomposite material of any one of Items C1-C3, wherein the proportion of mesopore volume to total pore volume of the porous material is greater than about 50%, preferably greater than about 80%.

C5. The nanocomposite material of any one of Items C1-C4, wherein the nanocomposite material has a carbon content of about 15-60% by mass and a transition metal content of about 30-80% by mass.

C6. The nanocomposite material of any one of Items C1-05, wherein the nanocomposite material has a total content of nitrogen and oxygen of less than about 15% by mass.

C7. The nanocomposite material of any one of Items C1-C6, wherein the graphitized carbon layer has a thickness of about 0.3-6 nm, preferably about 0.3-3 nm.

C8. The nanocomposite material of any one of Items C1-C7, wherein the core-shell structure has a particle size of about 1-200 nm, preferably about 3-100 nm, preferably about 4-50 nm.

C9. The nanocomposite material of any one of Items C1-C8, wherein the transition metal is one or more selected from iron, cobalt, nickel, copper, and zinc, preferably nickel.

C10. The nanocomposite material of any one of Items C1-C9, wherein the transition metal nanoparticles have a face-centered-cubic lattice structure and/or a hexagonal-close-packed lattice structure.

D1. A nanocomposite material comprising carbon-coated transition metal particles, the carbon-coated transition metal particles having a core-shell structure, the shell layer being a graphitized carbon layer doped with oxygen and nitrogen, and the core being a transition metal nanoparticle, wherein the nanocomposite material is a porous material having at least one distribution peak of mesopores.

D2. The nanocomposite material of Item D1, wherein the nanocomposite material has two or more distribution peaks of mesopores.

D3. The nanocomposite material of Items D1 or D2, wherein the proportion of mesopore volume to total pore volume of the porous material is greater than about 50%, preferably greater than about 80%.

D4. The nanocomposite material of any one of Items D1-D3, wherein the nanocomposite material has a carbon content of about 10.0-60.0% by mass and a transition metal content of about 30.0-85.0% by mass; particularly, the carbon content can be about 30.0-50.0% and the transition metal content can be about 30.0-60.0%.

D5. The nanocomposite material of any one of Items D1-D4, wherein the nanocomposite material has a total content of nitrogen and oxygen of less than about 15.0% by mass, preferably about 0.2-12.0%, more preferably about 0.5-10.0%.

D6. The nanocomposite material of any one of Items D1-D5, wherein the nitrogen content is less than about 15% by mass, preferably about 0.1-10%, more preferably about 1-5%.

D7. The nanocomposite material of any one of Items D1-D6, wherein the nanocomposite material has a loss on acid leaching of 40% or less.

D8. The nanocomposite material of any one of Items D1-D7, wherein the graphitized carbon layer has a thickness of about 0.3-6.0 nm, preferably about 0.3-3 nm.

D9. The nanocomposite material of any one of Items D1-D8, wherein the core-shell structure has a particle size of about 1-200 nm, preferably about 3-100 nm, more preferably about 4-50 nm.

D10. The nanocomposite material of any one of Items D1-D9, wherein the transition metal is one or more selected from iron, cobalt, nickel, copper, and zinc.

D11. The nanocomposite material of any one of Items D1-D10, wherein the transition metal nanoparticles have a face-centered-cubic lattice structure and/or a hexagonal-close-packed lattice structure.

E1. A method for preparing a carbon-coated transition metal nanocomposite material, comprising the steps of:
 i) mixing a mixture comprising a transition metal salt and a polybasic organic carboxylic acid with a solvent to form a homogeneous solution;
 ii) removing the solvent from the homogeneous solution to obtain a precursor; and
 iii) subjecting the precursor to high-temperature pyrolysis under an inert protective atmosphere or a reducing atmosphere.

E2. The method of Item E1, wherein the transition metal is one or more of iron, cobalt, nickel, and copper.

E3. The method of Item E1 or E2, wherein the transition metal salt is one or more of organic acid salts, carbonates, and basic carbonates of transition metal; preferably, the organic acid salt of the transition metal is a heteroatom-free organic carboxylate of the transition metal, such as acetate.

E4. The method of any one of Items E1-E3, wherein the polybasic organic carboxylic acid is one or more of citric acid, maleic acid, trimesic acid, terephthalic acid, malic acid, EDTA, and dipicolinic acid.

E5. The method of any one of Items E1-E4, wherein the mass ratio of the transition metal salt to the polybasic organic carboxylic acid is about 1:0.1-10, preferably about 1:0.5-5, more preferably about 1:0.8-3.

E6. The method of any one of Items E1-E5, wherein the solvent is selected from water, ethanol or a mixture thereof.

E7. The method of any one of Items E1-E6, wherein in the step iii), the inert protective atmosphere is nitrogen or argon, the high-temperature pyrolysis is carried out by heating up to the temperature of a temperature-sustaining stage at a heating rate of about 0.5-30° C./min, and then keeping the temperature constant at the temperature-sustaining stage for about 20-600 min, with the temperature employed at the temperature-sustaining stage being about 400-800° C.; preferably, the heating rate is about 1-10° C./min, the temperature is kept constant at the temperature-sustaining stage for 60-480 min, and the temperature employed at the temperature-sustaining stage is about 500-800° C.

E8. The method of any one of Items E1-E6, wherein the reducing atmosphere is a mixed gas of inert gas and hydrogen, the high-temperature pyrolysis is carried out by heating up to the temperature of a temperature-sustaining stage at a heating rate of about 0.5-30° C./min, and then keeping the temperature constant at the temperature-sustaining stage for about 20-600 min, and the temperature employed at the temperature-sustaining stage is about 400-800° C.; preferably, the heating rate is about 1-10° C./min, the temperature is kept constant at the temperature-sustaining stage for about 60-480 min, and the temperature employed at the temperature-sustaining stage is about 500-800° C.

E9. The method of any one of Items E1-E8, further comprising a step of subjecting the pyrolysis product to a treatment with a non-oxidizing strong acid after said step iii).

E10. A carbon-coated transition metal nanocomposite material prepared by the method according to any one of Items E1-E9.

E11. The nanocomposite material of Item E10, wherein the nanocomposite material has at least one distribution peak of mesopores, preferably two or more distribution peaks of mesopores.

E12. The nanocomposite material of Item E10 or E11, wherein the nanocomposite material has a proportion of mesopore volume to total pore volume of greater than about 50%, preferably greater than about 80%.

E13. The nanocomposite material of any one of Items E10-E12, wherein the nanocomposite material has a loss on acid leaching of 40% or less, preferably 30% or less, more preferably 10% or less.

E14. The nanocomposite material of any one of Items E10-E13, wherein the transition metal nanoparticles have a face-centered-cubic lattice structure and/or a hexagonal-close-packed lattice structure.

F1. A method for preparing a carbon-coated transition metal nanocomposite material, comprising the steps of:
i) mixing a mixture comprising a transition metal salt, a polybasic organic carboxylic acid and a nitrogen-containing organic compound with a solvent to form a homogeneous solution;
ii) removing the solvent from the homogeneous solution to obtain a precursor; and
iii) subjecting the precursor to high-temperature pyrolysis under an inert protective atmosphere or a reducing atmosphere.

F2. The method of Item F1, wherein the transition metal is one or more selected from iron, cobalt, nickel, and copper.

F3. The method of Item F1 or F2, wherein the transition metal salt is one or more of organic acid salts, carbonates, and basic carbonates of the transition metal; preferably, the organic acid salt of the transition metal is a heteroatom-free organic carboxylate of the transition metal, such as acetate.

F4. The method of any one of Items F1-F3, wherein the polybasic organic carboxylic acid is one or more selected from citric acid, maleic acid, trimesic acid, terephthalic acid, malic acid, EDTA, and dipicolinic acid.

F5. The method of any one of Items F1-F4, wherein the nitrogen-containing organic compound is one or more selected from urea, melamine, dicyanodiamine, hexamethylenetetramine, and amino acids.

F6. The method of any one of Items F1-F5, wherein the mass ratio of the transition metal salt, the polybasic organic carboxylic acid, and the nitrogen-containing organic compound is about 1:0.1-100:0.1-100, preferably about 1:0.5-5:0.5-5, more preferably about 1:0.8-2:1-2.

F7. The method of any one of Items F1-F6, wherein the solvent is selected from water, ethanol and mixtures thereof.

F8. The method of any one of Items F1-F7, wherein in the step iii), the inert protective atmosphere is nitrogen or argon, the high-temperature pyrolysis is carried out by heating up to the temperature of a temperature-sustaining stage at a heating rate of about 0.5-30° C./min, the temperature is kept constant at the temperature-sustaining stage for about 20-600 min, and the temperature employed at the temperature-sustaining stage is about 400-800° C.; preferably, the heating rate is about 1-10° C./min, the temperature is kept constant at the temperature-sustaining stage for about 60-480 min, and the temperature employed at the temperature-sustaining stage is about 500-800° C.

F9. The method of any one of Items F1-F7, wherein the reducing atmosphere is a mixed gas of inert gas and hydrogen, the high-temperature pyrolysis is carried out by heating up to the temperature of a temperature-sustaining stage at a heating rate of about 0.5-30° C./min, the temperature is kept constant at the temperature-sustaining stage for about 20-600 min, and the temperature employed at the temperature-sustaining stage is about 400-800° C.; preferably, the heating rate is about 1-10° C./min, and the temperature employed at the temperature-sustaining stage is about 500-800° C.

F10. The method of any one of Items F1-F9, further comprising a step of subjecting the pyrolysis product to a treatment with a non-oxidizing strong acid after said step iii).

F11. A carbon-coated transition metal nanocomposite material prepared by the method of any one of Items F1-F10.

F12. The nanocomposite material of Item F11, wherein the nanocomposite material has at least one distribution peak of mesopores, preferably two or more distribution peaks of mesopores.

F13. The nanocomposite material of Item F11 or F12, wherein the nanocomposite material has a proportion of mesopore volume to total pore volume of greater than about 50%, preferably greater than about 80%.

F14. The nanocomposite material of any one of Items F11-F13, wherein the nanocomposite material has a loss on acid leaching of 40% or less, preferably 30% or less, more preferably 10% or less.

F15. The nanocomposite material of any one of Items F11-F14, wherein the transition metal nanoparticles have a face-centered-cubic lattice structure and/or a hexagonal-close-packed lattice structure.

G1. A method for producing p-chloroaniline by the hydrogenation of p-chloronitrobenzene, comprising a step of subjecting p-chloronitrobenzene to hydrogenation reduction in the presence of a catalyst, wherein a nanocomposite material according to any one of Items A1-A10, B1-B10, C1-C10, D1-D11, E10-E14 and F11-F15 is used as the catalyst.

G2. The method of Item G1, comprising the steps of mixing the catalyst with p-chloronitrobenzene in a solvent, and then subjecting the resultant to hydrogenation reduction, wherein the solvent is one or more selected from the group consisting of alcohols, ethers, alkanes, and water.

G3. The method of Items G1 or G2, wherein the temperature of the hydrogenation reaction is between about 60° C. and about 120° C. and the hydrogen pressure is between about 0.5 MPa and about 2 MPa.

H1. A method for producing aniline by the hydrogenation of nitrobenzene, comprising a step of subjecting nitrobenzene to hydrogenation reduction in the presence of a catalyst, wherein a nanocomposite material according to any one of Items A1-A10, B1-B10, C1-C10, D1-D11, E10-E14 and F11-F15 is used as the catalyst.

H2. The method of Item H1, comprising the steps of mixing the catalyst with nitrobenzene in a solvent, and then subjecting the resultant to hydrogenation reduction, wherein the solvent is one or more selected from the group consisting of alcohols, ethers, alkanes, and water.

H3. The method of Item H1 or H2, wherein the temperature of the hydrogenation reaction is between about 60° C. and about 120° C. and the hydrogen pressure is between about 0.5 MPa and about 2 MPa.

I1. A method for producing aminophenol by the hydrogenation of nitrophenol, comprising a step of subjecting nitrophenol to hydrogenation reduction in the presence of a catalyst, wherein a nanocomposite material according to any one of Items A1-A10, B1-B10, C1-C10, D1-D11, E10-E14 and F11-F15 is used as the catalyst.

I2. The method of Item I1, comprising the steps of mixing the catalyst with nitrophenol in a solvent, and then subjecting the resultant to hydrogenation reduction, wherein the solvent is one or more selected from the group consisting of alcohols, ethers, alkanes and water.

I3. The method of Item I1 or I2, wherein the temperature of the hydrogenation reaction is between about 50° C. and about 120° C. and the hydrogen pressure is between about 0.5 MPa and about 2 MPa.

J1. A method for producing p-anisidine by the hydrogenation of p-nitroanisole, comprising a step of subjecting p-nitroanisole to hydrogenation reduction in the presence of a catalyst, wherein a nanocomposite material according to any one of Items A1-A10, B1-B10, C1-C10, D1-D11, E10-E14 and F11-F15 is used as the catalyst.

J2. The method of Item J1, comprising the steps of mixing the catalyst with p-nitroanisole in a solvent, and then subjecting the resultant to hydrogenation reduction, wherein the solvent is one or more selected from the group consisting of alcohols, ethers, alkanes and water.

J3. The method of Item J1 or J2, wherein the temperature of the hydrogenation reaction is between about 50° C. and about 120° C. and the hydrogen pressure is between about 0.5 MPa and about 2 MPa.

K1. A method for producing cyclohexanol by the hydrogenation of phenol, comprising a step of subjecting phenol to hydrogenation reduction in the presence of a catalyst, wherein a nanocomposite material according to any one of Items A1-A10, B1-B10, C1-C10, D1-D11, E10-E14 and F11-F15 is used as the catalyst.

K2. The method of Item K1, comprising the steps of mixing the catalyst with a phenolic compound in a solvent, and then subjecting the resultant to hydrogenation reduction, wherein the solvent is one or more selected from the group consisting of alcohols, ethers, alkanes and water.

K3. A method of Item K1 or K2, wherein the temperature of the hydrogenation reaction is between about 150° C. and about 250° C. and the hydrogen pressure is between about 3 MPa and about 6 MPa.

L1. A method for the hydrogenation of olefins, comprising a step of subjecting an olefin to hydrogenation reduction in the presence of a catalyst, wherein a nanocomposite material according to any one of Items A1-A10, B1-B10, C1-C10, D1-D111, E10-E14 and F11-F15 is used as the catalyst.

L2. The method of Item L1, comprising the steps of mixing the catalyst with the olefin in a solvent, and then subjecting the resultant to hydrogenation reduction, wherein the solvent is one or more selected from the group consisting of alcohols, ethers, alkanes, and water.

L3. The method of Item L1 or L2, wherein the temperature of the hydrogenation reaction is between about 100° C. and about 130° C. and the hydrogen pressure is between about 1 MPa and about 3 MPa.

M1. A method for producing cyclohexane derivatives by the hydrogenation of aromatic hydrocarbons, comprising a step of subjecting an aromatic hydrocarbon to hydrogenation reduction in the presence of a catalyst, wherein a nanocomposite material according to any one of Items A1-A10, B1-B10, C1-C10, D1-D11, E10-E14 and F11-F15 is used as the catalyst.

M2. The method of Item M1, comprising the steps of mixing the catalyst with the aromatic hydrocarbon in a solvent, and then subjecting the resultant to hydrogenation reduction, wherein the solvent is one or more selected from the group consisting of alcohols, ethers, alkanes, and water.

M3. The method of Item M1 or M2, wherein the temperature of the hydrogenation reaction is between about 200° C. and about 300° C. and the hydrogen pressure is between about 3 MPa and about 6 MPa.

N1. A method for producing an alcohol by the hydrogenation of an aldehyde, comprising a step of subjecting the aldehyde to hydrogenation reduction in the presence of a catalyst, wherein a nanocomposite material according to any one of Items A1-A10, B1-B10, C1-C10, D1-D11, E10-E14 and F11-F15 is used as the catalyst.

N2. The method of Item N1, comprising the steps of mixing the catalyst with the aldehyde in a solvent, and then subjecting the resultant to hydrogenation reduction, wherein the solvent is one or more selected from the group consisting of alcohols, ethers, alkanes, and water.

N3. The method according to Item N1 or N2, wherein the temperature of the hydrogenation reaction is between about 80° C. and about 180° C. and the hydrogen pressure is between about 2 MPa and about 5 MPa.

O1. A method for producing an alcohol by the hydrogenation of a ketone, comprising a step of subjecting the ketone to hydrogenation reduction in the presence of a catalyst, wherein a nanocomposite material according to any one of Items A1-A10, B1-B10, C1-C10, D1-D11, E10-E14 and F11-F15 is used as the catalyst.

O2. The method of Item O1, comprising the steps of mixing the catalyst with the ketone in a solvent, and then subjecting the resultant to hydrogenation reduction, wherein the solvent is one or more selected from the group consisting of alcohols, ethers, alkanes, and water.

O3. The method of Item O1 or O2, wherein the temperature of the hydrogenation reaction is between about 100° C. and about 200° C. and the hydrogen pressure is between about 3 MPa and about 6 MPa.

P1. A method for treating volatile organic compounds, comprising a step of subjecting a volatile organic compound to catalytic oxidation in the presence of a catalyst, wherein a nanocomposite material of any one of Items A1-A10, B1-B10, C1-C10, D1-D11, E10-E14 and F11-F15 is used as the catalyst.

P2. The method of Item P1, wherein the volatile organic compound is a volatile organic compound contained in an industrial exhaust gas, particularly an industrial exhaust gas from the production of maleic anhydride by the oxidation of n-butane.

P3. The method of Item P2, wherein the volatile organic compound comprises butane, and the volume percentage of butane in the industrial exhaust gas is about 0.01-2%.

P4. The method of Item P2 or P3, wherein the temperature of the catalytic oxidation reaction is between about 200° C. and about 500° C., preferably about 350° C. and about 400° C., and the space velocity of the reaction is between about 2000 ml and about 5000 ml of industrial exhaust gas/(hr·g of said catalyst).

Q1. A method for reducing organic compounds by catalytic hydrogenation, comprising a step of subjecting an organic compound to catalytic hydrogenation reduction by using a catalyst with a core-shell structure and using hydrogen as a reducing agent, wherein the shell layer of the core-shell structure is a graphitized carbon layer, the core is a transition metal, and the core is tightly wrapped by the graphitized carbon layer.

Q2. The method of Item Q1, wherein the organic compound is an organic compound comprising one or any combination of the following functional groups: nitro group, carbonyl group and carbon-carbon double bonds.

Q3. The method of Item Q1 or Q2, wherein there is more than one distribution peak (e.g. two distribution peaks) within the mesopore range on the pore-size distribution diagram of the catalyst.

Q4. The method of any one of Items Q1-Q3, wherein the transition metal is one of iron, cobalt, nickel, copper and zinc, or any combination thereof.

Q5. A method for reducing organic compounds by catalytic hydrogenation, comprising a step of subjecting an organic compound to catalytic hydrogenation reduction by using a catalyst with a core-shell structure and using hydrogen as a reducing agent, wherein the shell layer of the core-shell structure is a graphitized carbon layer, the core is a transition metal, and there is more than one distribution peak within the mesopore range on the pore-size distribution diagram of the catalyst.

Q6. The method of Item Q5, wherein the organic compound is an organic compound comprising one or any combination of the following functional groups: nitro group, carbonyl group and carbon-carbon double bonds.

Q7. The method of Item Q5 or Q6, wherein there are two distribution peaks within the mesopore range on the pore-size distribution diagram of the catalyst.

Q8. The method of any one of Items Q5-Q7, wherein the transition metal is one of iron, cobalt, nickel, copper and zinc, or any combination thereof.

Q9. A method for producing aniline by the catalytic hydrogenation reduction of nitrobenzene, comprising a step of subjecting nitrobenzene to catalytic hydrogenation reduction by using the method according to any of Items Q1-Q8.

Q10. A method for producing haloaniline by the catalytic hydrogenation reduction of halonitrobenzene, comprising a step of subjecting a halonitrobenzene to catalytic hydrogenation reduction by using the method according to any of Items Q1-Q8.

Q11. A method for producing aminophenols by the catalytic hydrogenation reduction of nitrophenols, comprising a step of subjecting a nitrophenol to catalytic hydrogenation reduction by using the method according to any of Items Q1-Q8.

Q12. A method for producing aminoanisole by the catalytic hydrogenation reduction of nitroanisole, comprising a step of subjecting nitroanisole to catalytic hydrogenation reduction by using the method according to any of Items Q1-Q8.

Q13. A composite material of carbon and transition metal having a core-shell structure, wherein the shell layer of the core-shell structure is a graphitized carbon layer, the core is a transition metal, and there is more than one distribution peak within the mesopore range on the pore-size distribution diagram of the composite material.

Q14. The composite material of Item Q13, wherein there are two distribution peaks (e.g., two distribution peaks at 1-7 nm and 8-16 nm, respectively) within the mesopore range on the pore-size distribution diagram of the composite material.

Q15. The composite material of Item Q13 or Q14, wherein the particle size of the transition metal can be within any range formed between any two integer values from 1 nm to 200 nm (such as the ranges formed between any two values selected from 1, 5, 10, 15, 20, 25, 30, 40, 50, 60, 70, 80, 90, 100, 110, 120, 130, 140, 150, 160, 170, 180, 190, and 200).

Q16. The composite material of any one of Items Q13-Q15, wherein the transition metal is one of iron, cobalt, nickel, copper and zinc, or any combination thereof.

Q17. Use of a composite material of any one of Items Q13-Q16 in the catalytic hydrogenation reduction of organic compounds.

Q18. The use of Item Q17, wherein the organic compound is an organic compound comprising one or any combination of the following functional groups: nitro group, carbonyl group and carbon-carbon double bonds.

The present application will be further illustrated by the following working examples, but is not to be construed as being limited thereto.

Reagents, Instruments and Tests

Unless otherwise indicated, all reagents used in the present application are of analytical grade, and all reagents used are commercially available, for example from Sigma-Aldrich.

In the present application, the XRD diffractometer used was XRD-6000 X-ray powder diffractometer, Shimadzu, Japan. The XRD test was carried out under the following conditions: Cu target, Kα radiation (wavelength λ=0.154 nm), tube voltage of 40 kV, tube current of 200 mA, scanning speed of 10° (2θ)/min.

In the present application, the average particle size of the transition metal particles was obtained by calculating, after peak separation of the XRD pattern, using the Scherrer formula: $D=k\gamma/(B\cdot\cos\theta)$, in which k represents the Scherrer constant, i.e. k=0.89; B represents the half-height width; θ represents the diffraction angle, with unit being radian (rad); γ represents the wavelength of the X-ray, i.e. 0.154054 nm.

In the present application, the surface morphology of the material was characterized using Scanning Electron Microscopy (SEM). The scanning electron microscope used was Hitachi S-4800 Cold Field Emission Scanning Electron Microscope, and the testing conditions of the scanning electron microscope were as follows: fixing the powder sample on a sample table through conductive adhesive for observation, the accelerating voltage being 5 kV.

In the present application, the high-resolution transmission electron microscope (HRTEM) used was JEM-2100 (HRTEM) (Nippon electronics Co., Ltd.). The test conditions for the high-resolution transmission electron microscope were as follows: an acceleration voltage of 200 kV.

In the present application, the X-ray photoelectron spectrometer (XPS) used was ESCALab220i-XL X-ray Electron Spectrometer manufactured by VG scientific Inc. and equipped with Avantage V5.926 software. The test conditions for the X-ray photoelectron spectroscopy analysis were as follows: an excitation source of monochromatized A1Kα X-ray, power of 330 W, and base vacuum of $3\times10^{-9}$ mbar during analytical test. In addition, the electron binding energy was calibrated using the C1s peak (284.6 eV), and the subsequent peak separation was carried out using the XPSPEAK software.

In the present application, for the nanocomposite material in which the shell layer of the carbon-coated transition metal particle is a graphitized carbon layer doped with oxygen, the analysis of the three elements of carbon (C), hydrogen (H) and oxygen (O) was performed on an Elementar Micro Cube elemental analyzer. The operation and conditions were as follows: 1-2 mg of sample was weighed in a tin cup, placed in an automatic sample feeding disc, and fed into a combustion tube through a ball valve for combustion, in which the combustion temperature was 1000° C. (for eliminating the atmospheric interference during sample feeding, helium purge was performed), and then the combusted gas was reduced using reduced copper to form carbon dioxide and water. The mixed gas was separated by two desorption columns and the resultants were sequentially sent to a TCD detector for detection. The analysis of oxygen element was conducted by converting oxygen in the sample into CO in the presence of a carbon catalyst via pyrolysis, and then detecting the CO by TCD. Because the composite material only comprises carbon, hydrogen, oxygen and metal elements, the total content of the metal elements can be obtained base on the total content of carbon, hydrogen and oxygen.

In the present application, for the nanocomposite material in which the shell layer of the carbon-coated transition metal particle is a graphitized carbon layer doped with oxygen and nitrogen, the analysis of the four elements of carbon (C), hydrogen (H), oxygen (O) and nitrogen (N) was also performed on an Elementar Micro Cube elemental analyzer. The operation and conditions were as follows: 1-2 mg of sample was weighed in a tin cup, placed in an automatic sample feeding disc, and fed into a combustion tube through a ball valve for combustion, in which the combustion temperature was 1000° C. (for eliminating the atmospheric interference during sample feeding, helium purge was performed), and then the combusted gas was reduced using reduced copper to form nitrogen, carbon dioxide and water. The mixed gas was separated by three desorption columns and the results were sequentially sent to a TCD detector for detection. The analysis of oxygen element was conducted by converting oxygen in the sample into CO in the presence of a carbon catalyst via pyrolysis, and then detecting the CO by TCD. Because the composite material only comprises carbon, hydrogen, oxygen, nitrogen and metal elements, the total content of the metal elements can be obtained based on the total content of carbon, hydrogen, oxygen and nitrogen.

In the present application, the ratio between different metal elements was determined by X-ray Fluorescence Spectroscopy (XRF), and the contents of different metal elements in the composite material were calculated based on the known total content of carbon, hydrogen, oxygen and nitrogen (if present) elements. The X-ray fluorescence spectrometer (XRF) used in the present application was Rigaku 3013 X-ray Fluorescence Spectrometer. The test conditions for the X-ray fluorescence spectrum analysis were as follows: a scanning time of 100 s and an atmosphere of air.

In the present application, the pore structure properties of the sample were determined by a Quantachrome AS-6B analyzer, the specific surface area and pore volume were obtained using the Brunauer-Emmett-Taller (BET) method, and the pore-size distribution curve was obtained via calculation from the desorption curve in accordance with the Barrett-Joyner-Halenda (BJH) method.

In the present application, the composition of the gas was obtained by on-line gas chromatography using Agilent GC 7890B Chromatogram with an accuracy of $10^{-6}$. The test gas was introduced into the chromatogram from the sample inlet, and separated by the chromatographic column, and the percentage of each gas component was calculated by integration of each chromatographic peak.

In the present application, the "loss on acid leaching" was measured and calculated in the following manner:

The sample was added to an aqueous sulfuric acid solution at a ratio of 1 g sample per 20 mL of sulfuric acid solution (1 mol/L), treated at 90° C. for 8 h, washed with deionized water till neutral, dried, weighed and then analyzed. The loss on acid leaching was calculated as follows:

Loss on acid leaching=[1−(mass fraction of transition metal in the composite material after acid leaching×mass of the composite material after acid leaching)÷(mass fraction of transition metal in the composite material to be subjected to acid leaching×mass of the composite material to be subjected to acid leaching)]×100%.

PREPARATION EXAMPLES AND COMPARATIVE EXAMPLES

Part I

Example 1-1

10 g of nickel acetate and 10 g of citric acid were weighed, added into 30 mL of deionized water, stirred at 70° C. to obtain a homogeneous solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 100 mL/min, heated to 650° C. at a heating rate of 5° C./min, kept at the temperature for 2 h, and then the heating was stopped. The resultant was cooled to room temperature in a nitrogen atmosphere to obtain a carbon-coated nickel nanocomposite material.

Example 1-2

10 g of nickel acetate and 20 g of citric acid were weighed, added into 50 mL of deionized water, stirred at 80° C. to obtain a homogeneous solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 150 mL/min, heated to 600° C. at a heating rate of 5° C./min, kept at the temperature for 2 h, and then the heating was stopped. The resultant was cooled to room temperature in a nitrogen atmosphere to obtain a carbon-coated nickel nanocomposite material.

Example 1-3

10 g of cobalt acetate and 30 g of citric acid were weighed, added into 50 mL of deionized water, stirred at 80° C. to obtain a homogeneous solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 150 mL/min, heated to 600° C. at a heating rate of 5° C./min, kept at the temperature for 2 h, and then the heating was stopped. The resultant was cooled to room temperature in a nitrogen atmosphere to obtain a carbon-coated cobalt nanocomposite material.

Example 1-4

10 g of nickel acetate, 10 g of citric acid and 3 g of maleic acid were weighed, added into 50 mL of deionized water, stirred at 60° C. to obtain a homogeneous solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 100 mL/min, heated to 550° C. at a heating rate of 3° C./min, kept at the temperature for 8 h, and then the heating was stopped. The resultant was cooled to room temperature in a nitrogen atmosphere to obtain a carbon-coated nickel nanocomposite material.

Example 1-5

10 g of nickel acetate, 7 g of citric acid and 5 g of pentaerythritol were weighed, added into 150 mL of deionized water, stirred at 60° C. to obtain a homogeneous solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 100 mL/min, heated to 600° C. at a heating rate of 6° C./min, kept at the temperature for 1 h, and then the heating was stopped. The resultant was cooled to room temperature in a nitrogen atmosphere to obtain a carbon-coated nickel nanocomposite material.

Example 1-6

5 g of nickel acetate, 5 g of cobalt acetate and 16.83 g of citric acid were weighed, added into a beaker containing 30 mL of deionized water, stirred at 80° C. to obtain a homogeneous solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 150 mL/min, heated to 500° C. at a heating rate of 5° C./min, kept at the temperature for 2 h, and then the heating was stopped. The resultant was cooled to room temperature in a nitrogen atmosphere to obtain a carbon-coated nickel-cobalt nanocomposite material.

Example 1-7

10 g of nickel acetate and 20 g of ethylene diamine tetraacetic acid were weighed, added into 150 mL of deionized water, stirred at 60° C. to obtain a mixed solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 100 mL/min, heated to 600° C. at a heating rate of 4° C./min, kept at the temperature for 2 h, and then the heating was stopped. The resultant was cooled to room temperature in a nitrogen atmosphere to obtain a carbon-coated nickel nanocomposite material.

Example 1-8

10 g of nickel acetate and 10 g of terephthalic acid were weighed, added into 30 mL of deionized water, stirred at 70° C. to obtain a homogeneous solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 100 mL/min, heated to 650° C. at a heating rate of 5° C./min, kept at the temperature for 2 h, and then the heating was stopped. The resultant was cooled to room temperature in a nitrogen atmosphere to obtain a carbon-coated nickel nanocomposite material.

Example 1-9

10 g of nickel acetate and 8 g of dipicolinic acid were weighed, added into 150 mL of deionized water, stirred at 60° C. to obtain a mixed solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 100 mL/min, heated to 600° C. at a heating rate of 4° C./min, then hydrogen was introduced at a flow rate of 30 mL/min, kept at the temperature for 2 h, the introduction of hydrogen was shut down, and the heating was stopped. The resultant was cooled to room temperature in a nitrogen atmosphere to obtain a carbon-coated nickel nanocomposite material.

Example 1-10

The process of Example 1-1 was repeated, and an acid treatment was performed after the process of Example 1-1. That is, 2 g of the material obtained in Example 1-1 was added to 40 mL of an aqueous sulfuric acid solution (1 mol/L), treated at 90° C. for 8 h, and then washed with deionized water until neutral to obtain a tightly-wrapped carbon-coated nickel nanocomposite material.

Comparative Example 1-1

A carbon-coated nano-nickel nanocomposite material was prepared by the method disclosed in RSC Advances, 2017, 7, 1531-1539.

1 g of nickel chloride hexahydrate was weighed and dissolved in 58 mL of N,N-dimethylformamide (DMF), and 2 g of terephthalic acid was weighed and dissolved in 15 mL of N,N-dimethylformamide (DMF). Then, the DMF solution of nickel chloride was slowly added dropwise to the DMF solution of terephthalic acid and stirred at room temperature for 1 h. The mixed solution was transferred into an autoclave, reacted at 120° C. for 16 h, and cooled to obtain green precipitate. The resultant was washed with DMF for 3 times, dried at 70° C., and the solid was ground to obtain a precursor.

The precursor was placed in a porcelain boat, then the porcelain boat was placed in the constant-temperature zone of a tube furnace, nitrogen was introduced at a flow rate of 40 mL/min, heated to 600° C. at a heating rate of 10° C./min, kept at the temperature for 1 h, and then the heating was stopped. The resultant was cooled to room temperature in a nitrogen atmosphere to obtain a carbon-coated nickel nanocomposite material.

Comparative Example 1-2

The process of Example 1-7 was repeated, except that 20 g of disodium ethylenediaminetetraacetate was used in place of the 20 g of ethylenediaminetetraacetic acid.

Comparative Example 1-3

The process of Example 1-1 was repeated, except that 10 g of nickel nitrate was used in place of the 10 g of nickel acetate.

Comparative Example 1-4

10 g of nickel acetate solid was placed in a porcelain boat, then the porcelain boat was placed in the constant-temperature zone of a tube furnace, nitrogen was introduced at a flow rate of 150 mL/min, heated to 600° C. at a heating rate of 5° C./min, kept at the temperature for 2 h, and then the heating was stopped. The resultant was cooled to room temperature in a nitrogen atmosphere to obtain a sample material.

Characterization of the Resulting Material

The contents by mass of the elements contained in the materials obtained in Example 1-1 to Example 1-10 are shown in Table 1-1.

TABLE 1-1

Contents of elements in the materials obtained in Examples

| Example No. | Carbon (wt %) | Hydrogen (wt %) | Oxygen (wt %) | Nickel (wt %) | Cobalt (wt %) | Nitrogen (wt %) |
|---|---|---|---|---|---|---|
| Ex. 1-1 | 24.29 | 0.47 | 0.96 | 74.28 | — | — |
| Ex. 1-2 | 35.64 | 0.78 | 3.81 | 59.77 | — | — |
| Ex. 1-3 | 46.48 | 0.42 | 1.11 | — | 51.99 | — |
| Ex. 1-4 | 31.2 | 0.46 | 1.01 | 67.33 | — | — |
| Ex. 1-5 | 29.68 | 0.62 | 1.51 | 68.19 | — | — |
| Ex. 1-6 | 34.28 | 0.85 | 4.21 | 29.74 | 30.92 | — |
| Ex. 1-7 | 42.78 | 0.79 | 2.11 | 51.71 | — | 2.61 |
| Ex. 1-8 | 29.34 | 0.23 | 0.56 | 69.87 | — | — |
| Ex. 1-9 | 28.4 | 1.26 | 2.78 | 64.32 | — | 3.24 |
| Ex. 1-10 | 44.87 | 0.99 | 1.81 | 52.33 | — | — |

The materials obtained in Examples 1-1 to 1-10 and Comparative Examples 1-1 to 1-4 were subjected to acid leaching, and the loss on acid leaching is shown in Table 1-2.

TABLE 1-2

Loss on acid leaching of materials obtained in Examples and Comparative Examples

| Example No. | Loss on acid leaching (%) |
|---|---|
| Ex. 1-1 | 36.2 |
| Ex. 1-2 | 13.2 |
| Ex. 1-3 | 9.5 |
| Ex. 1-4 | 9.5 |
| Ex. 1-5 | 28.6 |
| Ex. 1-6 | 23.1 |
| Ex. 1-7 | 12.4 |
| Ex. 1-8 | 29.4 |
| Ex. 1-9 | 25.6 |
| Ex. 1-10 | 0.56 |
| Comp. Ex. 1-1 | 92 |
| Comp. Ex. 1-2 | 100 |
| Comp. Ex. 1-3 | 100 |
| Comp. Ex. 1-4 | 100 |

It can be seen from the data shown in Tables 1-1 and 1-2 that, in the carbon-coated transition metal nanocomposite materials obtained in Examples 1-1 to 1-9 of the present application, the transition metal is wrapped by carbon with a better effect, i.e., most of the metal is tightly wrapped by the carbon layer.

The nanocomposite materials obtained in Examples 1-1 to Examples 1-9 were subjected to an X-ray photoelectron spectroscopy (XPS) test, the results show that the Ni in the composite material is present in a zero valence state, and the O in the nanocomposite material is not present in the form of metal-oxygen (M-O) bond, but only in the form of carboxyl oxygen, carbonyl oxygen and hydroxyl oxygen, which fully demonstrates that the core-shell structure can effectively isolate the highly active Ni nanoparticles from air, and the core-shell structure is complete, so that the nanocomposite material is more suitable for use under severe reaction conditions.

FIG. 1-1 shows an XRD pattern of the precursor obtained in Example 1-1, indicating that the precursor is an amorphous material; FIG. 1-2 is a photograph of the magnetic test of the carbon-coated nickel nanocomposite material obtained in Example 1-1, which shows that a suspension of the carbon-coated nickel nanocomposite material rapidly becomes clear after being attracted by a magnet, indicating that the composite material has strong magnetism; FIG. 1-3 shows a TEM image of the carbon-coated nickel nanocomposite material obtained in Example 1-1, from which it can be seen that the material is a composite material comprising carbon-coated metal particles, and a carbon layer having a certain graphitization degree is coated on the outer surface of the nickel nanoparticle to form a complete core-shell structure. FIG. 1-4 shows an XRD pattern of the carbon-coated nickel nanocomposite material obtained in Example 1-1, from which it can be seen that there are diffraction peaks corresponding to graphite carbon (at $2\theta$ of 26°) and nickel present in a face-centered-cubic structure (fcc-Ni) (at $2\theta$ of 44.5°, 51.7° and 76.4°) in the diffraction pattern of the material, indicating that the material comprises carbon having a certain graphitization degree and nickel present in a face-centered-cubic structure. The average particle size of the carbon-coated nickel nanoparticles is 4.7 nm as calculated by the Scherrer formula. The BET test shows that the specific surface area of the material is 146 $m^2/g$, the pore volume is 0.37 $cm^3/g$, in which the mesopore volume is 0.365 $cm^3/g$, which accounts for 98.6% of the total pore volume. FIG. 1-5A and FIG. 1-5B show an N2 adsorption-desorption isotherm and a BJH pore-size distribution diagram of the material, respectively, from which it can be seen that the composite material has two distribution peaks of mesopores at 3.77 nm and 10.26 nm. In the acid leaching test, the loss on acid leaching of the material was 36.2%. The loss on acid leaching was kept substantially unchanged, where the time of acid leaching was prolonged on the basis of the above-described method.

FIG. 1-6 shows a TEM image of the carbon-coated nickel nanocomposite material obtained in Example 1-2. As can be seen from FIG. 1-6, the material has a core-shell structure with metallic nickel nanoparticle as the core and carbon having a certain graphitization degree as the shell. There are diffraction peaks corresponding to graphitic carbon (at 2θ of 26°) and fcc-Ni (44.5°, 51.9° and 76.2°) in the XRD pattern of the material (FIG. 1-7), indicating that the material comprises carbon having a certain graphitization degree and nickel present in a face-centered-cubic structure. The average particle size of the carbon-coated nickel nanoparticles is 34.5 nm as calculated by the Scherrer formula. The BET test shows that the specific surface area of the material is 137 m$^2$/g, the pore volume is 0.343 cm$^3$/g, in which the mesopore volume is 0.323 cm$^3$/g, which accounts for 94% of the total pore volume. FIG. 1-8 is a diagram showing the pore-size distribution of the carbon-coated nickel nanocomposite material obtained in Example 1-2. As can be seen from FIG. 1-8, two distribution peaks of mesopores are present at 3.85 nm and 11.53 nm on the BJH pore-size distribution curve of the material. In the acid leaching test, the loss on acid leaching of the material was 13.2%. The loss on acid leaching was kept substantially unchanged, where the time of acid leaching was prolonged on the basis of the above-described method.

FIG. 1-9 shows a TEM image of the carbon-coated cobalt nanocomposite material obtained in Example 1-3. As can be seen from FIG. 1-9, the material has a core-shell structure with metallic cobalt nanoparticles as the core and carbon having a certain graphitization degree as the shell. There are diffraction peaks corresponding to graphitic carbon (at 2θ of 26°) and fcc-Co (44.3°, 51.4° and 75.9°) in the XRD pattern of the material (FIG. 1-10), indicating that the material comprises carbon having a certain graphitization degree and cobalt with a face-centered-cubic structure. The average particle size of the carbon-coated cobalt nanoparticles is 24 nm as calculated by the Scherrer formula. The BET test shows that the specific surface area of the material is 192 m$^2$/g, the pore volume is 0.398 cm$^3$/g, in which the mesopore volume is 0.394 cm$^3$/g, which accounts for 99% of the total pore volume. FIG. 1-11 is a diagram showing the pore-size distribution of the carbon-coated cobalt nanocomposite material obtained in Example 1-3. As can be seen from FIG. 1-11, two distribution peaks of mesopores are present at 3.38 nm and 8.98 nm on the BJH pore-size distribution curve of the material. In the acid leaching test, the loss on acid leaching of the material was 9.5%. The loss on acid leaching was kept substantially unchanged, where the time of acid leaching was prolonged on the basis of the above-described method.

FIG. 1-12 shows a TEM image of the carbon-coated nickel nanocomposite material obtained in Example 1-4. As can be seen from FIG. 1-12, the material has a core-shell structure with metallic nickel nanoparticles as the core and carbon having a certain graphitization degree as the shell. In the acid leaching test, the loss on acid leaching of the material was 9.5%. The loss on acid leaching was kept substantially unchanged, where the time of acid leaching was prolonged on the basis of the above-described method.

FIG. 1-13 shows a TEM image of the carbon-coated nickel nanocomposite material obtained in Example 1-5. As can be seen from FIG. 1-13, the material forms a core-shell structure with metallic nickel nanoparticles as the core and carbon having a certain graphitization degree as the shell. In the acid leaching test, the loss on acid leaching of the material was 28.6%. The loss on acid leaching was kept substantially unchanged, where the time of acid leaching was prolonged on the basis of the above-described method.

FIG. 1-14 shows a TEM image of the carbon-coated nickel-cobalt nanocomposite material obtained in Example 1-6. As can be seen from FIG. 1-14, the material has a core-shell structure with metallic nickel or cobalt nanoparticles as the core and carbon having a certain graphitization degree as the shell. There are diffraction peaks corresponding to graphitic carbon (at 2θ of 25.6°), fcc-Ni and fcc-Co (44.3°, 51.7° and 76.0°) in the XRD pattern of the material (FIG. 1-15), indicating that the material comprises carbon having a certain graphitization degree and nickel and cobalt present in a face-centered-cubic structure. The average particle size of the carbon-coated nanoparticles is 39 nm as calculated by the Scherrer formula. The BET test shows that the specific surface area of the material is 159 m$^2$/g, the pore volume is 0.208 cm$^3$/g, in which the mesopore volume is 0.196 cm$^3$/g, which accounts for 94% of the total pore volume. FIG. 1-16 is a diagram showing the pore-size distribution of the carbon-coated nickel-cobalt nanocomposite material obtained in Example 1-6. As can be seen from FIG. 1-16, two distribution peaks of mesopores are present at 3.25 nm and 8.94 nm on the BJH pore-size distribution curve of the material. In the acid leaching test, the loss on acid leaching of the material was 23.1%. The loss on acid leaching was kept substantially unchanged, where the time of acid leaching was prolonged on the basis of the above-described method.

FIG. 1-17 shows a TEM image of the carbon-coated nickel nanocomposite material obtained in Example 1-7. As can be seen from FIG. 1-17, the material has a core-shell structure with metallic nickel nanoparticles as the core and carbon having a certain graphitization degree as the shell. In the XRD pattern of the material (FIG. 1-18), there are diffraction peaks corresponding to graphite carbon (at 2θ of 25.6°), diffraction peaks corresponding to fcc-Ni (44.4°, 51.8° and 76.4°), and diffraction peaks corresponding to nickel present in hexagonal-close-packed structure (hcp-Ni) (at 2θ of 41.9°, 44.7°, 47.5° and 62.6°), indicating that the material comprises carbon having a certain graphitization degree and nickel present in a face-centered-cubic structure and in a hexagonal-close-packed structure. The average particle size of the carbon-coated nickel nanoparticles is 7.2 nm as calculated by the Scherrer formula. The BET test shows that the specific surface area of the material is 228 m$^2$/g, the pore volume is 0.293 cm$^3$/g, in which the mesopore volume is 0.293 cm$^3$/g, which accounts for 100% of the total pore volume. FIG. 1-19 is a diagram showing the pore-size distribution of the carbon-coated nickel nanocomposite material obtained in Example 1-7. As can be seen from FIG. 1-19, two distribution peaks of mesopores are present at 3.97 nm and 6.39 nm on the BJH pore-size distribution curve of the material. In the acid leaching test, the loss on acid leaching of the material was 12.4%. The loss on acid leaching was kept substantially unchanged, where the time of acid leaching was prolonged on the basis of the above-described method.

FIG. 1-20 shows a TEM image of the carbon-coated nickel nanocomposite material obtained in Example 1-8. As can be seen from FIG. 1-20, the material has a core-shell structure with metallic nickel nanoparticles as the core and carbon having a certain graphitization degree as the shell. There are diffraction peaks corresponding to graphitic carbon (at 2θ of 25.8°) and fcc-Ni (44.6°, 51.8° and 76.4°) in the XRD pattern of the material (FIG. 1-21), indicating that the material comprises carbon having a certain graphitization degree and nickel present in a face-centered-cubic structure. The average particle size of the carbon-coated nickel nanoparticles is 8.4 nm as calculated by the Scherrer formula. In the acid leaching test, the loss on acid leaching of the material was 29.4%. The loss on acid leaching was kept substantially unchanged, where the time of acid leaching was prolonged on the basis of the above-described method.

FIG. 1-22 shows a TEM image of the carbon-coated nickel nanocomposite material obtained in Example 1-9. As can be seen from FIG. 1-22, the material has a core-shell structure with metallic nickel nanoparticles as the core and carbon having a certain graphitization degree as the shell. There are diffraction peaks corresponding to graphitic carbon (at 2θ of 25.9°) and fcc-Ni (44.4°, 51.7° and 76.3°) in the XRD pattern of the material (FIG. 1-23), indicating that the material comprises carbon having a certain graphitization degree and nickel present in a face-centered-cubic structure. The average particle size of the carbon-coated nickel nanoparticles is 7.5 nm as calculated by the Scherrer formula. In the acid leaching test, the loss on acid leaching of the material was 25.6%. The loss on acid leaching was kept substantially unchanged, where the time of acid leaching was prolonged on the basis of the above-described method.

FIG. 1-24 is a photograph of the magnetic test of the carbon-coated nickel nanocomposite material obtained in Example 1-10, which shows that a suspension of the carbon-coated nickel nanocomposite material rapidly becomes clear after being attracted by a magnet, indicating that the carbon-coated material obtained has strong magnetism. FIG. 1-25 shows a TEM image of the nanocomposite material, from which it can be seen that the material has a core-shell structure with metallic nickel nanoparticles as the core and graphitized carbon layer as the shell. The X-ray diffraction pattern of the composite material is shown in FIG. 1-26, from which it can be seen that there are diffraction peaks corresponding to graphitic carbon (at 2θ of 25.7°) and diffraction peaks corresponding to fcc-Ni (44.5°, 51.9° and 76.2°). The average particle size of the carbon-coated nickel nanoparticles is 4.2 nm as calculated by the Scherrer formula. The BET test shows that the specific surface area of the material is 176 $m^2/g$, the pore volume is 0.381 $cm^3/g$, in which the mesopore volume is 0.376 $cm^3/g$, which accounts for 98.7% of the total pore volume. FIG. 1-27 is a diagram showing the pore-size distribution of the carbon-coated nickel nanocomposite material obtained in Example 1-10. As can be seen from FIG. 1-27, two distribution peaks of mesopores are present at 3.80 nm and 10.47 nm on the BJH pore-size distribution curve of the material.

The carbon-coated nickel nanocomposite material obtained in Comparative Example 1-1 was subjected to the above-described characterization test, and the results show that there are diffraction peaks corresponding to graphitic carbon (at 2θ of 26°) and diffraction peaks corresponding to fcc-Ni (44.5°, 51.9° and 76.2°) in the XRD pattern of the material, indicating that the material comprises carbon having a certain graphitization degree and nickel present in a face-centered-cubic structure. The BET test shows that the specific surface area of the material is 159 $m^2/g$ and the pore volume is 0.208 $cm^3/g$, in which the pore volume of the pores having a pore size >2 nm is 0.05 $cm^3/g$, which accounts for 24% of the total pore volume. There is only one distribution peak of micropores at 0.68 nm on the BJH pore-size distribution curve of the material. In the acid leaching test, the loss on acid leaching of the material was 92%.

FIG. 1-28 shows an XRD pattern of the sample material obtained in Comparative Example 1-4, from which it can be seen that there are diffraction peaks corresponding to fcc-Ni (44.2°, 51.6° and 76.2°) in the diffraction pattern of the material. As determined by the element analyzer and the X-ray fluorescence spectrum analyzer (XRF), the material contains the following elements by mass: 1.34% of carbon, 0.32% of hydrogen, 0.18% of oxygen and 98.16% of nickel.

By comparing Examples 1-1 to 1-10 with Comparative Examples 1-1 to 1-3, it can be seen that the method according to the present application is simpler and more efficient, in which the precursor to be subjected to the high-temperature pyrolysis can be directly prepared by the reaction of a transition metal salt and a polybasic organic carboxylic acid in a solvent (e.g. water), the atom utilization in the precursor of the transition metal contained in the raw material can be 100%, the following defects of the prior art, i.e. the need for a high-temperature and high-pressure reaction kettle in the self-assembly reaction, the waste of a large amount of precursor of carbon source, the consumption of a large amount of organic solvent, the complexity in purification and the like, for preparing the precursor having a metallic organic framework structure can be overcome; and no high-molecular auxiliary agent is needed, so that the reaction procedure can be simplified.

Further, the method according to the present application allows the preparation of tightly-wrapped nanocomposite materials, so that the materials can be used under more severe conditions. Furthermore, the method according to the present application allows the preparation of tightly-wrapped nanocomposite materials having a structure rich in mesopores, particularly a multilevel mesoporous structure, so that they are suitable for use in more fields.

Part II

Example 2-1

10 g of nickel acetate, 10 g of citric acid and 20 g of hexamethylenetetramine were weighed, added into 30 mL of deionized water, stirred at 70° C. to obtain a homogeneous solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 100 mL/min, heated to 650° C. at a heating rate of 5° C./min, kept at the temperature for 2 h, and then the heating was stopped. The resultant was cooled to room temperature in a nitrogen atmosphere to obtain a carbon-coated nickel nanocomposite material.

Example 2-2

10 g of nickel acetate, 20 g of citric acid and 20 g of hexamethylenetetramine were weighed, added into 100 mL of deionized water, stirred at 80° C. to obtain a homogeneous solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 150 mL/min, heated to 600° C. at a heating rate of 5° C./min, kept at the temperature for 2 h, and then the heating was stopped. The resultant was cooled to room temperature in a nitrogen atmosphere to obtain a carbon-coated nickel nanocomposite material.

Example 2-3

10 g of cobalt acetate, 10 g of citric acid and 20 g of hexamethylenetetramine were weighed, added into a beaker containing 150 mL of deionized water, stirred at 60° C. to obtain a homogeneous solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 100 mL/min, heated to 700° C. at a heating rate of 5° C./min, kept at the temperature for 1 h, and then the heating was stopped. The resultant was cooled to room temperature in a nitrogen atmosphere to obtain a carbon-coated cobalt nanocomposite material.

Example 2-4

10 g of nickel acetate, 10 g of cobalt acetate, 20 g of citric acid and 10 g of hexamethylenetetramine were weighed, added into a beaker containing 150 mL of deionized water, stirred at 60° C. to form a homogeneous solution, and the solution was continuously heated and evaporated to dryness to obtain a solid.

The precursor was placed in a porcelain boat, then the porcelain boat was placed in the constant-temperature zone of a tube furnace, nitrogen was introduced at a flow rate of 100 mL/min, heated to 600° C. at a heating rate of 4° C./min, kept at the temperature for 2 h, and then the heating was stopped. The resultant was cooled to room temperature in a nitrogen atmosphere to obtain a carbon-coated nickel-cobalt nanocomposite material.

Example 2-5

10 g of nickel acetate, 10 g of citric acid and 20 g of dicyanodiamide were weighed, added into 150 mL of deionized water, stirred at 60° C. to obtain a homogeneous solution, the solution was continuously heated and evaporated to dryness, and the solid was ground to obtain a precursor.

The precursor was placed in a porcelain boat, then the porcelain boat was placed in the constant-temperature zone of a tube furnace, nitrogen was introduced at a flow rate of 100 mL/min, heated to 700° C. at a heating rate of 5° C./min, kept at the temperature for 1 h, and then the heating was stopped. The resultant was cooled to room temperature in a nitrogen atmosphere to obtain a carbon-coated nickel nanocomposite material.

Example 2-6

10 g of nickel acetate, 10 g of citric acid, 20 g of urea and 3 g of maleic acid were weighed, added into 50 mL of deionized water, stirred at 60° C. to obtain a homogeneous solution, the solution was continuously heated and evaporated to dryness, and the solid was ground to obtain a precursor.

The precursor was placed in a porcelain boat, then the porcelain boat was placed in the constant-temperature zone of a tube furnace, nitrogen was introduced at a flow rate of 100 mL/min, heated to 550° C. at a heating rate of 3° C./min, kept at the temperature for 3 h, and then the heating was stopped. The resultant was cooled to room temperature in a nitrogen atmosphere to obtain a carbon-coated nickel nanocomposite material.

Example 2-7

10 g of nickel acetate, 20 g of terephthalic acid and 20 g of hexamethylenetetramine were weighed, added into 100 mL of deionized water, stirred at 80° C. to obtain a homogeneous solution, the solution was continuously heated and evaporated to dryness, and the solid was ground to obtain a precursor.

The precursor was placed in a porcelain boat, then the porcelain boat was placed in the constant-temperature zone of a tube furnace, nitrogen was introduced at a flow rate of 80 mL/min, heated to 800° C. at a heating rate of 8° C./min, kept at the temperature for 2 h, and then the heating was stopped. The resultant was cooled to room temperature in a nitrogen atmosphere to obtain a carbon-coated nickel nanocomposite material.

Example 2-8

10 g of nickel acetate, 7 g of citric acid, 10 g of melamine and 5 g of pentaerythritol were weighed, added into 150 mL of deionized water, stirred at 60° C. to obtain a homogeneous solution, and the solution was continuously heated and evaporated to dryness to obtain a precursor.

The precursor was placed in a porcelain boat, then the porcelain boat was placed in the constant-temperature zone of a tube furnace, nitrogen was introduced at a flow rate of 100 mL/min, heated to 600° C. at a heating rate of 6° C./min, kept at the temperature for 1 h, and then the heating was stopped. The resultant was cooled to room temperature in a nitrogen atmosphere to obtain a carbon-coated nickel nanocomposite material.

Example 2-9

20 g of nickel acetate and 10 g of ethylenediamine tetraacetic acid were weighed, added into 150 mL of deionized water, stirred at 60° C. to form a homogeneous solution, the solution was continuously heated and evaporated to dryness, and the solid was ground to obtain a precursor.

The precursor was placed in a porcelain boat, then the porcelain boat was placed in the constant-temperature zone of a tube furnace, nitrogen was introduced at a flow rate of 100 mL/min, heated to 600° C. at a heating rate of 4° C./min, kept at the temperature for 2 h, and then the heating was stopped. The resultant was cooled to room temperature in a nitrogen atmosphere to obtain a carbon-coated nickel nanocomposite material.

Example 2-10

The process of Example 2-1 was repeated, and an acid treatment was performed after the process of Example 2-1, i.e., 2 g of the material obtained in Example 2-1 was added to 100 mL of 10 wt % hydrochloric acid, treated at the reflux temperature for 12 h, washed with deionized water until neutral, and dried at 120° C. to obtain a tightly-wrapped carbon-coated nickel nanocomposite material.

Comparative Example 2-1

Preparation of Ni-MOF material: 3.09 g of nickel nitrate, 2.8 g of terephthalic acid and 0.95 g of triethylene diamine were weighed, added into 120 mL of dimethylformamide, reacted at 120° C. for 8 h, sealed and left to stand at 120° C. for 40 h; the resultant was filtered, washed with dimethyl-formamide and methanol, and dried in vacuum to obtain the Ni-MOF material.

Synthesis of nitrogen-doped carbon-coated nickel (Ni@C—N) nano material: the Ni-MOF obtained was placed in a porcelain boat, then the porcelain boat was placed in the constant-temperature zone of a tube furnace, nitrogen was introduced at a flow rate of 100 mL/min, heated to 200° C. at a heating rate of 4° C./min, kept at the temperature for 2 h, then heated to 500° C., kept at the temperature for 8 h, and the heating was stopped. The resultant was cooled to room temperature in a nitrogen atmosphere to obtain the Ni@C—N nano material.

Comparative Example 2-2

The process of Example 2-1 was repeated, except that 10 g of nickel nitrate was used in place of the 10 g of nickel acetate.

Comparative Example 2-3

The process of Example 2-9 was repeated, except that 10 g of disodium ethylenediaminetetraacetate was used in place of the 10 g of ethylenediaminetetraacetic acid.

Characterization of the Resulting Material

The contents by mass of the elements contained in the materials obtained in Examples 2-1 to Examples 2-11 are shown in Table 2-1.

TABLE 2-1

Contents of elements in the materials obtained in Examples

| Example No. | Carbon (wt %) | Hydrogen (wt %) | Nitrogen (wt %) | Oxygen (wt %) | Nickel (wt %) | Cobalt (wt %) |
|---|---|---|---|---|---|---|
| Ex. 2-1 | 43.30 | 1.08 | 3.88 | 3.99 | 47.75 | — |
| Ex. 2-2 | 46.86 | 1.20 | 4.26 | 5.22 | 42.46 | — |
| Ex. 2-3 | 44.75 | 0.98 | 3.25 | 3.68 | — | 47.34 |
| Ex. 2-4 | 32.35 | 0.52 | 1.68 | 1.21 | 30.72 | 33.52 |
| Ex. 2-5 | 43.84 | 1.24 | 5.12 | 4.56 | 45.24 | — |
| Ex. 2-6 | 54.49 | 1.56 | 2.46 | 1.24 | 40.25 | — |
| Ex. 2-7 | 53.91 | 1.14 | 3.75 | 2.74 | 38.46 | — |
| Ex. 2-8 | 37.86 | 0.79 | 3.58 | 0.54 | 57.23 | — |
| Ex. 2-9 | 31.89 | 1.26 | 2.34 | 3.14 | 61.37 | — |
| Ex. 2-10 | 47.55 | 1.33 | 4.27 | 4.84 | 42.01 | — |

The materials obtained in Examples 2-1 to 2-11 and Comparative Examples 2-1 to 2-3 were subjected to acid leaching, and the loss on acid leaching is shown in Table 2-2.

TABLE 2-2

Loss on acid leaching of materials obtained in Examples and Comparative Examples

| Example No. | Loss on acid leaching (%) |
|---|---|
| Ex. 2-1 | 14 |
| Ex. 2-2 | 9.3 |
| Ex. 2-3 | 31.2 |
| Ex. 2-4 | 38.4 |
| Ex. 2-5 | 31.2 |
| Ex. 2-6 | 25.4 |
| Ex. 2-7 | 16.7 |
| Ex. 2-8 | 39.8 |
| Ex. 2-9 | 21.7 |
| Ex. 2-10 | 0.34 |
| Comp. Ex. 2-1 | 64.2 |
| Comp. Ex. 2-2 | 78.2 |
| Comp. Ex. 2-3 | 100 |

It can be seen from the data shown in Tables 2-1 and 2-2 that, in the carbon-coated transition metal nanocomposite material obtained in Examples 2-1 to 2-11 of the present application, the transition metal is wrapped by carbon with a better effect, i.e., most of the metal is tightly wrapped by the carbon layer.

FIG. 2-1 is a photograph of the magnetic test of the carbon-coated nickel nanocomposite material doped with oxygen and nitrogen obtained in Example 2-1, which shows that a suspension of the carbon-coated nickel nanocomposite material doped with oxygen and nitrogen rapidly becomes clear after being attracted by a magnet, indicating that the composite material has strong magnetism. FIG. 2-2 shows a TEM image of the carbon-coated nickel nanocomposite material doped with oxygen and nitrogen obtained in Example 2-1. As can be seen from FIG. 2-2, the composite material comprises carbon-coated metallic nickel particles, which are coated with a carbon layer having a certain graphitization degree on the outer surface of the nickel nanoparticles to form a complete core-shell structure. FIG. 2-3 shows an XRD pattern of the carbon-coated nickel nanocomposite material doped with oxygen and nitrogen obtained in Example 2-1. As can be seen from FIG. 2-3, there are diffraction peaks corresponding to graphite carbon (at 2θ of 25.96°) and diffraction peaks corresponding to nickel present in a face-centered-cubic structure (fcc-Ni) (at 2θ of 44.38°, 51.83° and 76.42°) in the diffraction pattern of the material, indicating that the material comprises carbon having a certain graphitization degree and nickel present in a face-centered-cubic structure. The average particle size of the carbon-coated nickel nanoparticles is 6.3 nm as calculated by the Scherrer formula. The BET test shows that the specific surface area of the material is 114 m$^2$/g, the pore volume is 0.181 cm$^3$/g, in which the mesopore volume is 0.173 cm$^3$/g, which accounts for 95.6% of the total pore volume. FIG. 2-4A and 2-4B show an N$_2$ adsorption-desorption isotherm and a BJH pore-size distribution diagram of the material, respectively, from which it can be seen that the composite material has two distribution peaks of mesopores at 3.75 nm and 10.03 nm. In the acid leaching test, the loss on acid leaching of the material was 14%.

FIG. 2-5 shows a TEM image of the carbon-coated nickel nanocomposite material obtained in Example 2-2, which shows that the material has a core-shell structure with metallic nickel nanoparticles as the core and carbon having a certain graphitization degree as the shell. There are diffraction peaks corresponding to graphite carbon (at 2θ of 25.8°), fcc-Ni (at 2θ of 44.4°, 51.9° and 76.5°), and nickel present in a hexagonal-close-packed structure (hcp-Ni) (at 2θ of 41.9°, 44.4°, 47.5° and 62.41°) in the XRD pattern of the material (FIG. 2-6), indicating that the material comprises carbon having a certain graphitization degree and nickel present in a face-centered-cubic structure and in a hexagonal-close-packed structure. The average particle size of the carbon-coated nickel nanoparticles is 31.4 nm as calculated by the Scherrer formula. The BET test shows that the specific surface area of the material is 126 m$^2$/g, the pore volume is 0.213 cm$^3$/g, in which the mesopore volume is 0.207 cm$^3$/g, which accounts for 97.1% of the total pore volume. By determining the N2 adsorption-desorption isotherm and the BJH pore-size distribution diagram (FIG. 2-7) of the material, it can be observed that the composite material has two distribution peaks of mesopores at 3.83 nm and 11.16 nm. In the acid leaching test, the loss on acid leaching of the material was 9.3%.

FIG. 2-8 shows a TEM image of the carbon-coated cobalt nanocomposite material obtained in Example 2-3, which shows that the material has a core-shell structure with metallic cobalt nanoparticles as the core and carbon having a certain graphitization degree as the shell. There is a diffraction peak corresponding to cobalt (at 2θ of 44.42°) in the XRD pattern of the material (FIG. 2-9), indicating the presence of elemental cobalt in the material. The average particle size of the carbon-coated cobalt nanoparticles is 17.5 nm as calculated by the Scherrer formula. The BET test shows that the specific surface area of the material is 140 m$^2$/g, the pore volume is 0.158 cm$^3$/g, in which the mesopore volume is 0.158 cm$^3$/g, which accounts for 100% of the total pore volume. By determining the N2 adsorption-desorption isotherm and the BJH pore-size distribution diagram (FIG. 2-10) of the material, it can be observed that the composite material has two distribution peaks of mesopores at 3.77 nm and 13.32 nm. In the acid leaching test, the loss on acid leaching of the material was 31.2%.

FIG. 2-11 shows an XRD pattern of the precursor obtained in Example 2-4, which shows that the precursor obtained is an amorphous material. FIG. 2-12 shows a TEM image of the carbon-coated nickel-cobalt nanocomposite material obtained in Example 2-4, which shows that the material has a core-shell structure with metallic nickel or cobalt nanoparticles as the core and carbon having a certain graphitization degree as the shell. There are diffraction peaks corresponding to fcc-Ni and cobalt (at 2θ of 44.5°, 51.7°, and 76.2°) in the XRD pattern of the material (FIG. 2-13), indicating that the material comprises carbon having a certain graphitization degree, and nickel and/or cobalt present in a face-centered-cubic structure. The average particle size of the carbon-coated nanoparticles is 24.4 nm as calculated by the Scherrer formula. The specific surface area of the material is 182 m$^2$/g, the pore volume is 0.256 cm$^3$/g, in which the mesopore volume is 0.256 cm$^3$/g, which accounts for 100% of the total pore volume. By determining the N2 adsorption-desorption isotherm and the BJH pore-size distribution diagram (FIG. 2-14) of the material, it can be observed that the composite material has two distribution peaks of mesopores at 3.7 nm and 6.34 nm. In the acid leaching test, the loss on acid leaching of the material was 38.4%.

FIG. 2-15 shows a TEM image of the carbon-coated nickel nanocomposite material obtained in Example 2-5, which shows that the material has a core-shell structure with metallic nickel nanoparticles as the core and carbon having a certain graphitization degree as the shell. In the XRD pattern of the material (FIG. 2-16), there are diffraction peaks corresponding to graphite carbon (at 2θ of 25.8°), fcc-Ni (44.4°, 51.9° and 76.2°), and hcp-Ni (at 2θ of 42.1°, 44.4°, 47.42° and 62.63°), indicating that the material comprises carbon having a certain graphitization degree and nickel present in a face-centered-cubic structure and in a hexagonal-close-packed structure. The average particle size of the carbon-coated nanoparticles is 7.6 nm as calculated by the Scherrer formula. In the acid leaching test, the loss on acid leaching of the material was 31.2%.

FIG. 2-17 shows a TEM image of the carbon-coated nickel nanocomposite material obtained in Example 2-6, which shows that the material has a core-shell structure with metallic nickel nanoparticles as the core and carbon having a certain graphitization degree as the shell. There are diffraction peaks corresponding to fcc-Ni (44.45°, 51.8°, and 76.3°) and diffraction peaks corresponding to hcp-Ni (at 2θ of 41.6°, 44.4°, 47.6°, and 62.6°) in the XRD pattern of the material (FIG. 2-18), indicating that the material comprises carbon having a certain graphitization degree and nickel present in a face-centered-cubic structure and in a hexagonal-close-packed structure. The average particle size of the carbon-coated nanoparticles is 28.4 nm as calculated by the Scherrer formula. In the acid leaching test, the loss on acid leaching of the material was 25.4%.

FIG. 2-19 shows a TEM image of the carbon-coated nickel nanocomposite material obtained in Example 2-7, which shows that the material has a core-shell structure with metallic nickel nanoparticles as the core and carbon having a certain graphitization degree as the shell. In the XRD pattern of the material (FIG. 2-20), there are diffraction peaks corresponding to graphitic carbon (at 2θ of 26.04°) and diffraction peaks corresponding to fcc-Ni (44.6°, 51.8° and) 76.3°, indicating that the material comprises carbon having a certain graphitization degree and nickel present in a face-centered-cubic structure. The average particle size of the carbon-coated nanoparticles is 4.7 nm as calculated by the Scherrer formula. In the acid leaching test, the loss on acid leaching of the material was 16.7%.

FIG. 2-21 shows a TEM image of the carbon-coated nickel nanocomposite material obtained in Example 2-8, which shows that the material has a core-shell structure with metallic nickel nanoparticles as the core and carbon having a certain graphitization degree as the shell. There are diffraction peaks corresponding to fcc-Ni (44.4°, 51.9°, and 76.3°) and hcp-Ni (at 2θ of 41.7°, 44.4°, 47.5°, and 62.6°) in the XRD pattern of the material (FIG. 2-22), indicating that the material comprises carbon having a certain graphitization degree and nickel present in a face-centered-cubic structure and in a hexagonal-close-packed structure. The average particle size of the carbon-coated nanoparticles is 32.4 nm as calculated by the Scherrer formula. The BET test shows that the specific surface area of the material is 228 m$^2$/g, the pore volume is 0.293 cm$^3$/g, in which the mesopore volume is 0.289 cm$^3$/g, which accounts for 98.6% of the total pore volume. By determining the N2 adsorption-desorption isotherm and the BJH pore-size distribution diagram (FIG. 2-23) of the material, it can be observed that the composite material has a distribution peak of mesopores at 3.75 nm. In the acid leaching test, the loss on acid leaching of the material was 39.8%.

FIG. 2-24 shows a TEM image of the carbon-coated nickel nanocomposite material obtained in Example 2-9, which shows that the material has a core-shell structure with metallic nickel nanoparticles as the core and carbon having a certain graphitization degree as the shell. There are diffraction peaks corresponding to graphitic carbon (at 2θ of 25.9°) and fcc-Ni (44.5°, 51.7° and 76.3°) in the XRD pattern of the material (FIG. 2-25), indicating that the material comprises carbon having a certain graphitization degree and nickel present in a face-centered-cubic structure.

The average particle size of the carbon-coated nanoparticles is 7.6 nm as calculated by the Scherrer formula. The BET test shows that the specific surface area of the material is 232 m$^2$/g, the pore volume is 0.313 cm$^3$/g, in which the mesopore volume is 0.313 cm$^3$/g, which accounts for 100% of the total pore volume. By determining the N2 adsorption-desorption isotherm and the BJH pore-size distribution diagram (FIG. 2-26) of the material, it can be observed that the composite material has two distribution peaks of mesopores at 4.02 nm and 6.30 nm. In the acid leaching test, the loss on acid leaching of the material was 21.7%.

FIG. 2-27 is a photograph of the magnetic test of the carbon-coated nickel nanocomposite material obtained in Example 2-10, which shows that a suspension of the carbon-coated nickel nanocomposite material rapidly becomes clear after being attracted by a magnet, indicating that the material has strong magnetism. FIG. 2-28 shows a TEM image of the material, from which it can be seen that the material is a nanocomposite material having a carbon-coated metallic core-shell structure, in which a carbon layer having a certain graphitization degree is coated on the outer surface of the nickel nanoparticle to form a complete core-shell structure. The X-ray diffraction pattern of the carbon-coated nickel nanocomposite material is shown in FIG. 2-29, from which it can be seen that there are diffraction peaks corresponding to graphitic carbon (at 2θ of 25.97°) and diffraction peaks corresponding to fcc-Ni (at 2θ of 44.47°, 51.34° and 76.26°). The average particle size of the carbon-coated nickel nanoparticles is 8.1 nm as calculated by the Scherrer formula. The BET test shows that the specific surface area of the material is 200 m$^2$/g, the pore volume is 0.204 cm$^3$/g, in which the mesopore volume is 0.0201 cm$^3$/g, which accounts for 98.6% of the total pore volume. FIG. 2-30 shows the BJH pore-size distribution diagram of the material, from which it can be seen that the composite material has two distribution peaks of mesopores at 3.79 nm and 10.01 nm.

The carbon-coated nickel nanocomposite material obtained in the Comparative Example 2-1 was subjected to the above-described characterization test, of which the results show that the carbon-coated nickel nanocomposite material has a core-shell structure with metallic nickel nanoparticles as the core and carbon as the shell, with the particle size being 28.2 nm. There are diffraction peaks corresponding to fcc-Ni (44.45°, 51.32° and 76.16°) in the XRD pattern of the material, indicating that nickel is present in a face-centered-cubic structure in the material. In the acid leaching test, the loss on acid leaching of the material was 64.2%.

By comparing Examples 2-1 to 2-11 with Comparative Examples 2-1 to 2-3, it can be seen that the method according to the present application is simpler and more efficient, the precursor to be subjected to the high-temperature pyrolysis is directly prepared by the reaction of a transition metal salt, a polybasic organic carboxylic acid and a nitrogen-containing compound in a solvent, the atom utilization in the precursor of the transition metal contained in the raw material can be 100%, the following defects of the prior art, i.e. the need for a high-temperature and high-pressure reaction kettle in the self-assembly reaction, the waste of a large amount of precursor of carbon source, the consumption of a large amount of organic solvent, the complexity in purification and the like, for preparing the precursor having a metallic organic framework structure can be overcome; and no high-molecular auxiliary agent is needed, so that the reaction procedure can be simplified.

Part III

Example 3-1

2.92 g (10 mmol) of ethylenediamine tetraacetic acid, 1.53 g (5 mmol) of 1,3-propylenediaminetetraacetic acid and 1.85 g (20 mmol) of nickel hydroxide were weighed, added into 120 mL of deionized water, stirred at 80° C. to obtain a homogeneous solution, the solution was continuously heated and evaporated to dryness, and the solid was ground to obtain a precursor.

The precursor obtained was placed in a porcelain boat, then the porcelain boat was placed in the constant-temperature zone of a tube furnace, nitrogen was introduced at a flow rate of 80 mL/min, heated to 725° C. at a heating rate of 2.5° C./min, kept at the temperature for 3.5 h, and then the heating was stopped. The resultant was cooled to room temperature in a nitrogen atmosphere to obtain a carbon-coated nickel nanocomposite material, designated as P1.

The carbon-coated nickel nanocomposite material P1 obtained was added to 50 mL of 0.5 mol/L H$_2$SO$_4$ solution, stirred and refluxed at 90° C. for 6 h, and then the solution was subjected to suction filtration and washed with deionized water until neutral. Then, the powder was dried in an oven at 100° C. for 2 h to give a carbon-coated nickel nanocomposite material, designated as P2.

Example 3-2

10 mmol of NiCO$_3$ and 10 mmol of citric acid were weighed, added into 150 mL of deionized water, stirred at 70° C. to obtain a homogeneous solution, the solution was continuously heated and evaporated to dryness, and the solid was ground to obtain a precursor.

The precursor obtained was placed in a porcelain boat, then the porcelain boat was placed in the constant-temperature zone of a tube furnace, nitrogen was introduced at a flow rate of 100 mL/min, heated to 450° C. at a heating rate of 5° C./min, kept at the temperature for 1 h, and then the heating was stopped. The resultant was cooled to room temperature in a nitrogen atmosphere to obtain a carbon-coated nickel nanocomposite material P3.

The carbon-coated nickel nanocomposite material P3 obtained was added to 60 mL of 1 mol/L HCl solution, stirred and refluxed at 85° C. for 4 h, and then the solution was subjected to suction filtration and washed with deionized water until neutral. Then, the powder was dried in an oven at 100° C. for 2 h to obtain a carbon-coated nickel nanocomposite material P4.

Characterization of the Resulting Material

FIG. 3-1 shows an XRD pattern of the material P2 obtained in Example 3-1. In FIG. 3-1, only the diffraction peaks of carbon material and those of hcp-Ni and fcc-Ni are present, and the diffraction peaks of hcp-Ni at 42° and 62° almost disappear. FIG. 3-2A is a diagram showing the N2 adsorption-desorption isotherm of the material P2 obtained in Example 3-1, and FIG. 3-2B is a diagram showing the pore-size distribution of the material P2 obtained in Example 3-1. FIG. 3-2B shows that the pore-size distribution of the material P2 shows two distribution peaks at 3.7 nm and 10.0 nm. As measured, the material P2 has a specific surface area of 253 m$^2$/g and a pore volume of 0.481 cm$^3$/g, in which the mesopore volume accounts for 99.3% of the total pore volume. FIG. 3-3 shows an SEM and a TEM image of the material P2. From FIG. 3-3 (a), it can be seen that the material is an irregular block on the whole. It can be seen from FIG. 3-3 (b) that the nickel nanoparticles are uniformly dispersed in the carbon matrix. In FIG. 3-3 (c), the graphite shell and the metal core can be clearly observed, which clearly shows the core-shell structure of the nanoparticles. As determined by the elemental analyzer, the material P2 has a carbon content of 46.91 wt %, a hydrogen content of 0.42 wt %, a nitrogen content of 1.54 wt %, an oxygen content of 1.83 wt %, and a normalized nickel content of 49.30 wt %. The material P1 obtained in Example 3-1 exhibited a loss on acid leaching of 40% and the material P2 exhibited a loss on acid leaching of less than 2%, as measured by the method for the measurement of the loss on acid leaching as described in the section "Reagents, Instruments and Tests" above, and the loss on acid leaching was kept substantially unchanged, where the time of acid leaching was prolonged on the basis of said measurement method.

FIG. 3-4 is a diagram of the thermogravimetric-differential thermal analysis (TG-DTA) of the precursor material obtained in Example 3-2. As can be seen from FIG. 3-4, the precursor clearly shows two endothermic peaks during the temperature rise, wherein the endothermic peak at 366° C. corresponds to the process of high-temperature pyrolysis and carbonization of the precursor and reduction of $Ni^{2+}$ into Ni element, and the quality of the precursor is relatively stable after 400° C. FIG. 3-5 shows an XRD pattern of the material P4 obtained in Example 3-2. From FIG. 3-5, the diffraction peaks of the carbon material and those of fcc-Ni can be seen. The average particle size of the nickel nanoparticles was 8.6 nm as calculated by the Scherrer formula. FIG. 3-6 shows an XPS pattern of the material P4 obtained in Example 3-2, from which the electron binding energy peaks of C, O, Ni can be clearly seen. FIG. 3-7A is a diagram showing the N2 adsorption-desorption isotherm of the material P4 obtained in Example 3-2, and FIG. 3-7B is a diagram showing the pore-size distribution of the material P4 obtained in Example 3-2. It can be seen from FIG. 3-7A that the material P4 clearly shows a hysteresis loop within the range $P/P_0=0.4-1.0$. As can be seen from FIG. 3-7B, the pore-size distribution of the material P4 shows two distribution peaks at 3.5 nm and 6.9 nm. The specific surface area of the material P4 was 301 $m^2/g$, and the pore volume was 0.453 $cm^3/g$, in which the mesopore volume accounts for 100% of the total pore volume. As determined by the elemental analyzer, the material P4 had a carbon content of 39.80 wt %, a hydrogen content of 1.01 wt %, an oxygen content of 2.50 wt %, and a normalized nickel content of 56.69 wt %. The material P3 obtained in Example 3-2 had a loss on acid leaching of 43% and the material P4 had a loss on acid leaching of less than 1%, as measured by the method for the measurement of the loss on acid leaching as described in the section "Reagents, Instruments and Tests" above. The loss on acid leaching was kept substantially unchanged, where the time of acid leaching was prolonged on the basis of said measurement method.

Application Examples

Example 4-1

The materials obtained in the Preparation Examples and Comparative Examples of Part I and commercially available nickel protoxide (NiO) (analytically pure, batch number: 20160803, Sinopharm Chemical Reagent Co., Ltd.) were used as catalysts for the complete catalytic elimination experiment of butane in the exhaust gas generated during the production of maleic anhydride by the oxidation of n-butane in industry, respectively. The evaluation of the butane elimination rate of corresponding catalysts was carried out, and when evaluated under the same conditions, the higher the butane elimination rate, the higher the activity of the catalyst. Particularly, the evaluation method was carried out as follows:

the collected butane-containing exhaust gas from the maleic anhydride production process was sent into a fixed bed reactor loaded with a catalyst to contact with the catalyst for catalytic oxidation reaction, the reaction product obtained was subjected to gas chromatographic analysis, and the butane elimination rate was calculated:

Butane Elimination Rate=100%−Butane Volume in the Reaction Product/Butane Volume in the Exhaust Gas from the Maleic Anhydride Production Process×100%.

The exhaust gas from the maleic anhydride production process comprised about 1% by volume of butane, and the balance was air and a very small amount of carbon monoxide and carbon dioxide, the reaction space velocity was 5000 mL of exhaust gas/(h·g of catalyst), the evaluation time was 5 h, and the reaction temperature and butane elimination rate are shown in Table 4-1.

TABLE 4-1

Reaction temperature and butane elimination rate of Example 4-1

| Sources of materials | Reaction temperature (° C.) | Butane eliminating rate (%) |
|---|---|---|
| Example 1-1 | 200 | 5.4 |
| | 300 | 57.2 |
| | 350 | 97.5 |
| | 400 | 100 |
| Example 1-2 | 300 | 50.2 |
| | 350 | 99.5 |
| | 400 | 100 |
| Example 1-3 | 300 | 67.4 |
| | 350 | 100 |
| Example 1-6 | 300 | 41.2 |
| | 350 | 100 |
| Example 1-8 | 300 | 7.2 |
| | 350 | 97.3 |
| | 400 | 100 |
| Comparative Example 1-4 | 300 | 7.2 |
| | 350 | 23.6 |
| | 400 | 70.6 |
| | 450 | 100 |
| Example 1-10 | 300 | 7.2 |
| | 350 | 28.6 |
| | 400 | 67.9 |
| | 450 | 100 |
| Commercial nickel protoxide | 300 | 6.7 |
| | 350 | 8.2 |
| | 400 | 22.1 |
| | 450 | 25.1 |
| | 500 | 40.4 |

As can be seen from Table 4-1, the nanocomposite materials obtained in Examples 1-1 to 1-3, 1-6 and 1-8 of the present application can catalyze the complete oxidation of butane to $CO_2$ at a temperature below 400° C., wherein an elimination rate of 100% of butane in the exhaust gas from the maleic anhydride production process comprising 1 vol % of butane can be achieved by using the carbon-coated cobalt nanocomposite material obtained in Example 1-3 and the carbon-coated nickel-cobalt nanocomposite material obtained in Example 1-6 at 350° C. It can be seen that the nanocomposite material according to the present application, particularly the nanocomposite material not subjected to the acid treatment, shows good low-temperature activity when used as a catalyst for catalytic oxidation, which is of great significance for the complete removal of volatile organic compounds in industrial exhaust gases by catalytic combustion. The graphitized carbon layer plays a role in isolating and stabilizing the metallic active center under the reaction conditions, and can effectively prevent the aggregation and inactivation of the active center. When the nanocomposite material according to the present application is used in the treatment of the exhaust gas from the maleic anhydride production process, the reaction temperature can be greatly reduced, and the energy consumption can be reduced.

Example 4-2

The nanocomposite materials obtained in the Preparation Examples and Comparative Examples 1-4 of Part II and commercially available nickel protoxide (NiO) (analytically pure, batch number: 20160803, Sinopharm Chemical Reagent Co., Ltd.) were used as catalysts for the complete catalytic elimination experiment of butane in the exhaust gas generated during the production of maleic anhydride by the oxidation of n-butane in industry, respectively. The evaluation of the butane elimination rate of corresponding catalysts was carried out as follows:

the collected butane-containing exhaust gas from the maleic anhydride production process was sent into a fixed bed reactor loaded with a catalyst to contact with the catalyst for catalytic oxidation reaction, the reaction product obtained was subjected to gas chromatographic analysis, and the butane elimination rate was calculated:

Butane elimination rate=100%−butane volume in the reaction product/butane volume in the exhaust gas from the maleic anhydride production process×100%.

The exhaust gas from the maleic anhydride production process comprised about 1% by volume of butane, and the balance was air and a very small amount of carbon monoxide and carbon dioxide, the reaction space velocity was 5000 mL of exhaust gas/(h·g of catalyst), the evaluation time was 5 h, and the reaction temperature and butane elimination rate are shown in Table 4-2.

TABLE 4-2

Reaction temperature and butane elimination data of Example 4-2

| Sources of materials | Reaction temperature (° C.) | Butane eliminating rate (%) |
|---|---|---|
| Example 2-1 | 200 | 21.2 |
| | 300 | 79.2 |
| | 350 | 100 |
| Example 2-2 | 300 | 84.9 |
| | 350 | 100 |
| Example 2-3 | 250 | 47.3 |
| | 300 | 100 |
| Example 2-4 | 200 | 61.3 |
| | 350 | 100 |
| Comparative Example 1-4 | 300 | 7.2 |
| | 350 | 23.6 |
| | 400 | 70.6 |
| | 450 | 100 |
| Example 2-1 (acid treatment)* | 300 | 11.6 |
| | 350 | 14.6 |
| | 400 | 53.4 |
| | 450 | 89.1 |
| | 500 | 100 |
| Commercial nickel protoxide | 300 | 6.7 |
| | 350 | 8.2 |
| | 400 | 22.1 |
| | 450 | 25.1 |
| | 500 | 40.4 |

*The material obtained after acid treatment of the material obtained in Example 2-1, the acid treatment was carried out under the following conditions: 2.0 g of the carbon nanocomposite material obtained in Preparation Example 2-1 was weighed, washed with 80 mL of 1M sulfuric acid at 90° C. for 8 h, then washed with deionized water until neutral, and dried at 120° C.

As can be seen from Table 4-2, an elimination rate of 100% of butane in the exhaust gas from the maleic anhydride production process comprising 1 vol % butane can be achieved by using the nanocomposite materials obtained in Examples 2-1 to 2-4 of the present application at 350° C., which temperature is significantly lower than that needed for the composite material of Comparative Example 1-4 and commercially available nickel protoxide. It can be seen that the nanocomposite material according to the present application, particularly the nanocomposite material not subjected to the acid treatment, shows good low-temperature activity when used as a catalyst for catalytic oxidation, which is of great significance for the complete removal of volatile organic compounds in industrial exhaust gases by catalytic combustion. The graphitized carbon layer plays a role in isolating and stabilizing the metallic active center under the reaction conditions, and can effectively prevent the aggregation and inactivation of the active center. When the nanocomposite material according to the present application is used in the treatment of the exhaust gas from the maleic anhydride production process, the reaction temperature can be greatly reduced, the stability of the catalyst can be maintained, and the energy consumption can be reduced.

Example 4-3

The nanocomposite material obtained in Example 1-1 was used as a catalyst in the production of aniline by the hydrogenation of nitrobenzene, and the experimental procedure was as follows:

0.1 g of the nanocomposite material, 2.7 mmol of nitrobenzene and 30 mL of absolute ethanol were added into a reaction kettle, the reaction kettle was purged with $H_2$ for 3 times, the pressure in the reaction kettle was raised to 1 MPa by introducing $H_2$, the resulting mixture was stirred, heated to 60° C., and reacted for 2 h. Then, the heating was stopped, the resultant was cooled to room temperature, the reaction kettle was depressurized and opened, and the product was withdrawn for gas chromatographic analysis. The conversion of nitrobenzene was 100% and the selectivity to aniline was 99.9%.

Example 4-4

The nanocomposite material obtained in Example 1-10 was used as a catalyst in the reaction for producing aniline by the hydrogenation of nitrobenzene, and the experimental procedure was as follows:

0.1 g of the nanocomposite material, 2.7 mmol of nitrobenzene and 30 mL of absolute ethanol were added into a reaction kettle, the reaction kettle was purged with $H_2$ for 3 times, the pressure in the reaction kettle was raised to 1

MPa by introducing $H_2$, the resulting mixture was stirred, heated to 60° C., and reacted for 2 h. Then, the heating was stopped, the resultant was cooled to room temperature, the reaction kettle was depressurized and opened, and the product was withdrawn for gas chromatographic analysis. The conversion of nitrobenzene was 100% and the selectivity to aniline was 99.9%.

Example 4-5

The nanocomposite material obtained in Example 1-1 was used as a catalyst in the reaction for producing p-chloroaniline by the hydrogenation of p-chloronitrobenzene, and the experimental procedure was as follows:

0.1 g of the nanocomposite material, 3 mmol of p-chloronitrobenzene and 30 mL of absolute ethanol were added into a reaction kettle, the reaction kettle was purged with $H_2$ for 3 times, the pressure in the reaction kettle was raised to 0.5 MPa by introducing $H_2$, the resulting mixture was stirred, heated to 120° C., and reacted for 0.5 h. Then, the heating was stopped, the resultant was cooled to room temperature, the reaction kettle was depressurized and opened, and the product was withdrawn for gas chromatographic analysis. The conversion of p-chloronitrobenzene was 100%, and the selectivity to p-chloroaniline was 99.5%.

Example 4-6

The nanocomposite material obtained in Example 1-10 was used as a catalyst in the reaction for producing p-chloroaniline by the hydrogenation of p-chloronitrobenzene, and the experimental procedure was as follows:

0.1 g of the nanocomposite material, 2 mmol of p-chloronitrobenzene and 30 mL of absolute ethanol were added into a reaction kettle, the reaction kettle was purged with $H_2$ for 3 times, the pressure in the reaction kettle was raised to 1 MPa by introducing $H_2$, the resulting mixture was stirred, heated to 60° C., and reacted for 2 h. Then, the heating was stopped, the resultant was cooled to room temperature, the reaction kettle was depressurized and opened, and the product was withdrawn for gas chromatographic analysis. The conversion of p-chloronitrobenzene was 100%, and the selectivity to p-chloroaniline was 99.9%.

Example 4-7

The nanocomposite material obtained in Example 2-1 was used as a catalyst in the reaction for producing aniline by the hydrogenation of nitrobenzene, and the experimental procedure was as follows:

0.1 g of the nanocomposite material, 2.7 mmol of nitrobenzene and 30 mL of absolute ethanol were added into a reaction kettle, the reaction kettle was purged with $H_2$ for 3 times, the pressure in the reaction kettle was raised to 1 MPa by introducing $H_2$, the resulting mixture was stirred, heated to 60° C., and reacted for 2 h. Then, the heating was stopped, the resultant was cooled to room temperature, the reaction kettle was depressurized and opened, and the product was withdrawn for gas chromatographic analysis. The conversion of nitrobenzene was 100% and the selectivity to aniline was 99.9%.

Example 4-8

The nanocomposite material obtained in Example 2-1 was used as a catalyst in the reaction for producing p-chloroaniline by the hydrogenation of p-chloronitrobenzene, and the experimental procedure was as follows:

0.1 g of the nanocomposite material, 4.2 mmol of p-chloronitrobenzene and 50 mL of absolute ethanol were added into a reaction kettle, the reaction kettle was purged with $H_2$ for 3 times, the pressure in the reaction kettle was raised to 0.5 MPa by introducing $H_2$, the resulting mixture was stirred, heated to 120° C., and reacted for 0.5 h. Then, the heating was stopped, the resultant was cooled to room temperature, the reaction kettle was depressurized and opened, and the product was withdrawn for gas chromatographic analysis. The conversion of p-chloronitrobenzene was 100%, and the selectivity to p-chloroaniline was 99.2%.

Example 4-9

The nanocomposite material obtained in Example 1-1 was used as a catalyst in the reaction for producing cyclohexanol by the hydrogenation of phenol, and the experimental procedure was as follows:

0.1 g of the composite material, 5.5 mmol of phenol and 50 mL of water were added into a reaction kettle, the reaction kettle was purged with $H_2$ for 3 times, the pressure in the reaction kettle was raised to 3 MPa by introducing $H_2$, the resulting mixture was stirred, heated to 250° C., and reacted for 6 h. Then, the heating was stopped, the resultant was cooled to room temperature, the reaction kettle was depressurized and opened, and the product was withdrawn for gas chromatographic analysis. The conversion of phenol was 100% and the selectivity to cyclohexanol was 97.8%.

Example 4-10

The nanocomposite material obtained in Example 1-10 was used as a catalyst in the reaction for producing cyclohexanol by the hydrogenation of phenol, and the experimental procedure was as follows:

0.2 g of the composite material, 7 mmol of phenol and 50 mL of water were added into a reaction kettle, the reaction kettle was purged with $H_2$ for 3 times, the pressure in the reaction kettle was raised to 3 MPa by introducing $H_2$, the resulting mixture was stirred, heated to 150° C., and reacted for 8 h. Then, the heating was stopped, the resultant was cooled to room temperature, the reaction kettle was depressurized and opened, and the product was withdrawn for gas chromatographic analysis. The conversion of phenol was 100% and the selectivity to cyclohexanol was 99.8%.

Example 4-11

The nanocomposite material obtained in Example 1-1 was used as a catalyst in the reaction for producing isopropanol by the hydrogenation of acetone, and the experimental procedure was as follows:

0.1 g of the composite material, 34 mmol of acetone and 100 mL of cyclohexane were added into a reaction kettle, the reaction kettle was purged with $H_2$ for 3 times, the pressure in the reaction kettle was raised to 6 MPa by introducing $H_2$, the resulting mixture was stirred, heated to 100° C., and reacted for 12 h. Then, the heating was stopped, the resultant was cooled to room temperature, the reaction kettle was depressurized and opened, and the product was withdrawn for gas chromatographic analysis. The conversion of acetone was 100% and the selectivity to isopropanol was 97.3%.

Example 4-12

The nanocomposite material obtained in Example 1-10 was used as a catalyst in the reaction for producing isopropanol by the hydrogenation of acetone, and the experimental procedure was as follows:

0.2 g of the composite material, 11.6 mmol of acetone and 50 mL of cyclohexane were added into a reaction kettle, the reaction kettle was purged with $H_2$ for 3 times, the pressure in the reaction kettle was raised to 3 MPa by introducing $H_2$, the resulting mixture was stirred, heated to 150° C., and reacted for 8 h. Then, the heating was stopped, the resultant was cooled to room temperature, the reaction kettle was depressurized and opened, and the product was withdrawn for gas chromatographic analysis. The conversion of acetone was 96.4% and the selectivity to isopropanol was 99.9%.

Example 4-13

The nanocomposite material obtained in Example 1-1 was used as a catalyst in the reaction for producing p-aminophenol by the hydrogenation of p-nitrophenol, and the experimental procedure was as follows:

0.1 g of the composite material, 3.5 mmol of p-nitrophenol and 50 mL of ethanol were added into a reaction kettle, the reaction kettle was purged with $H_2$ for 3 times, the pressure in the reaction kettle was raised to 0.5 MPa by introducing $H_2$, the resulting mixture was stirred, heated to 120° C., and reacted for 1 h. Then, the heating was stopped, the resultant was cooled to room temperature, the reaction kettle was depressurized and opened, and the product was withdrawn for gas chromatographic analysis. The conversion of p-nitrophenol was 100% and the selectivity to p-aminophenol was 99.1%.

Example 4-14

The nanocomposite material obtained in Example 1-10 was used as a catalyst in the reaction for producing p-aminophenol by the hydrogenation of p-nitrophenol, and the experimental procedure was as follows:

0.2 g of the composite material, 4.8 mmol of p-nitrophenol and 50 mL of ethanol were added into a reaction kettle, the reaction kettle was purged with $H_2$ for 3 times, the pressure in the reaction kettle was raised to 1 MPa by introducing $H_2$, the resulting mixture was stirred, heated to 60° C., and reacted for 2 h. Then, the heating was stopped, the resultant was cooled to room temperature, the reaction kettle was depressurized and opened, and the product was withdrawn for gas chromatographic analysis. The conversion of p-nitrophenol was 100% and the selectivity to p-aminophenol was 99.8%.

Example 4-15

The nanocomposite material obtained in Example 1-1 was used as a catalyst in the reaction for producing p-anisidine by the hydrogenation of p-nitroanisole, and the experimental procedure was as follows:

0.1 g of the composite material, 3.2 mmol of p-nitroanisole and 50 mL of ethanol were added into a reaction kettle, the reaction kettle was purged with $H_2$ for 3 times, the pressure in the reaction kettle was raised to 0.5 MPa by introducing $H_2$, the resulting mixture was stirred, heated to 120° C., and reacted for 0.5 h. Then, the heating was stopped, the resultant was cooled to room temperature, the reaction kettle was depressurized and opened, and the product was withdrawn for gas chromatographic analysis. The conversion of p-nitroanisole was 100%, and the selectivity to p-anisidine was 99.2%.

Example 4-16

The nanocomposite material obtained in Example 1-10 was used as a catalyst in the reaction for producing p-anisidine by the hydrogenation of p-nitroanisole, and the experimental procedure was as follows:

0.2 g of the composite material, 4.5 mmol of p-nitroanisole and 50 mL of ethanol were added into a reaction kettle, the reaction kettle was purged with $H_2$ for 3 times, the pressure in the reaction kettle was raised to 1 MPa by introducing $H_2$, the resulting mixture was stirred, heated to 80° C., and reacted for 2 h. Then, the heating was stopped, the resultant was cooled to room temperature, the reaction kettle was depressurized and opened, and the product was withdrawn for gas chromatographic analysis. The conversion of p-nitroanisole was 100%, and the selectivity to p-anisidine was 99.7%.

Example 4-17

The nanocomposite material obtained in Example 1-1 was used as a catalyst in the hydrogenation reaction of olefins, and the experimental procedure was as follows:

0.1 g of the composite material, 19 mmol of styrene and 100 mL of cyclohexane were added into a reaction kettle, the reaction kettle was purged with $H_2$ for 3 times, the pressure in the reaction kettle was raised to 3 MPa by introducing $H_2$, the resulting mixture was stirred, heated to 100° C., and reacted for 3 h. Then, the heating was stopped, the resultant was cooled to room temperature, the reaction kettle was depressurized and opened, and the product was withdrawn for gas chromatographic analysis. The conversion of styrene was 100% and the selectivity to ethylbenzene was 98.4%.

Example 4-18

The nanocomposite material obtained in Example 1-10 was used as a catalyst in the hydrogenation reaction of olefins, and the experimental procedure was as follows:

0.2 g of the composite material, 6.4 mmol of styrene and 50 mL of cyclohexane were added into a reaction kettle, the reaction kettle was purged with $H_2$ for 3 times, the pressure in the reaction kettle was raised to 1.5 MPa by introducing $H_2$, the resulting mixture was stirred, heated to 120° C., and reacted for 2 h. Then, the heating was stopped, the resultant was cooled to room temperature, the reaction kettle was depressurized and opened, and the product was withdrawn for gas chromatographic analysis. The conversion of styrene was 100% and the selectivity to ethylbenzene was 99.9%.

Example 4-19

The nanocomposite material obtained in Example 1-1 was used as a catalyst in the reaction for producing cyclohexane derivatives by the hydrogenation of aromatic hydrocarbons, and the experimental procedure was as follows:

0.1 g of the composite material, 20 mmol of toluene and 100 mL of cyclohexane were added into a reaction kettle, the reaction kettle was purged with $H_2$ for 3 times, the pressure in the reaction kettle was raised to 6 MPa by introducing $H_2$, the resulting mixture was stirred, heated to 200° C., and reacted for 10 h. Then, the heating was stopped, the resultant was cooled to room temperature, the reaction kettle was depressurized and opened, and the product was withdrawn for gas chromatographic analysis. The conversion of toluene was 98.3% and the selectivity to methylcyclohexane was 97.9%.

Example 4-20

The nanocomposite material obtained in Example 1-10 was used as a catalyst in the reaction for producing cyclohexane derivatives by the hydrogenation of aromatic hydrocarbons, and the experimental procedure was as follows:

0.2 g of the composite material, 7.2 mmol of toluene and 50 mL of cyclohexane were added into a reaction kettle, the reaction kettle was purged with $H_2$ for 3 times, the pressure in the reaction kettle was raised to 3 MPa by introducing $H_2$, the resulting mixture was stirred, heated to 200° C., and reacted for 8 h. Then, the heating was stopped, the resultant was cooled to room temperature, the reaction kettle was depressurized and opened, and the product was withdrawn for gas chromatographic analysis. The conversion of toluene was 95.3% and the selectivity to methylcyclohexane was 99.6%.

Example 4-21

The nanocomposite material obtained in Example 1-1 was used as a catalyst in the reaction for producing alcohols by the hydrogenation of aldehydes, and the experimental procedure was as follows:

0.1 g of the composite material, 28 mmol of butyraldehyde and 100 mL of cyclohexane were added into a reaction kettle, the reaction kettle was purged with $H_2$ for 3 times, the pressure in the reaction kettle was raised to 5 MPa by introducing $H_2$, the resulting mixture was stirred, heated to 80° C., and reacted for 8 h. Then, the heating was stopped, the resultant was cooled to room temperature, the reaction kettle was depressurized and opened, and the product was withdrawn for gas chromatographic analysis. The conversion of butyraldehyde was 100% and the selectivity to n-butanol was 99.6%.

Example 4-22

The nanocomposite material obtained in Example 1-10 was used as a catalyst in the reaction for producing alcohols by the hydrogenation of aldehydes, and the experimental procedure was as follows:

0.2 g of the composite material, 9.2 mmol of butyraldehyde and 50 mL of cyclohexane were added into a reaction kettle, the reaction kettle was purged with $H_2$ for 3 times, the pressure in the reaction kettle was raised to 3 MPa by introducing $H_2$, the resulting mixture was stirred, heated to 150° C., and reacted for 2 h. Then, the heating was stopped, the resultant was cooled to room temperature, the reaction kettle was depressurized and opened, and the product was withdrawn for gas chromatographic analysis. The conversion of butylaldehyde was 97.5% and the selectivity to n-butanol was 99.9%.

Example 4-23

The nanocomposite material obtained in Example 2-10 was used as a catalyst in the reaction for producing aniline by the hydrogenation of nitrobenzene, and the experimental procedure was as follows:

0.1 g of the nanocomposite material, 2.7 mmol of nitrobenzene and 30 mL of absolute ethanol were added into a reaction kettle, the reaction kettle was purged with $H_2$ for 3 times, the pressure in the reaction kettle was raised to 1 MPa by introducing $H_2$, the resulting mixture was stirred, heated to 60° C., and reacted for 2 h. Then, the heating was stopped, the resultant was cooled to room temperature, the reaction kettle was depressurized and opened, and the product was withdrawn for gas chromatographic analysis. The conversion of nitrobenzene was 100% and the selectivity to aniline was 99.9%.

Example 4-24

The nanocomposite material obtained in Example 2-10 was used as a catalyst in the reaction for producing p-chloroaniline by the hydrogenation of p-chloronitrobenzene, and the experimental procedure was as follows:

0.1 g of the nanocomposite material, 2.1 mmol of p-chloronitrobenzene and 30 mL of absolute ethanol were added into a reaction kettle, the reaction kettle was purged with $H_2$ for 3 times, the pressure in the reaction kettle was raised to 1 MPa by introducing $H_2$, the resulting mixture was stirred, heated to 60° C., and reacted for 2 h. Then, the heating was stopped, the resultant was cooled to room temperature, the reaction kettle was depressurized and opened, and the product was withdrawn for gas chromatographic analysis. The conversion of p-chloronitrobenzene was 100%, and the selectivity to p-chloroaniline was 99.9%.

Example 4-25

The nanocomposite material obtained in Example 2-1 was used as a catalyst in the reaction for producing alcohols by the hydrogenation of aldehydes, and the experimental procedure was as follows:

0.1 g of the composite material, 4.6 mmol of butyraldehyde and 30 mL of cyclohexane were added into a reaction kettle, the reaction kettle was purged with $H_2$ for 3 times, the pressure in the reaction kettle was raised to 3 MPa by introducing $H_2$, the resulting mixture was stirred, heated to 150° C., and reacted for 2 h. Then, the heating was stopped, the resultant was cooled to room temperature, the reaction kettle was depressurized and opened, and the product was withdrawn for gas chromatographic analysis. The conversion of butyraldehyde was 99.1% and the selectivity to n-butanol was 99.4%.

Example 4-26

The nanocomposite material obtained in Example 2-10 was used as a catalyst in the reaction for producing alcohols by the hydrogenation of aldehydes, and the experimental procedure was as follows:

0.2 g of the composite material, 9.2 mmol of butyraldehyde and 50 mL of cyclohexane were added into a reaction kettle, the reaction kettle was purged with $H_2$ for 3 times, the pressure in the reaction kettle was raised to 3 MPa by introducing $H_2$, the resulting mixture was stirred, heated to 150° C., and reacted for 2 h. Then, the heating was stopped, the resultant was cooled to room temperature, the reaction kettle was depressurized and opened, and the product was withdrawn for gas chromatographic analysis. The conversion of butyraldehyde was 100% and the selectivity to n-butanol was 99.4%.

Example 4-27

The nanocomposite material obtained in Example 2-1 was used as a catalyst in the reaction for producing cyclohexane derivatives by the hydrogenation of aromatic hydrocarbons, and the experimental procedure was as follows:

0.1 g of the composite material, 3.6 mmol of toluene and 30 mL of cyclohexane were added into a reaction kettle, the reaction kettle was purged with $H_2$ for 3 times, the pressure in the reaction kettle was raised to 3 MPa by introducing $H_2$, the resulting mixture was stirred, heated to 200° C., and reacted for 8 h. Then, the heating was stopped, the resultant was cooled to room temperature, the reaction kettle was depressurized and opened, and the product was withdrawn for gas chromatographic analysis. The conversion of toluene was 99.4% and the selectivity to methylcyclohexane was 99.6%.

Example 4-28

The nanocomposite material obtained in Example 2-10 was used as a catalyst in the reaction for producing cyclohexane derivatives by the hydrogenation of aromatic hydrocarbons, and the experimental procedure was as follows:

0.2 g of the composite material, 7.2 mmol of toluene and 50 mL of cyclohexane were added into a reaction kettle, the reaction kettle was purged with $H_2$ for 3 times, the pressure in the reaction kettle was raised to 3 MPa by introducing $H_2$, the resulting mixture was stirred, heated to 200° C., and reacted for 8 h. Then, the heating was stopped, the resultant was cooled to room temperature, the reaction kettle was depressurized and opened, and the product was withdrawn for gas chromatographic analysis. The conversion of toluene was 95.5% and the selectivity to methylcyclohexane was 99.3%.

Example 4-29

The nanocomposite material obtained in Example 2-1 was used as a catalyst in the reaction for producing cyclohexanol by the hydrogenation of phenol, and the experimental procedure was as follows:

0.1 g of the composite material, 3.5 mmol of phenol and 30 mL of water were added into a reaction kettle, the reaction kettle was purged with $H_2$ for 3 times, the pressure in the reaction kettle was raised to 3 MPa by introducing $H_2$, the resulting mixture was stirred, heated to 150° C., and reacted for 8 h. Then, the heating was stopped, the resultant was cooled to room temperature, the reaction kettle was depressurized and opened, and the product was withdrawn for gas chromatographic analysis. The conversion of phenol was 100% and the selectivity to cyclohexanol was 99.8%.

Example 4-30

The nanocomposite material obtained in Example 2-10 was used as a catalyst in the reaction for producing cyclohexanol by the hydrogenation of phenol, and the experimental procedure was as follows:

0.2 g of the composite material, 7 mmol of phenol and 50 mL of water were added into a reaction kettle, the reaction kettle was purged with $H_2$ for 3 times, the pressure in the reaction kettle was raised to 3 MPa by introducing $H_2$, the resulting mixture was stirred, heated to 150° C., and reacted for 8 h. Then, the heating was stopped, the resultant was cooled to room temperature, the reaction kettle was depressurized and opened, and the product was withdrawn for gas chromatographic analysis. The conversion of phenol was 100% and the selectivity to cyclohexanol was 99.6%.

Example 4-31

The nanocomposite material obtained in Example 2-1 was used as a catalyst in the reaction for producing p-aminophenol by the hydrogenation of p-nitrophenol, and the experimental procedure was as follows:

0.1 g of the composite material, 2.4 mmol of p-nitrophenol and 30 mL of ethanol were added into a reaction kettle, the reaction kettle was purged with $H_2$ for 3 times, the pressure in the reaction kettle was raised to 1 MPa by introducing $H_2$, the resulting mixture was stirred, heated to 60° C., and reacted for 2 h. Then, the heating was stopped, the resultant was cooled to room temperature, the reaction kettle was depressurized and opened, and the product was withdrawn for gas chromatographic analysis. The conversion of p-nitrophenol was 100% and the selectivity to p-aminophenol was 99.9%.

Example 4-32

The nanocomposite material obtained in Example 2-10 was used as a catalyst in the reaction for producing p-aminophenol by the hydrogenation of p-nitrophenol, and the experimental procedure was as follows:

0.2 g of the composite material, 4.8 mmol of p-nitrophenol and 50 mL of ethanol were added into a reaction kettle, the reaction kettle was purged with $H_2$ for 3 times, the pressure in the reaction kettle was raised to 1 MPa by introducing $H_2$, the resulting mixture was stirred, heated to 60° C., and reacted for 2 h. Then, the heating was stopped, the resultant was cooled to room temperature, the reaction kettle was depressurized and opened, and the product was withdrawn for gas chromatographic analysis. The conversion of p-nitrophenol was 100% and the selectivity to p-aminophenol was 99.8%.

Example 4-33

The nanocomposite material obtained in Example 2-1 was used as a catalyst in the reaction for producing p-anisidine by the hydrogenation of p-nitroanisole, and the experimental procedure was as follows:

0.1 g of the composite material, 2.2 mmol of p-nitroanisole and 30 mL of ethanol were added into a reaction kettle, the reaction kettle was purged with $H_2$ for 3 times, the pressure in the reaction kettle was raised to 1 MPa by introducing $H_2$, the resulting mixture was stirred, heated to 100° C., and reacted for 2 h. Then, the heating was stopped, the resultant was cooled to room temperature, the reaction kettle was depressurized and opened, and the product was withdrawn for gas chromatographic analysis. The conversion of p-nitroanisole was 100%, and the selectivity to p-anisidine was 99.9%.

Example 4-34

The nanocomposite material obtained in Example 2-10 was used as a catalyst in the reaction for producing p-anisidine by the hydrogenation of p-nitroanisole, and the experimental procedure was as follows:

0.2 g of the composite material, 4.5 mmol of p-nitroanisole and 50 mL of ethanol were added into a reaction kettle, the reaction kettle was purged with $H_2$ for 3 times, the pressure in the reaction kettle was raised to 1.5 MPa by introducing $H_2$, the resulting mixture was stirred, heated to 80° C., and reacted for 2 h. Then, the heating was stopped, the resultant was cooled to room temperature, the reaction kettle was depressurized and opened, and the product was withdrawn for gas chromatographic analysis. The conversion of p-nitroanisole was 100%, and the selectivity to p-anisidine was 99.9%.

Example 4-35

The nanocomposite material obtained in Example 2-1 was used as a catalyst in the reaction for producing alcohols by the hydrogenation of ketones, and the experimental procedure was as follows:

0.1 g of the composite material, 5.8 mmol of acetone and 30 mL of cyclohexane were added into a reaction kettle, the reaction kettle was purged with $H_2$ for 3 times, the pressure in the reaction kettle was raised to 3 MPa by introducing $H_2$, the resulting mixture was stirred, heated to 150° C., and reacted for 8 h. Then, the heating was stopped, the resultant was cooled to room temperature, the reaction kettle was depressurized and opened, and the product was withdrawn for gas chromatographic analysis. The conversion of acetone was 99.1% and the selectivity to isopropanol was 99.9%.

Example 4-36

The nanocomposite material obtained in Example 2-10 was used as a catalyst in the reaction for producing alcohols by the hydrogenation of ketones, and the experimental procedure was as follows:

0.2 g of the composite material, 11.6 mmol of acetone and 50 mL of cyclohexane were added into a reaction kettle, the reaction kettle was purged with $H_2$ for 3 times, the pressure in the reaction kettle was raised to 3 MPa by introducing $H_2$, the resulting mixture was stirred, heated to 150° C., and reacted for 8 h. Then, the heating was stopped, the resultant was cooled to room temperature, the reaction kettle was depressurized and opened, and the product was withdrawn for gas chromatographic analysis. The conversion of acetone was 97.9% and the selectivity to isopropanol was 99.5%.

Example 4-37

The nanocomposite material obtained in Example 2-1 was used as a catalyst in the hydrogenation of olefins, and the experimental procedure was as follows:

0.1 g of the composite material, 3.2 mmol of styrene and 30 mL of cyclohexane were added into a reaction kettle, the reaction kettle was purged with $H_2$ for 3 times, the pressure in the reaction kettle was raised to 1.5 MPa by introducing $H_2$, the resulting mixture was stirred, heated to 120° C., and reacted for 2 h. Then, the heating was stopped, the resultant was cooled to room temperature, the reaction kettle was depressurized and opened, and the product was withdrawn for gas chromatographic analysis. The conversion of styrene was 100% and the selectivity to ethylbenzene was 99.8%.

Example 4-38

The nanocomposite material obtained in Example 2-10 was used as a catalyst in the hydrogenation reaction of olefins, and the experimental procedure was as follows:

0.2 g of the composite material, 6.4 mmol of styrene and 50 mL of cyclohexane were added into a reaction kettle, the reaction kettle was purged with $H_2$ for 3 times, the pressure in the reaction kettle was raised to 1.5 MPa by introducing $H_2$, the resulting mixture was stirred, heated to 120° C., and reacted for 2 h. Then, the heating was stopped, the resultant was cooled to room temperature, the reaction kettle was depressurized and opened, and the product was withdrawn for gas chromatographic analysis. The conversion of styrene was 100% and the selectivity to ethylbenzene was 99.6%.

Example 4-39

The nanocomposite material P2 obtained in Example 3-1 was used as a catalyst in the reaction for producing p-chloroaniline by the hydrogenation of p-chloronitrobenzene, and the experimental procedure was as follows:

3 g of the composite material, 10 g of p-chloronitrobenzene and 200 mL of absolute ethanol were added into a reaction kettle, the reaction kettle was purged with $H_2$ for 3 times, the pressure in the reaction kettle was raised to 2 MPa by introducing $H_2$, the resulting mixture was stirred, heated to 120° C., and reacted for 2 h. Then, the heating was stopped, the resultant was cooled to room temperature, the reaction kettle was depressurized and opened, and the product was withdrawn for gas chromatographic analysis. The conversion of p-chloronitrobenzene was 100% and the selectivity to chloroaniline was 98.5%.

In the foregoing context, the inventive concept of the present application has been described with reference to embodiments thereof. However, it can be appreciated by one of ordinary skill in the art that various modifications and changes can be made without departing from the scope of the present application as set forth in the appended claims. Accordingly, the description and figures should be interpreted in an illustrative rather than a restrictive manner, and all such modifications and changes are intended to be included within the scope of present invention.

The invention claimed is:

1. A nanocomposite material comprising carbon-coated transition metal particles, the carbon-coated transition metal particles having a core-shell structure, the shell layer being a graphitized carbon layer doped with oxygen and/or nitrogen, and the core being a transition metal nanoparticle, wherein the nanocomposite material is a porous material having at least one distribution peak of mesopores.

2. The nanocomposite material according to claim 1, wherein the nanocomposite material has a loss on acid leaching of 40% or less.

3. The nanocomposite material according to claim 1, further comprising an amorphous carbon matrix, the carbon-coated transition metal particles being dispersed in the amorphous carbon matrix.

4. The nanocomposite material according to claim 1, wherein the nanocomposite material has a proportion of mesopore volume to total pore volume of greater than about 50%, and the mesopore volume of the nanocomposite material is between about 0.05 cm$^3$/g and about 1.25 cm$^3$/g.

5. The nanocomposite material according to claim 1, wherein the nanocomposite material has a carbon content of about 10.0% to about 60.0% by mass and a transition metal content of about 30.0% to about 85.0% by mass.

6. The nanocomposite material according to claim 1, wherein the shell layer of the carbon-coated transition metal particles is a graphitized carbon layer doped with oxygen, and the nanocomposite material has an oxygen content of less than about 15.0% by mass; or the shell layer of the carbon-coated transition metal particles is a graphitized carbon layer doped with oxygen and nitrogen, and the nanocomposite material has a total content of nitrogen and oxygen of less than about 15.0% by mass, wherein the nitrogen content is preferably about 0.1% to about 10% by mass.

7. The nanocomposite material according to claim 1, wherein the nanocomposite material further has one or more of the following characteristics:
- the graphitized carbon layer has a thickness of about 0.3 nm to about 6 nm;
- the particle size of the core-shell structure is about 1 nm to about 200 nm; and
- the transition metal is one or more selected from the group consisting of iron, cobalt, nickel, copper, and zinc.

8. The nanocomposite material according to claim 1, wherein the shell layer of the carbon-coated transition metal particles is a graphitized carbon layer doped with oxygen and nitrogen, and the transition metal nanoparticles have a face-centered-cubic lattice structure and/or a hexagonal-close-packed lattice structure.

9. A method for the preparation of a nanocomposite material according to claim 1, comprising the steps of:
  i) mixing a mixture comprising a transition metal source and a polybasic organic carboxylic acid with a solvent to form a homogeneous solution;
  ii) removing the solvent from the homogeneous solution to obtain a precursor;
  iii) subjecting the precursor to high-temperature pyrolysis under an inert protective atmosphere or a reducing atmosphere; and
  iv) optionally, subjecting the pyrolysis product obtained in step iii) to a treatment by a non-oxidizing strong acid.

10. The method according to claim 9, wherein the mixture used in step i) further comprises a nitrogen-containing organic compound and/or an oxygen-containing organic compound that is different from the polybasic organic carboxylic acid, and optionally an additional organic compound.

11. The method according to claim 10, wherein the nitrogen-containing organic compound is one or more selected from the group consisting of urea, melamine, dicyanodiamine, hexamethylenetetramine, and amino acids, and the oxygen-containing organic compound is selected from the group consisting of polyols and organic carboxylic acids.

12. The method according to claim 10, wherein the mass ratio of the transition metal source, the polybasic organic carboxylic acid and the nitrogen-containing organic compound is about 1:0.1-100: 0.1-100.

13. The method according to claim 9, wherein the transition metal is one or more selected from the group consisting of iron, cobalt, nickel, copper, and zinc.

14. The method according to claim 9, wherein the transition metal source is one or more selected from the group consisting of organic acid salts, carbonates, basic carbonates, oxides, and hydroxides of transition metals.

15. The method according to claim 9, wherein the polybasic organic carboxylic acid is one or more selected from the group consisting of citric acid, maleic acid, trimesic acid, terephthalic acid, malic acid, EDTA, and dipicolinic acid.

16. The method according to claim 14, wherein the mass ratio of the transition metal source to the polybasic organic carboxylic acid is about 1:0.1 to about 1:10.

17. The method according to claim 14, wherein:
  the solvent used in step i) is selected from the group consisting of water, methanol, ethanol, n-propanol, isopropanol, and mixtures thereof;
  in step iii), the inert protective atmosphere is nitrogen or argon, and the reducing atmosphere is a mixed gas of an inert gas and hydrogen; the high-temperature pyrolysis is carried out by heating up to the temperature of a temperature-sustaining stage at a heating rate of about 0.5° C/min to about 30° C/min, and then keeping the temperature constant at the temperature-sustaining stage for about 20 min to about 600 min, with the temperature employed at the temperature-sustaining stage being about 400° C. to about 800° C.; and/or the non-oxidizing strong acid used in step iv) is one or more selected from the group consisting of hydrofluoric acid, hydrochloric acid, nitric acid, and sulfuric acid.

18. A method for treating a volatile organic compound, comprising contacting the volatile organic compound with the nanocomposite material of claim 1 to conduct a catalytic oxidation reaction.

19. A method for hydrogenation reduction reaction, comprising contacting a reactant to be hydrogenated with the nanocomposite material of claim 1 in the presence of hydrogen to conduct a catalytic hydrogenation reaction, wherein the reactant is selected from the group consisting of p-chloronitrobenzene nitrobenzene, nitrophenol p-nitroanisole, phenol, olefins, aromatic hydrocarbons, aldehydes, and ketones.

20. The nanocomposite material according to claim 1, wherein the nanocomposite material is a porous material having two or more distribution peaks of mesopores.

21. The nanocomposite material according to claim 1, wherein the nanocomposite material has a loss on acid leaching of 10% or less.

* * * * *